United States Patent
Pastan et al.

(10) Patent No.: US 10,683,362 B2
(45) Date of Patent: Jun. 16, 2020

(54) RECOMBINANT IMMUNOTOXIN TARGETING MESOTHELIN

(75) Inventors: Ira H. Pastan, Potomac, MD (US); John Weldon, Columbia, MD (US); Richard Beers, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 615 days.

(21) Appl. No.: 14/115,131

(22) PCT Filed: May 4, 2012

(86) PCT No.: PCT/US2012/036456
§ 371 (c)(1),
(2), (4) Date: Jan. 17, 2014

(87) PCT Pub. No.: WO2012/154530
PCT Pub. Date: Nov. 15, 2012

(65) Prior Publication Data
US 2014/0154248 A1 Jun. 5, 2014

Related U.S. Application Data

(60) Provisional application No. 61/483,531, filed on May 6, 2011.

(51) Int. Cl.
C07K 16/30 (2006.01)
C07K 14/21 (2006.01)
A61K 39/00 (2006.01)
A61K 47/68 (2017.01)

(52) U.S. Cl.
CPC .......... *C07K 16/30* (2013.01); *A61K 39/0011* (2013.01); *A61K 47/6829* (2017.08); *A61K 47/6851* (2017.08); *C07K 14/21* (2013.01); *C07K 2317/56* (2013.01); *C07K 2319/32* (2013.01); *C07K 2319/50* (2013.01); *C07K 2319/55* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 4,235,871 A | 11/1980 | Papahadjopoulos et al. |
| 4,458,066 A | 7/1984 | Caruthers et al. |
| 4,501,728 A | 2/1985 | Geho et al. |
| 4,816,567 A | 3/1989 | Cabilly et al. |
| 4,837,028 A | 6/1989 | Allen |
| 4,902,505 A | 2/1990 | Pardridge et al. |
| 4,946,778 A | 8/1990 | Ladner et al. |
| 4,957,735 A | 9/1990 | Huang |
| 5,004,697 A | 4/1991 | Pardridge |
| 5,019,369 A | 5/1991 | Presant et al. |
| 5,055,303 A | 10/1991 | Riley, Jr. |
| 5,132,405 A | 7/1992 | Huston et al. |
| 5,188,837 A | 2/1993 | Domb |
| 5,254,342 A | 10/1993 | Shen et al. |
| 5,268,164 A | 12/1993 | Kozarich et al. |
| 5,271,961 A | 12/1993 | Mathiowitz et al. |
| 5,413,797 A | 5/1995 | Khan et al. |
| 5,506,206 A | 4/1996 | Kozarich et al. |
| 5,514,670 A | 5/1996 | Friedman et al. |
| 5,530,101 A | 6/1996 | Queen et al. |
| 5,534,496 A | 7/1996 | Lee et al. |
| 5,585,089 A | 12/1996 | Queen et al. |
| 5,591,828 A | 1/1997 | Bosslet |
| 5,602,095 A | 2/1997 | Pastan et al. |
| 5,693,762 A | 12/1997 | Queen et al. |
| 5,747,654 A | 5/1998 | Pastan et al. |
| 5,821,238 A | 10/1998 | Pastan et al. |
| 5,854,044 A | 12/1998 | Pastan et al. |
| 5,859,205 A | 1/1999 | Adair et al. |
| 5,888,773 A | 3/1999 | Jost et al. |

(Continued)

FOREIGN PATENT DOCUMENTS

| | | |
|---|---|---|
| EP | 0 173 494 A2 | 3/1986 |
| EP | 0 404 097 A2 | 12/1990 |

(Continued)

OTHER PUBLICATIONS

Akiyama et al., "Isolation and genetic characterization of human KB cell lines resistant to multiple drugs," *Somat Cell Mol. Genet.*, 11(2), 117-26 (1985).
Allured et al., "Structure of exotoxin A of Pseudomonas aeruginosa at 3.0-Angstrom resolution," *Proc. Natl. Acad. Sci. U.S.A.*, 83(5), 1320-4 (1986).
Altschul et al., "Basic local alignment search tool," *J. Mol. Biol.*, 215, 403-410 (1990).
Altschul et al, "Gapped BLAST and PSI-BLAST: a new generation of protein database search programs," *Nucleic Acids Res.*, 25, 3389-3402 (1977).
Arbabi-Ghahroudi et al., "Selection and identification of single domain antibody fragments from camel heavy-chain antibodies," *FEBS Lett.*, 414, 521-6 (1997).

(Continued)

Primary Examiner — Nelson B Moseley, II
(74) Attorney, Agent, or Firm — Leydig, Voit & Mayer

(57) ABSTRACT

Mesothelin is a differentiation antigen present on the surface of ovarian cancers, mesotheliomas and several other types of human cancers. Because among normal tissues, mesothelin is only present on mesothelial cells, it represents a good target for antibody mediated delivery of cytotoxic agents. The present invention is directed to improved recombinant immunotoxins comprising anti-mesothelin antibodies, including Fv molecules with particularly high affinity for mesothelin, and a *Pseudomonas* Exotoxin moiety which has been modified to reduce its immunogenicity and protease sensitivity and providing a better cytotoxicity for cells which express mesothelin. The RITs are well-suited for the treatment of cancers of the ovary, stomach, squamous cells, mesotheliomas and other malignant cells expressing mesothelin.

27 Claims, 12 Drawing Sheets

Specification includes a Sequence Listing.

(56) References Cited

U.S. PATENT DOCUMENTS

| | | |
|---|---|---|
| 6,083,502 A | 7/2000 | Pastan et al. |
| 6,153,430 A | 11/2000 | Pastan et al. |
| 6,180,377 B1 | 1/2001 | Morgan et al. |
| 6,211,338 B1* | 4/2001 | Malcolm ............... C07K 14/005 435/219 |
| 6,407,213 B1 | 6/2002 | Carter et al. |
| 6,558,672 B1 | 5/2003 | Pastan et al. |
| 6,809,184 B1 | 10/2004 | Pastan et al. |
| 7,081,518 B1 | 7/2006 | Pastan et al. |
| 7,381,408 B2 | 6/2008 | Mezo et al. |
| 7,592,426 B2 | 9/2009 | Ebel et al. |
| 2004/0091503 A1* | 5/2004 | Segal ................... A61K 39/145 424/192.1 |
| 2004/0223966 A1* | 11/2004 | Wolfman ............... C07K 14/71 424/145.1 |
| 2005/0054832 A1* | 3/2005 | Lazar ..................... C07K 16/00 530/387.3 |
| 2006/0263368 A1* | 11/2006 | Rosenblum ........ A61K 41/0038 424/155.1 |
| 2008/0170991 A1 | 7/2008 | Shi et al. |

FOREIGN PATENT DOCUMENTS

| | | | |
|---|---|---|---|
| JP | 2008-523105 A | 7/2008 | |
| JP | 2008-526889 A | 7/2008 | |
| JP | 2009-514537 A | 4/2009 | |
| WO | WO 87/02671 A1 | 5/1987 | |
| WO | WO 93/11161 A1 | 6/1993 | |
| WO | WO 97/25068 A2 | 7/1997 | |
| WO | WO 98/45322 A2 | 10/1998 | |
| WO | WO 99/51643 A1 | 10/1999 | |
| WO | WO 2000/73346 A1 | 12/2000 | |
| WO | WO 2006/065867 * | 6/2006 | ............. C07K 14/21 |
| WO | WO 2006-065867 A2 | 6/2006 | |
| WO | WO 2006-074451 A2 | 7/2006 | |
| WO | WO 2007/016150 A2 | 2/2007 | |
| WO | WO 2007-097812 A1 | 8/2007 | |
| WO | WO 2009/032954 A1 | 3/2009 | |
| WO | WO 2009/032954 * | 12/2009 | ............. C07K 14/21 |
| WO | WO 2011/032022 A1 | 3/2011 | |
| WO | WO 2012/154530 A1 | 11/2012 | |

OTHER PUBLICATIONS

Arndt et al, "Helix-stabilized Fv (hsFv) antibody fragments: substituting the constant domains of a Fab fragment for a heterodimeric coiled-coil domain," *J. Mol. Niol.*, 312(1), 221-8 (2001).

Bang et al., "HA22 (R490A) is a recombinant immunotoxin with increased antitumor activity without an increase in animal toxicity," *Clin. Cancer Res.*, 11(4), 1545-50 (2005).

Beaucage et al., "Deoxynucleoside phosphoramidites—a new class of key intermediates for deoxypolynucleotide synthesis," *Tetra. Lett.*, 22, 1859-62 (1981).

Bird et al., "Single-chain antigen-binding proteins," *Science*, 242, 4236 (1988).

Bravo et al., "Accurate and efficient cleavage of the human insulin proreceptor by the human proprotein-processing protease furin. Characterization and kinetic parameters using the purified, secreted soluble protease expressed by a recombinant baculovirus," *J. Biol. Chem*, 269, 25830-25837 (1994).

Brinkmann et al., "Cloning and expression of the recombinant FAb fragment of monoclonal antibody K1 that reacts with mesothelin present on mesotheliomas and ovarian cancers," *Int. J. Cancer*, 71(4), 638-44 (1997).

Brown et al., "Chemical synthesis and cloning of a tyrosine tRNA gene," *Meth Enzymol.*, 68, 109-151 (1979).

Buchner et al., "A method for increasing the yield of properly folded recombinant fusion proteins: single-chain immunotoxins from renaturation of bacterial inclusion bodies," *Anal. Biochem.*, 205, 263-70 (1992).

Chang et al., "Molecular cloning and expression of a cDNA encoding a protein detected by the K1 antibody from an ovarian carcinoma (OVCAR-3) cell line," *Int. J. Cancer*, 57(1), 1994.

Chang et al. "Molecular cloning of mesothelin, a differentiation antigen present on mesothelium, mesotheliomas, and ovarian cancers," *Proc. Natl. Acad. Sci. U.S.A.*, 93, 136-140 (1996).

Chiron et al., "Furin-mediated cleavage of Pseudomonas exotoxin-derived chimeric toxins," *J. Biol. Chem.*, 272(50), 31707-11 (1997).

Chowdhury et al., "Isolation of anti-mesothelin antibodies from a phage display library," *Mol. Immunol.*, 34, 9-20 (1997).

Chowdhury et al., "Isolation of a high-affinity stable single-chain Fv specific for mesothelin from DNA-immunized mice by phage display and construction of a recombinant immunotoxin with anti-tumor activity," *PNAS*, 95(2), 669-74 (1998).

Chowdhury et al., "Improving antibody affinity by mimicking somatic hypermutation in vitro," *Nat. Biotechnol.*, 17(6), 568-572 (1999).

Davies et al., "Antibody VH Domains as Small Recognition Units," *Biotechnology*, 13, 475-9 (1995).

Decker et al., "Induction of caspase-dependent programmed cell death in B-cell chronic lymphocytic leukemia by anti-CD22 immunotoxins," *Blood*, 103(7), 2718-26 (2004).

Du et al., "New immunotoxins targeting CD123, a stem cell antigen on acute myeloid leukemia cells," *J. Immunother.*, 30(6), 607-13 (2007).

Duckert et al., "Prediction of proprotein convertase cleavage sites," *Protein Eng. Des. Sel.*, 17(1), 107-12 (2004).

Ellison et al., "Nucleotide sequence of a human immunoglobulin C gamma 4 gene," *DNA*, 1, 11-8 (1981).

Ellison et al., "Linkage and sequence homology of two human immunoglobulin gamma heavy chain constant region genes," *Proc. Natl. Acad. Sci. U.S.A.*, 79, 1984-8 (1982).

Ellison et al., "The nucleotide sequence of a human immunoglobulin C gamma1 gene," *Nucleic Acids Res.*, 10(13), 4071-9 (1982).

Evers et al., "Quantitative understanding of the energy transfer between fluorescent proteins connected via flexible peptide linkers," *Biochemistry*, 45(44), 13183 (2006).

Feng et al., "A novel human monoclonal antibody that binds with high affinity to mesothelin-expressing cells and kills them by antibody-dependent cell-mediated cytotoxicity," *Mol. Cancer Ther.*, 8(5), 1113-8 (2009).

Filpula et al., "Releasable PEGylation of mesothelin targeted immunotoxin SS1P achieves single dosage complete regression of a human carcinoma in mice," *Bioconjug. Chem.*, 18(3), 773-84 (2007).

Fitzgerald, D., "Why toxins!" *Semin Cancer Biol.*, 7(2), 87-95 (1996).

Frankel et al., "Targeted toxins," *Clin. Cancer Res.*, 6(2), 326-34 (2000).

Genbank Accession No. NM_001100374.1 "Bos taurus mesothelin (MSLN), mRNA," (Sep. 11, 2013).

Genbank Accession No. NM_005823.4 "*Homo sapiens* mesothelin (MSLN), transcript variant 1, mRNA," (Nov. 3, 2013).

Genbank Accession No. NM_013404.3 "*Homo sapiens* microarray element probe ILMN_2353161 for mesothelin (MSLN)," (Nov. 3, 2013).

Genbank Accession No. NM_018857.1 "Mus musculus mesothelin (Msln), mRNA," (Oct. 26, 2013).

Genbank Accession No. NM_031658.1 "Rattus norvegicus mesothelin (Msln), mRNA," (Apr. 18, 2013).

Genbank Accession No. NP_037536.2 "Mesothelin isoform 2 preproprotein [*Homo sapiens*]" (Nov. 3, 2013).

Genbank Accession No. NP_001093844.1 "Mesothelin precursor [Bos taurus]" sequence (Sep. 11, 2013).

Genbank Accession No. NP_005814.2 "Mesothelin isoform 1 preproprotein [*Homo sapiens*]" (Nov. 3, 2013).

Genbank Accession No. NP_061345.1 "Mesothelin precursor [Mus musculus]" sequence (Oct. 26, 2013).

Genbank Accession No. NP_113846.1 "Mesothelin precursor [Rattus norvegicus]" sequence (Apr. 18, 2013).

Glockshuber et al., "A comparison of strategies to stabilize immunoglobulin Fv-fragments," *Biochemistry*, 29(6), 1362-7 (1990).

(56) References Cited

OTHER PUBLICATIONS

Goyal et al., "Inclusion of a furin-sensitive spacer enhances the cytotoxicity of ribotoxin restrictocin containing recombinant single-chain immunotoxins," *Biochem. J.*, 345, 247-54 (2000).
Gu et al., "Furin regulates both the activation of Pseudomonas exotoxin A and the quantity of the toxin receptor expressed on target cells," *Infect. Immun.*, 64(2), 524-7 (1996).
Hansen et al., "A recombinant immunotoxin targeting CD22 with low immunogenicity, low nonspecific toxicity, and high antitumor activity in mice," *J. Immunother.*, 33(3), 297-304 (2010).
Harmsen et al., "Properties, production, and applications of camelid single-domain antibody fragments," *Appl. Microbiol. Biotechnol.*, 77(1), 13-22 (2007).
Hassan et al., "Antitumor activity of SS(dsFv)PE38 and SS1(dsFv)PE38, recombinant antimesothelin immunotoxins against human gynecologic cancers grown in organotypic culture in vitro," *Clin. Cancer Res.*, 8(11), 3520-6 (2002).
Hassan et al., "Phase I study of SS1P, a recombinant anti-mesothelin immunotoxin given as a bolus I.V. infusion to patients with mesothelin-expressing mesothelioma, ovarian, and pancreatic cancers," *Clin. Cancer Res.*, 13(17), 5144-9 (2007).
Hatsuzawa et al., "Purification and characterization of furin, a Kex2-like processing endoprotease, produced in Chinese hamster ovary cells," *J. Biol. Chem.*, 267(23), 16094-9 (1992).
Henikoff et al., "Amino acid substitution matrices from protein blocks," *PNAS*, 89, 10915-10919 (1992).
Holliger et al., "Diabodies: small bivalent and bispecific antibody fragments" *PNAS*, 90, 6444-6448 (1993).
Holt et al., "Domain antibodies: proteins for therapy," *Trends Biotechnol.*, 21(11), 484-90 (2003).
Honjo et al., "Cloning and complete nucleotide sequence of mouse immunoglobulin gamma 1 chain gene," *Cell*, 18(2), 559-68 (1979).
Huse et al., "Generation of a large combinatorial library of the immunoglobulin repertoire in phage lambda," *Science*, 246, 1275-81 (1989).
Huston et al., "Protein engineering of antibody binding sites: recovery of specific activity in an anti-digoxin single-chain Fv analogue produced in *Escherichia coli*," *PNAS*, 85(16), 5879-83 (1988).
Hwang et al., "Functional domains of Pseudomonas exotoxin identified by deletion analysis of the gene expressed in *E.coli*," *Cell*, 48(1), 129-36 (1987).
Ijntema et al., "Hydroxyapatite microcarriers for biocontrolled release of protein drugs," *Int. J. Pharm.*, 112, 215-224 (1994).
Inocencio et al., "Furin activates Pseudomonas exotoxin A by specific cleavage in vivo and in vitro," *J. Biol. Chem.*, 269(50), 31831-5 (1994).
International Search Report, International Application No. PCT/US2012/036456, datd Aug. 23, 2012.
Johannes et al., "Protein toxins: intracellular trafficking for targeted therapy," *Gene Ther.*, 12, 1360-1368 (2005).
Johnston et al., "Sustained delivery of interleukin-2 from a poloxamer 407 gel matrix following intraperitoneal injection in mice," *Pharm. Res.*, 9, 425-34 (1992).
Jones et al., "Replacing the complementarity-determining regions in a human antibody with those from a mouse," *Nature*, 321, 522-525 (1986).
Karlin et al., "Applications and statistics for multiple high-scoring segments in molecular sequences," *PNAS*, 90, 5873-5787 (1993).
Kihara et al., "Analysis of sequences required for the cytotoxic action of a chimeric toxin composed of Pseudomonas exotoxin and transforming growth factor alpha," *Bioconjug. Chem.*, 5(6), 532-8 (1994).
Kreitman, RJ., "Immunotoxins for targeted cancer therapy," *AAPS J.*, 8(3), E332-51 (2006).
Kreitman et al., "Importance of the glutamate residue of KDEL in increasing the cytotoxicity of Pseudomonas exotoxin derivatives and for increased binding to the KDEL receptor," *Biochem. J.*, 307, 29-37 (1995).
Kreitman et al., "Phase I trial of continuous infusion anti-mesothelin recombinant immunotoxin SS1P," *Clin. Cancer Res.*, 15(16), 5274-9 (2009).
Kreitman et al., "Phase I trial of recombinant immunotoxin RFB4(dsFv)-PE38 (BL22) in patients with B-cell malignancies," *J. Clin. Oncol.*, 23(27), 6719-29 (2005).
Kreitman et al., "Phase II trial of recombinant immunotoxin RFB4(dsFv)-PE38 (BL22) in patients with hairy cell leukemia," *J. Clin. Oncol.*, 27(18), 2983-90 (2009).
Langer, R., "Polymer-controlled drug delivery systems," *Accounts Chem. Res.*, 26, 537-42 (1993).
Lauwereys et al., "Potent enzyme inhibitors derived from dromedary heavy-chain antibodies," *EMBO J.*, 17(13), 3512-20 (1998).
Liu et al., "Recombinant immunotoxin engineered for low immunogenicity and antigenicity by identifying and silencing human B-cell epitopes," *PNAS*, 109(29), 11782-7 (2012).
Merrifield et al., "Solid phase peptide synthesis. I. The synthesis of a tetrapeptide," *J. Am. Chem. Soc.*, 85, 2149-2156 (1963).
Moehring et al., "Expression of mouse furin in a Chinese hamster cell resistant to Pseudomonas exotoxin A and viruses complements the genetic lesion," *J. Biol. Chem.*, 268(4), 2590-4 (1993).
Molloy et al., "Human furin is a calcium-dependent serine endoprotease that recognizes the sequence Arg-X-X-Arg and efficiently cleaves anthrax toxin protective antigen," *J. Biol. Chem.*, 267(23), 16396-402 (1992).
Morlon-Guyot et al., "Processing of Pseudomonas aeruginosa exotoxin A is dispensable for cell intoxication," *Infect. Immun.*, 77(7), 3090-9 (2009).
Mufson, R.A., "Tumor antigen targets and tumor immunotherapy," *Front Biosci.*, 11, 337-43 (2006).
Narang et al., "Improved phosphotriester method for the synthesis of gene fragments," *Meth. Enzymol.*, 68, 90-99 (1979).
Needham-Vandevanter et al., "Characterization of an adduct between CC-1065 and a defined oligodeoxynucleotide duplex," *Nucl. Acids Res.*, 12, 6159-6168 (1984).
Needleman et al., "A general method applicable to the search for similarities in the amino acid sequence of two proteins," *J. Mol. Biol.*, 48, 443-453 (1970).
Onda et al., "Inhibition of TNF-alpha produced by Kupffer cells protects against the nonspecific liver toxicity of immunotoxin anti-Tac(Fv)-PE38, LMB-2," *J. Immunol.*, 165(12), 7150-6 (2000).
Onda et al., "Lowering the isoelectric point of the Fv portion of recombinant immunotoxins leads to decreased nonspecific animal toxicity without affecting antitumor activity," *Cancer Res.*, 61, 5070-7 (2001).
Onda et al., "Characterization of the B cell epitopes associated with a truncated form of Pseudomonas exotoxin (PE38) used to make immunotoxins for the treatment of cancer patients," *J. Immunol.*, 177, 8822-34 (2006).
Onda et al., "An immunotoxin with greatly reduced immunogenicity by identification and removal of B cell epitopes," *Proc. Natl. Acad. Sci. U.S.A.*, 105(32), 11311-6 (2008).
Onda et al., "Recombinant immunotoxin against B-cell malignancies with no immunogenicity in mice by removal of B-cell epitopes," *PNAS*, 108, 5742-7 (2011).
Ornatowski et al., "Elevated furin levels in human cystic fibrosis cells result in hypersusceptibility to exotoxin A-induced cytotoxicity," *J. Clin. Invest.*, 117(11), 3489-97 (2007).
Pai et al., "Treatment of advanced solid tumors with immunotoxin LMB-1: an antibody linked to pseudomonas exotoxin," *Nat. Med.*, 2(3), 350-3 (1996).
Pastan et al., "Recombinant immunotoxins in the treatment of cancer," *Methods Mol. Biol.*, 248, 503-18 (2004).
Pearson et al., "Improved tools for biological sequence comparison," *PNAS*, 85, 2444-2448 (1988).
Pec et al., "Sustained-release of urease from a polozamer gel matrix," *J. Parent. Sci. Tech.*, 44(2), 58-65 (1990).
Pluckthun, A., "Antibody engineering: advances from the use of *Escherichia coli* expression systems," *Biotechnology*, 9, 545-551 (1991).

(56) References Cited

OTHER PUBLICATIONS

Powell et al., "Administration of a CD25-directed immunotoxin, LMB-2, to patients with metastatic melanoma induces a selective partial reduction in regulatory T cells in vivo," *J. Immunol.*, 179(7), 4919-28 (2007).
Reiter et al., "Antibody engineering of recombinant Fv immunotoxins for improved targeting of cancer: disulfide-stabilized Fv immunotoxins," *Clin. Cancer Res.*, 2, 245-252 (1996).
Reiter et al., "An antibody single-domain phage display library of a native heavy chain variable region: isolation of functional single-domain VH molecules with a unique interface," *J. Mol. Biol.*, 290, 685-698 (1999).
Riechmann et al., "Reshaping human antibodies for therapy," *Nature*, 332, 323-7 (1988).
Rockwell et al., "The kindest cuts of all: crystal structures of Kex2 and furin reveal secrets of precursor processing," *Trends Biochem. Sci.*, 29, 80-7 (2004).
Rozemuller et al., "Isolation of new anti-CD30 SCFVS from DNA-immunized mice by phage display and biologic activity of recombinant immunotoxins produced by fusion with truncated pseudomonas exotin," *Int. J. Cancer*, 92, 861-70 (2001).
Saerens et al., "Single-domain antibodies as building blocks for novel therapeutics," *Curr. Opin. Pharmacol.*, 8(5), 600-8 (2008).
Salvatore et al., "Improved cytotoxic activity toward cell lines and fresh leukemia cells of a mutant anti-CD22 immunotoxin obtained by antibody phage display," *Clin. Cancer Res.*, 8, 995-1002 (2002).
Sampson et al., "Intracerebral infusion of an EGFR-targeted toxin in recurrent malignant brain tumors," *Neuro Oncol.*, 10(3), 320-9 (2008).
Sarac et al., "The furin inhibitor hexa-D-arginine blocks the activation of Pseudomonas aeruginosa exotoxin A in vivo," *Infect. Immuno.*, 70(12), 7136-9 (2002).
Saxena et al., "Formation of three-dimensional structure in proteins. I. Rapid nonenzymic reactivation of reduced lysozyme," *Biochemistry*, 9, 5015-5021 (1970).
Seetharam et al., "Increased cytotoxic activity of Pseudomonas exotoxin and two chimeric toxins ending in KDEL," *J. Biol. Chem*, 266(26), 17376-81 (1991).
Shiryaev et al., "Targeting host cell furin proprotein convertases as a therapeutic strategy against bacterial toxins and viral pathogens," *J. Biol. Chem.*, 282(29), 20847-53 (2007).
Siegall et al., "Functional analysis of domains II, Ib, and III of Pseudomonas exotoxin," *J. Biol. Chem*, 264(24), 14256-61 (1989).
Siegall et al., "Prevention of immunotoxin-mediated vascular leak syndrome in rats with retention of antitumor activity," *PNAS*, 91, 9514-8 (1994).
Siegall et al., "Characterization of vascular leak syndrome induced by the toxin component of Pseudomonas exotoxin-based immunotoxins and its potential inhibition with nonsteroidal anti-inflammatory drugs," *Clin. Cancer Res.*, 3, 339-45 (1997).
Smith et al., "Comparison of Biosequences," *Adv. Appl. Math*, 2, 482-489 (1981).
Stemmer et al., "Selection of an active single chain Fv antibody from a protein linker library prepared by enzymatic inverse PCR," *Biotechniques*, 14(2), 256-65 (1993).
Thomas, G., "Furin at the cutting edge: from protein traffic to embryogenesis and disease," *Nat. Rev. Mol. Cell Biol.*, 3(10), 753-66 (2002).
Thomas et al. "Mesothelin-specific CD8(+) T cell responses provide evidence of in vivo cross-priming by antigen-presenting cells in vaccinated pancreatic cancer patients," *J. Exp. Med.*, 200(3), 297-306 (2004).

Tucker et al., "Sequence of the cloned gene for the constant region of murine gamma 2b immunoglobulin heavy chain," *Science*, 206, 1303-6 (1979).
Vaughan et al., "Human antibodies with sub-nanomolar affinities isolated from a Large Non-immunized phage display library, " *Nature Biotech.*, 14, 309-314 (1996).
Verhoeyen et al., "Reshaping human antibodies: grafting an antilysozyme activity," *Science*, 239, 1534-6 (1988).
Ward et al., "Binding activities of a repertoire of single immunoglobulin variable domains secreted from *Escherichia coli*," *Nature*, 341, 544-546 (1989).
Wayne et al., "Anti-CD22 immunotoxin RFB4(dsFv)-PE38 (BL22) for CD22-positive hematologic malignancies of childhood: preclinical studies and phase I clinical trial," *Clin. Cancer Res.*, 16(6), 1894-903 (2010).
Weldon et al., "A protease-resistant immunotoxin against CD22 with greatly increased activity against CLL and diminished animal toxicity," *Blood*, 113(16), 3792-3800 (2009).
Weldon et al., "A guide to taming a toxin—recombinant immunotoxins constructed from Pseudomonas exotoxin a for the treatment of cancer," *FEBS J.*, 278(23), 4683-700 (2011).
Wesolowski et al, "Single domain antibodies: promising experimental and therapeutic tools in infection and immunity," *Med. Microbiol. Immunol.*, 198(3), 157-74 (2009).
Winter et al., "Man-made antibodies," *Nature*, 349, 293-9 (1991).
Written Opinion, International Application No. PCT/US2012/036456, datd Aug. 23, 2012.
Xiang et al., "The development and characterization of a human mesothelioma in vitro 3D model to investigate immunotoxin therapy," *PLoS One*, 6(1), e14640 (2011).
Yamao et al., "UGA is read as tryptophan in Mycoplasma capricolum," *PNAS*, 82, 2306-9 (1985).
Yamawaki et al., "Complete nucleotide sequence of immunoglobulin gamma2b chain gene cloned from newborn mouse DNA," *Nature*, 283, 786-9 (1980).
Yang et al., "Development of optimal bicistronic lentiviral vectors facilitates high-level TCR gene expression and robust tumor cell recognition," *Gene Ther.*, 15(21), 1411-23 (2008).
Zhang et al., "Synergistic antitumor activity of taxol and immunotoxin SS1P in tumor-bearing mice," *Clin. Cancer Res.*, 12(15), 4695-701 (2006).
Yan et al., "Research Progress in the Linker of Fusion Protein," *Biotechnology*, 18(3), 92-94 (2008).
"Registry of Standard Biological Parts: Protein domains/Linker"; htp://parts.igem.org/Protein_domains/Linker: printed May 19, 2016.
Edwards et al., "Epidermal growth factor receptor binding is affected by structural determinants in the toxin domain of transforming growth factor-alpha-Pseudomonas exotoxin fusion proteins," *Mol. and Cellular Biol.*, 9(7): 2860-67 (1989).
Kreitman et al., "Single-chain immunotoxin fusions between anti-Tac and Pseudomonas exotoxin: relative importance of the two toxin disulfide bonds," *Bioconjugate Chem.*, 4:112-120 (1993).
Madshus et al., "Effects of eliminating a disulfide bridge within domain II of Pseudomonas aeruginosa exotoxin A," *Infection and Immunity*, 57(7): 1873-78 (1989).
McKee et al., "Reduction of furin-nicked Pseudomonas exotoxin A: an unfolding story," *Biochemistry* 38: 16507-13 (1999).
Weldon et al., "Recombinant Immunotoxin against the Tumor-Associated Antigen Mesothelin Reengineered for High Activity, Low Off-Target Toxicity, and Reduced Antigenicity," *Mol. Cancer Ther.*, 12(1): 58-57 (2013).
Weldon et al., "Designing the Furin-Cleavable Linker in Recombinant Immunotoxins Based on Pseudomonas Exotoxin A," *Bioconjug. Chem.*, 26(6); 1120-1128 (2015).

* cited by examiner

Figure 1

A  Furin Cleavage Site
C...RHRQPRGWEQL...C

SS1P
dsFv-PE38

ASGG

B

| | | |
|---|---|---|
| SS1-LR | ASGG | RHRQPRGWEQL |
| SS1-LR/GGS | ASGG | RHRQPRGWEQL GGS |
| SS1-LR/GGSx2 | ASGG SGGG | RHRQPRGWEQL GGSGGGS |
| SS1-LR/2xFurin | ASGG | RHRQPRGWEQL GGS RHRQPRGWEQL GGS |
| SS1-LR/GGS R279G | ASGG | RHRQPGGWEQL GGS |

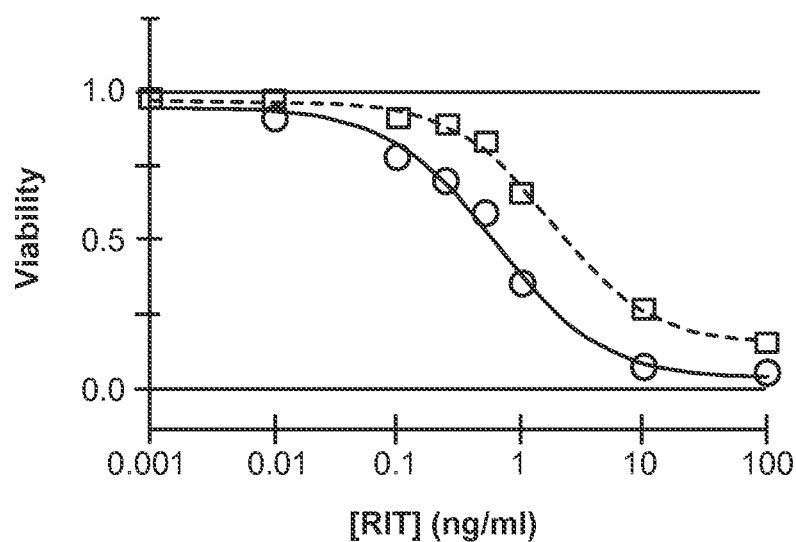

○ SS1P
□ SS1-LR

M30

A431/K5

○ SS1P
□ SS1-LR

OVCAR-8

A1847

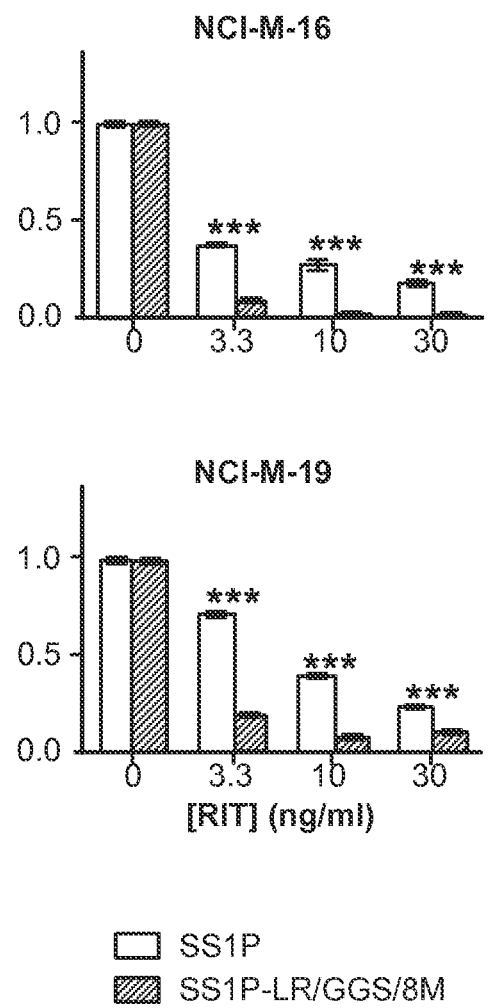

RECOMBINANT IMMUNOTOXIN TARGETING MESOTHELIN

CROSS-REFERENCES TO RELATED APPLICATIONS

This application is the U.S. National Phase of International Patent Application No. PCT/US2012/036456, filed May 4, 2012, which claims the benefit of priority of U.S. Provisional Patent Application No. 61/483,531, filed on May 6, 2011, each of which is incorporated herein by reference in its entirety.

STATEMENT AS TO RIGHTS TO INVENTIONS MADE UNDER FEDERALLY SPONSORED RESEARCH AND DEVELOPMENT

This invention was made with Government support under project number BC008753 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 46,882 Byte ASCII (Text) file named "714464SeqLis_ST25.TXT," dated Apr. 12, 2018.

BACKGROUND OF THE INVENTION

Recombinant immunotoxins (RITs) are engineered therapeutic proteins that combine an antibody fragment with a cytotoxic protein derived from a bacterial or plant source. RITs are designed to be selective agents for the targeted elimination of cells without many of the secondary toxicities associated with chemotherapeutic strategies. RITs for the treatment of cancers can be constructed by fusing the variable fragment (Fv) of antibodies against tumor associated cell surface antigens to a fragment of *Pseudomonas* exotoxin A (PE). RITs using a 38-kDa truncation of *Pseudomonas* exotoxin A (PE38) have met with noteworthy successes in clinical trials, but have limitations that include poor solid tumor penetration, high immunogenicity, and nonspecific toxicities (Kreitman R J et al., *Clin Cancer Res.*, 15(16):5274-9 (2009; Hassan R et al., *Clin Cancer Res.*, 13(17):5144-9 (2007); Wayne A S et al., *Clin Cancer Res.*, 16(6):1894-903 (2010); Kreitman R J et al., *J Clin Oncol.*, 27(18):2983-90 (2009); Sampson J H et al., *Neuro Oncol.*, 10(3):320-9 (2008); Powell D J Jr et al., *J Immunol.*, 179(7):4919-28 (2007); Kreitman R J, *J Clin Oncol.*, 23(27): 6719-29 (2005); Pal L H et al., *Nat. Med.*, 2(3):350-3 (1996)).

In an effort to improve the outcome of treatment with RITs, a knowledge of the PE intoxication pathway is important to understanding the design of these proteins. RITs are internalized via receptor-mediated endocytosis and traffic through the endolysosomal system to the Golgi, where they undergo retrograde transport to the endoplasmic reticulum (ER). During this trafficking stage the toxin is activated through reduction of a disulfide bond and cleavage by the protease furin at a site in PE38, which separates the Fv from the PE fragment. Subsequently, the activated PE must translocate into the cytosol, where it ADP-ribosylates and inactivates elongation factor 2, an essential component of the translation apparatus. This halts protein synthesis and eventually leads to cell death (for a review of the PE intoxication pathway see 9). Previous strategies designed to improve the cytotoxic activity of PE-based RITs include substitution of the C-terminal residues of PE, REDLK (SEQ ID NO:15), with the canonical ER-retention signal KDEL (SEQ ID NO:16) (Seetharam S et al., *J Biol Chem.*, 266(26):17376-81 (1991); Du X, Ho M, and Pastan I, *J Immunother.*, 30(6): 607-13 (2007); Rozemuller H. et al., *Int J Cancer.*, 92(6): 861-70 (2001); Kreitman R J and Pastan I., *Biochem J.*, 307 (Pt 1):29-37 (1995)). This change is known to enhance the cytotoxicity of PE, presumably by improving the efficiency of retrograde transport to the ER from the Golgi. This strategy is effective, but typically enhances the nonspecific toxicity of the RIT as well. Another strategy is to enhance the productive internalization of the RIT-receptor complex, and thereby increase the amount of toxin in the cell, by improving the affinity between the Fv and its target (Salvatore G et al., *Chn Cancer Res.*, 8(4):995-1002 (2002); Decker T et al., *Blood.*, 103(7):2718-26 (2004)).

More recently, a protease-resistant RIT has been designed to withstand degradation in the endolysosomal system, a potential barrier to effective immunotoxin treatment (Johannes L and Decaudin D, *Gene Ther.*, 12(18):1360-8 (2005); Fitzgerald D. Why toxins *Semin Cancer Biol.*, 7(2):87-95 (1996)). This "lysosomal degradation resistant" (LR) variant RIT was produced by removing protease-sensitive regions of PE38, and targeting it to the B-cell CD22 receptor with a high affinity anti-CD22 Fv derived from the RIT HA22 (Weldon J E, *Blood.*, 113(16):3792-800 (2009)). The LR mutation did not seriously affect in vitro activity on cell lines, but greatly reduced nonspecific toxicity in mice and dramatically enhanced activity on patient-derived chronic lymphocytic leukemia (CLL) cells in vitro. Additionally, the LR variant eliminates two major mouse B cell epitope groups (Onda M et al., *J Immunol.*, 177(12): 8822-34 (2006)) and antigen processing sites from PE38, helping to reduce its immunogenicity in mice (Hansen J K et al., *J Immunother.*, 33(3):297-304 (2010)). Due to the modular nature of RITs, the LR variant of PE can be targeted to other tumor-associated antigens by exchanging one Fv for another. Accordingly, the art disclosing the reduction in Domain II and Ib of PE teaches generally the advantages of removing protease sensitive and antigenic sites from the molecule. This art also generally teaches the pharmacokinetic advantages of the smaller RITs which results from these changes.

A clinically relevant target candidate is the tumor associated antigen mesothelin, which is often highly expressed in cancers that include mesotheliomas and cancers of the lung, ovary, and pancreas. Accordingly, there is a need for improved RITs which specifically target cancer cells which express mesothelin on their surfaces. This invention provides for these and other needs by providing RITs, pharmaceutical compositions, and methods of treatment for cancers which express or overexpress mesothelin.

BRIEF SUMMARY OF THE INVENTION

The present invention provides an improved *Pseudomonas* exotoxin A ("PE") with reduced immunogenicity, improved resistance to lysosomal proteases, and improved cytotoxicity for cells expressing mesothelin. Structurally, the improved PE of the invention has Domain I of PE removed, most of Domain II of PE removed, and a functional PE Domain III, optionally, with substitutions a) of PE Domain III amino acid residue positions D406, R432, R467, R490, R513, E548, K590 and/or Q592 with a glycine, alanine or serine and/or b) of PE Domain III amino acid residue positions D403, R412, R427, E431, R458, D461, R505, E522, R538, R551, R576 and/or L597 by glycine, serine, or alanine. The improvement lies in the insertion of a short and flexible peptide linker ("FL") of from 3 to 8 amino acids in length and consisting of glycine, and/or serine residues in sequence between the furin cleavage site and the functional PE Domain III of the improved PE. Accordingly, the short linker consists of glycine, and/or serine residues. In some embodiments, the linker is a peptide of the formula: $(Xaa1)_n$, wherein each Xaa1 is selected independently from glycine and serine and n is from 3 to 8. The improved PE molecules of the invention retain high cytotoxic activity with the removal of B cell epitopes. Surprisingly, the inclusion of the short flexible linker improves the cytotoxicity of the molecule without substantially altering cleavage of the molecule by furin. The improved PE molecules are exemplified by particular embodiments of the invention referred to here as (LR/FL/8X, SEQ ID NO:4) and LR/FL/8M (SEQ ID NO:5). In addition, there are embodiments, wherein the PE molecules have one or more mutations in their functional domain III as found in SEQ ID NO:4 or 5 as compared to the functional domain of the PE of SEQ ID NO:1. In further embodiments, there are additional substitutions in one or more residues corresponding to 609-613 of SEQ ID NO:1 are contemplated which also have an endoplasmic reticulum retention function of the native sequence. In still further embodiments, the PE Domain II furin cleavage site is modified or substituted by another furin cleavage site.

In some embodiments further as consistent with any of the above, the PE comprises a functional domain III which has one or more mutations to the functional domain of a PE toxin of SEQ ID NO:2 (positions 12 to 230) or selected from the following table which remove one or more epitopes of PE Domain III:

TABLE 2

| Epitope Removed | Mutations |
|---|---|
| 2 | R467A |
| 4 | R432G, D406A |
| 5 | R490A |
| 6 | E548A, R513A |
| 7 | K590S, Q592A |

*Epitopes are described, e.g., in Onda, et al., Proc Natl Acad Sci USA. 2008 105(32): 11311-6 and in WO 2007/016150.

In a related aspect, the invention provides RITs ("RITs of the invention") which are chimeric molecules comprising (a) a mesothelin targeting moiety conjugated or fused to (b) a modified Pseudomonas exotoxin A ("PE") as provided above. In some embodiments, the moiety is an antibody selected from the group consisting of an scFv, a dsFv, a Fab, a single domain antibody and a F(ab')$_2$, or a polypeptide comprising the CDRs of the antibody. SS1 and MORab-009 are preferred targeting moieties. In addition, the anti-mesothelin antibody can comprise a variable heavy ("$V_H$") chain and a variable light ("$V_L$") chain, which $V_H$ and $V_L$ chains each have a first, a second and a third complementarity-determining region ("CDR"), wherein the first CDR ("CDR1"), the second CDR ("CDR2"), and third CDR ("CDR3"), respectively, of said heavy chain have the amino acid residue sequence shown for CDR1 (GYTMN; SEQ ID NO:51), CDR2 (LITPYNGASSYNQKFRG; SEQ ID NO:52), and CDR3 (GGYDGRGFDY; SEQ ID NO:53), and wherein CDRs 1, 2 and 3 respectively, of said $V_L$ chain, have the amino acid residue sequence shown for CDR1 (SASSS-VSYMH; SEQ ID NO:54), CDR2 (DTSKLAS; SEQ ID NO:55), and CDR3 (QQWSGYPLT; SEQ ID NO:56). In some embodiments, the CDR3 of the light chain is modified and has the sequence QQWSGHPLT (SEQ ID NO:57), QQWSGHPLT (SEQ ID NO:58), QQWSAHPLT (SEQ ID NO:59), QQWSQIPLT (SEQ ID NO:60), QQWGFNPLT (SEQ ID NO:61), QQWGTNPLT (SEQ ID NO:62), QQWGSHPLT (SEQ ID NO:63), QQWGDFPLT (SEQ ID NO:64), QQWGDHPLT (SEQ ID NO:65), QQWSAHPLT (SEQ ID NO:66), or QQWSGYPTT (SEQ ID NO:67). In some further embodiments, the anti-mesothelin antibody is a scFv, dsFv, a Fab, or a F(ab')$_2$. In still some further embodiments, the anti-mesothelin antibody to be used in the RIT comprises an amino acid substitution of at least one amino acid in a CDR selected from the group consisting of $V_L$ CDR1, $V_L$ CDR2, $V_H$ CDR1, and $V_H$ CDR2, said amino acid being encoded by a codon that comprises a nucleotide belonging to a hot spot motif selected from AGY or RGYW, where R is A or G, Y is C or T and W is A or T.

In a further aspect, the invention provides pharmaceutical compositions comprising
(a) RIT of the invention as provided above and (b) a pharmaceutically acceptable carrier.

In a related aspect, the invention provides isolated nucleic acids encoding a modified Pseudomonas exotoxin A ("PE") FL or a RIT described above. In some embodiments, the nucleic acid further encodes all or a fragment (a variable light or heavy chain or CDR) of the mesothelin targeting antibody.

Accordingly, in a first group of embodiments, the invention provides isolated, modified Pseudomonas exotoxin As ("PE"s), comprising a continuous polypeptide sequence of the following formula: FCS-FL-PE functional domain III or L1-FCS-FL-PE functional Domain III, where L1 consists of a continuous peptide sequence of from 1 to 10 amino acid residues in length; FCS represents the furin cleavage site or sequence (e.g., RHRQPRGWEQL; SEQ ID NO:17), or another sequence which is cleavable by furin; and FL represents a flexible linker peptide sequence consisting of from 3 to 8 amino acid residues independently selected from glycine and serine; and PE functional domain III comprises residues 395-613 of SEQ ID NO:1, optionally comprising (i) substitutions in one or more residues corresponding to 609-613 of SEQ ID NO:1, (ii) a substitution of glycine, alanine, valine, leucine, or isoleucine for arginine at a position corresponding to position 490 of SEQ ID NO:1, (iii) a substitution of one or more residues corresponding to residues of SEQ ID NO:1, which residues of SEQ ID NO:1 maintain immunogenicity of a epitope or subepitope of PE domain III, or (iv) a combination of any of (i)-(iii). In preferred embodiments, the PE functional domain is the PE functional domain of LR/FL/8X (SEQ ID NO:4) or of LR/GGS/8M (SEQ ID NO:3).

In a further group of embodiments, the invention provides chimeric molecules or RITs comprising (a) a ligand or targeting moiety, which ligand specifically binds to mesothelin on a cell surface, conjugated or fused to (b) a modified Pseudomonas exotoxin A (PE) as described above. In some embodiments, the ligand is an antibody or fragment thereof which retains antigen recognition capability. In preferred embodiments, the antibodies are derived from an SS1 parent antibody. Preferably, the RIT is SS1-LR/GGS/8X which have a GGS FL inserted between the FCS and functional domain III. These RITs accordingly can comprise a SS1 variable light chain of SEQ ID NO: 6 and a SS1 variable heavy chain recombinant immunotoxin sequence of SEQ ID NO:8 or of SEQ ID NO:9 wherein the SS1 variable light and heavy chains form a disulfide stabilized antibody.

In yet a further group of embodiments, the invention provides therapeutic methods of killing target cells or inhibiting the growth of target cells which express or overexpress mesothelin on the cell exterior. The methods comprise contacting the cells with the RITs of the invention. Mesothelin is a differentiation antigen present on the surface of ovarian cancers, mesotheliomas and several other types of human cancers. The RITs of the invention can be used, for instance, in vitro or in vivo to kill or to inhibit the growth of cancers of the ovary, stomach, squamous cells, mesotheliomas and other malignant cells expressing mesothelin. Methods of treating patients having these conditions and in need of such treatment by the RITs of the invention are contemplated.

In yet a further group of embodiments, the invention provides nucleic acids encoding the mutated PEs and the RITs described above.

In some embodiments of any of the above the flexible linker is GGS or GGSGGS (SEQ ID NO:18).

In still other further embodiments, the antibody is selected from the group consisting of an scFv, a dsFv, a Fab, a single domain antibody and a F(ab')$_2$. In some further embodiments of the above, the antibody is SS1 or a reengineered SS1 (an scFv, a dsFv, a Fab, a single domain antibody, or a F(ab')$_2$ of the SS1 antibody, or fragment(s) providing the CDR portions of the SS1 antibody). In some embodiments, the CDRs of the antibody are used as the targeting moiety. In some embodiments, the antibody is human or humanized. In some embodiments, the modified PE is LR/GGS/8M (SEQ ID NO:3) or LR/(Xaa1)$_n$/8X (SEQ ID NO:4) or LR/(Xaa1)$_n$/8M (SEQ ID NO:5). In some further embodiments, the chimeric molecule is SS1-LR/GGS/8X (SEQ ID NOS:6 and 7) or SS1-LR/GGS/8M (SEQ ID NOS:6 and 8) wherein their respective targeting moieties comprise the $V_L$ and $V_H$ portions of the SS1 antibody.

Further embodiments will be apparent to those of ordinary skill and are described herein.

Accordingly, in some embodiments, the invention provides a chimeric molecule comprising an anti-mesothelin antibody fragment directly joined in sequence to a first peptide linker of from 3 to 8 amino acids in length which is directly joined in sequence to the furin polypeptide cleavage site RHRQPRGWEQL (SEQ ID NO:17) which is directly joined in sequence to a second peptide linker consisting of from 3 to 6 amino acids selected from Gly and Ser and which is directly joined in sequence to the N-terminal amino acid of a functional Domain III of *Pseudomonas* exotoxin A. In some further embodiments, the functional domain is Domain III of LR or LR/8M and the antibody fragment is the dsFv of SS1-LR. In some embodiments, wherein the first peptide linker (L1) is directly joined in sequence to the carboxy terminus of the VH portion of the dsFv. Pharmaceutical compositions of the chimeric molecules are also provided as well as there use in a method of treating a cancer which overexpresses mesothelin in a subject in need thereof. In further embodiments, the cancer is a lung adenocarcinoma, an ovarian carcinoma, a mesothelioma, or an epidermoid carcinoma.

BRIEF DESCRIPTION OF THE DRAWINGS

FIG. 1. Recombinant immunotoxins. (A) The recombinant immunotoxin SS1P consists of the disulfide-stabilized (ds) heavy (VH) and light (VL) polypeptide chains of the variable fragment (Fv) from the anti-mesothelin monoclonal antibody SS1 coupled to a 38-kDa fragment of *Pseudomonas* exotoxin A (PE38) via a short peptide linker (ASGG; SEQ ID NO:19) from the heavy chain. PE38 is composed of domain II, domain III, and a fragment of domain Ib from native *Pseudomonas* exotoxin A. Domain II includes a solvent-exposed loop, bounded by cysteines that form a disulfide bond, which contains a furin protease cleavage site (RHRQPRGWEQL; SEQ ID NO:17). (B) The lysosomal degradation resistant variant of SS1P, SS1-LR, lacks domain Ib and domain II of PE, except for an 11-residue stretch containing the furin cleavage site from domain II. Various constructs were created with mutations (underlined) around the furin cleavage site of SS1-LR (SEQ ID NOS:20-24).

FIG. 9. Summary of cytotoxicity of SS1-LR/GGS/8M on patient cells. Relative viability vs. treatment. Cells cultured from the pleural fluid or ascites of patients with mesothelioma were plated with increasing concentrations of SS (white bar) or SS1-LR/GGS/8M (grey bar). After 4 days, cells were fixed and stained with crystal violet to detect intact cells. The resulting absorbance at 595 nm was normalized against an untreated control. The mean values and standard errors from three replicates are plotted. Asterisks indicate significant differences of p<0.01 (), or p<0.001 (*).

DETAILED DESCRIPTION OF THE INVENTION

Figure 2:
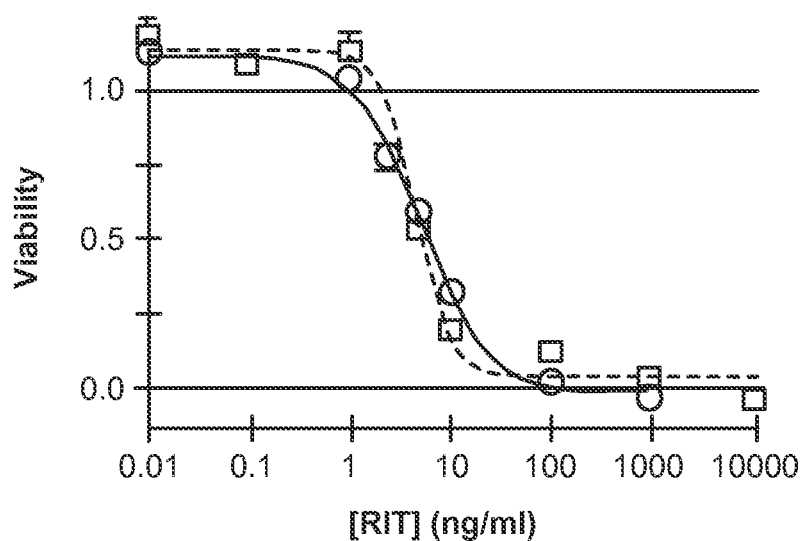
FIG. 2. Cytotoxicity of SS1-LR on mesothelin-positive cell lines. Cell lines L55, NCI-H322M, HAY, KB31, M30, A431/K5, OVCAR-8, and A1847 were incubated with increasing concentrations of SS1P (open circles, solid line) or SS1-LR (open squares, dashed line). After 3 days cell viability was evaluated with a colorimetric WST-8 assay, and normalized between untreated and cyclohexamide-treated controls. The mean values and standard errors from six replicates are plotted. SS1-LR comprises the disulfide stabilized SS1 $V_L$ polypeptide chain of SEQ ID NO:6 and SS1 $V_H$-PE polypeptide chain of SEQ ID NO: 7.
Figure 2:
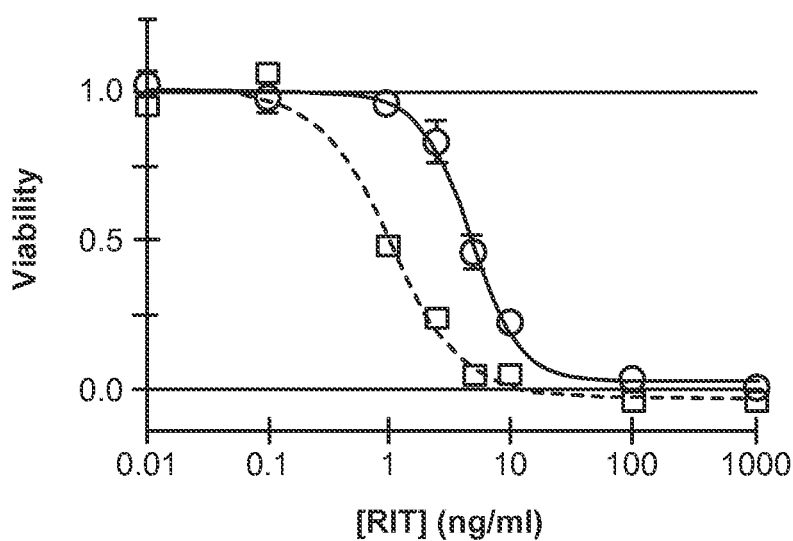
Figure 2:
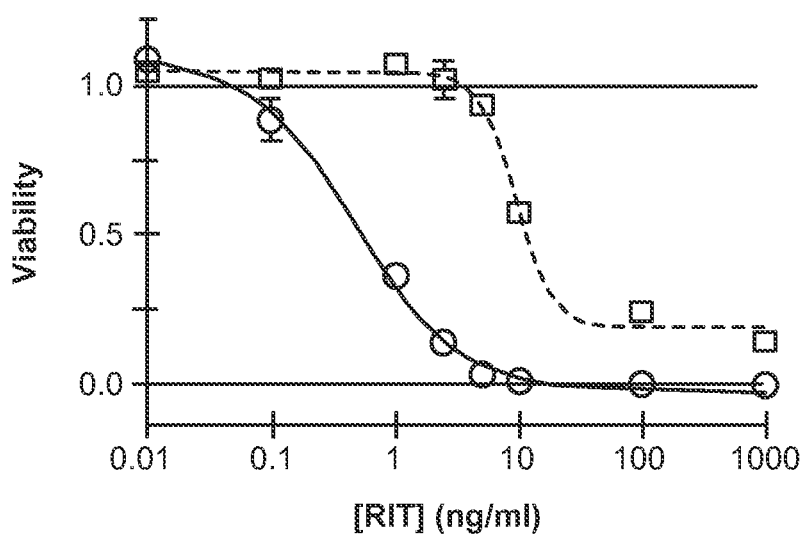
Figure 2:
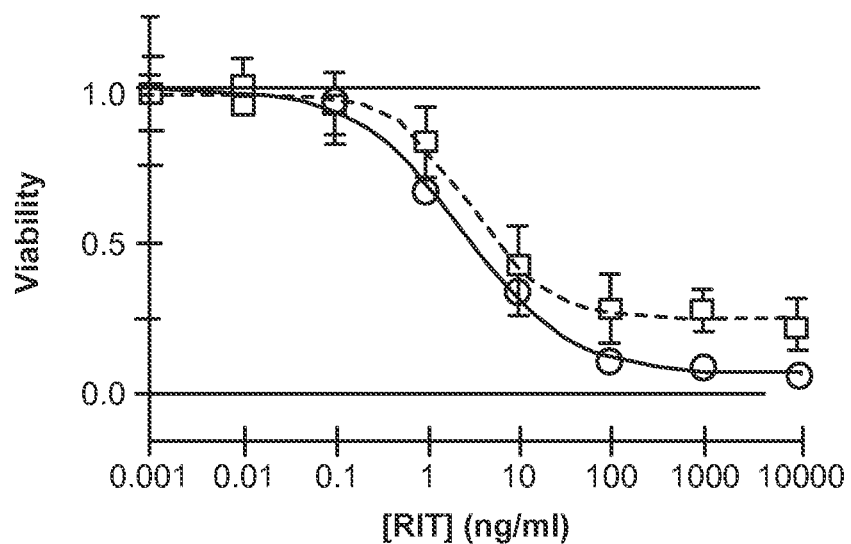
Figure 2:
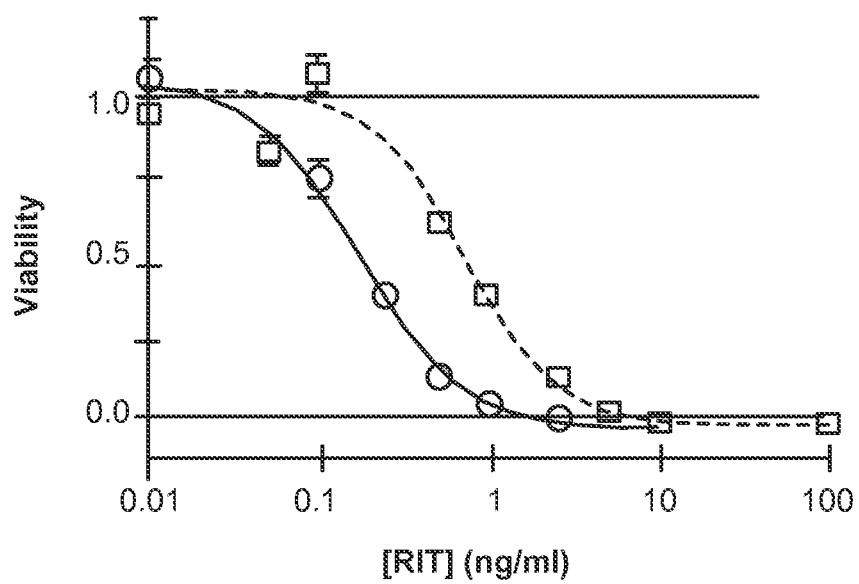
Figure 2:
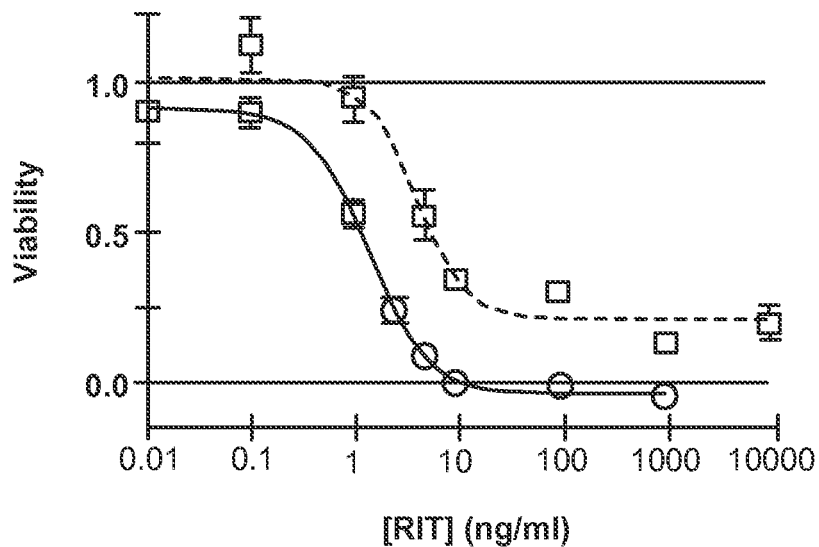
Figure 2:
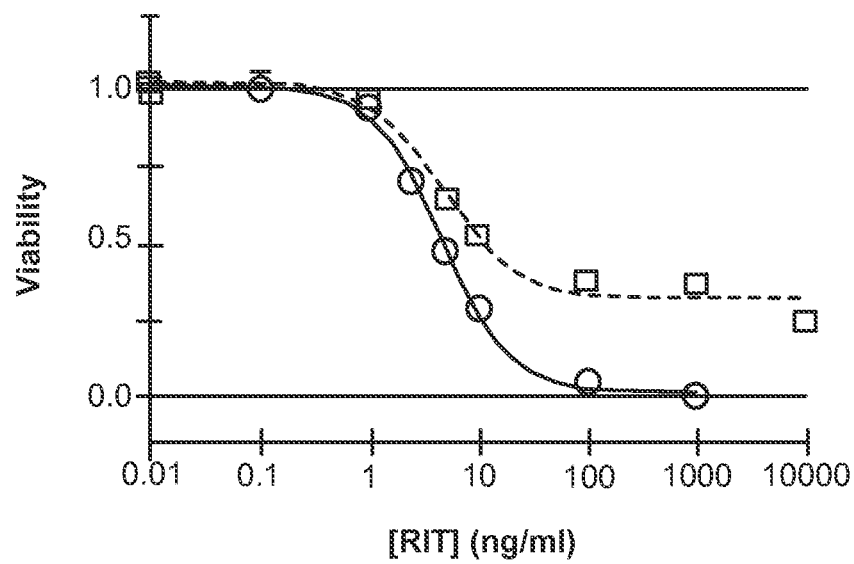
Figure 3:
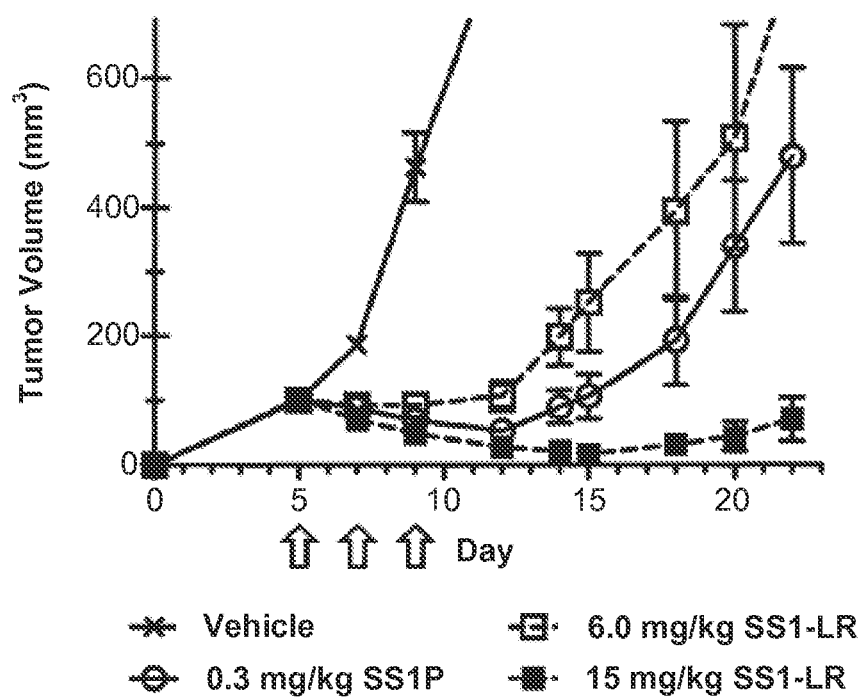
FIG. 3. High doses of SS1-LR have potent anti-tumor activity. Nude mice with A431/K5 xenograft tumors were intravenously treated on days 5, 7, and 9 post implantation with RIT buffer (0.2% HSA in PBS; crosses, solid line), 0.3 mg/kg SS1P (open circles, solid line), or SS1-LR at doses of 6 (open squares, dashed line) or 15 (filled squares, dashed line) mg/kg. Arrows indicate days when treatment was administered. Tumor size was measured over the course of 22 days. Points represent the mean tumor size of all mice in the treatment group (n=6). Error bars indicate the standard error of each mean value.
Figure 4:
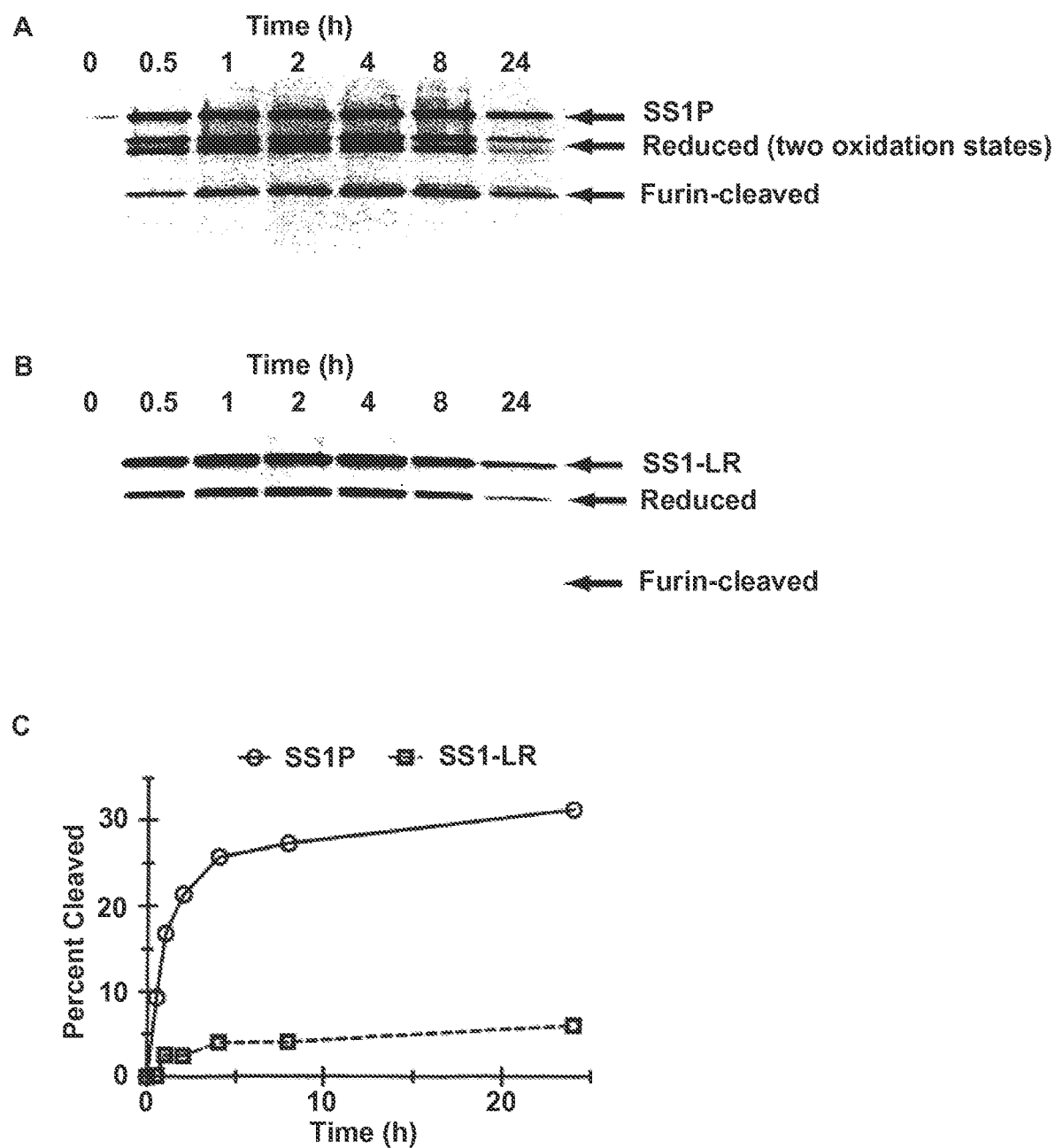
FIG. 4. Internalized immunotoxin processing. A431/K5 cells were incubated continuously with (A) SS1P or (B) SS1-LR, lysed at various time points from 0 to 24 hours, and analyzed by non-reducing SDS-PAGE Western blot with an anti-PE antibody. Full-length, reduced, and furin-cleaved bands are indicated. (C) The intensity of the furin-cleaved band relative to the total intensity of all bands at each time point is shown for SS1P (open circles, solid line) and SS1-LR (open squares, dashed line).
Figure 5:
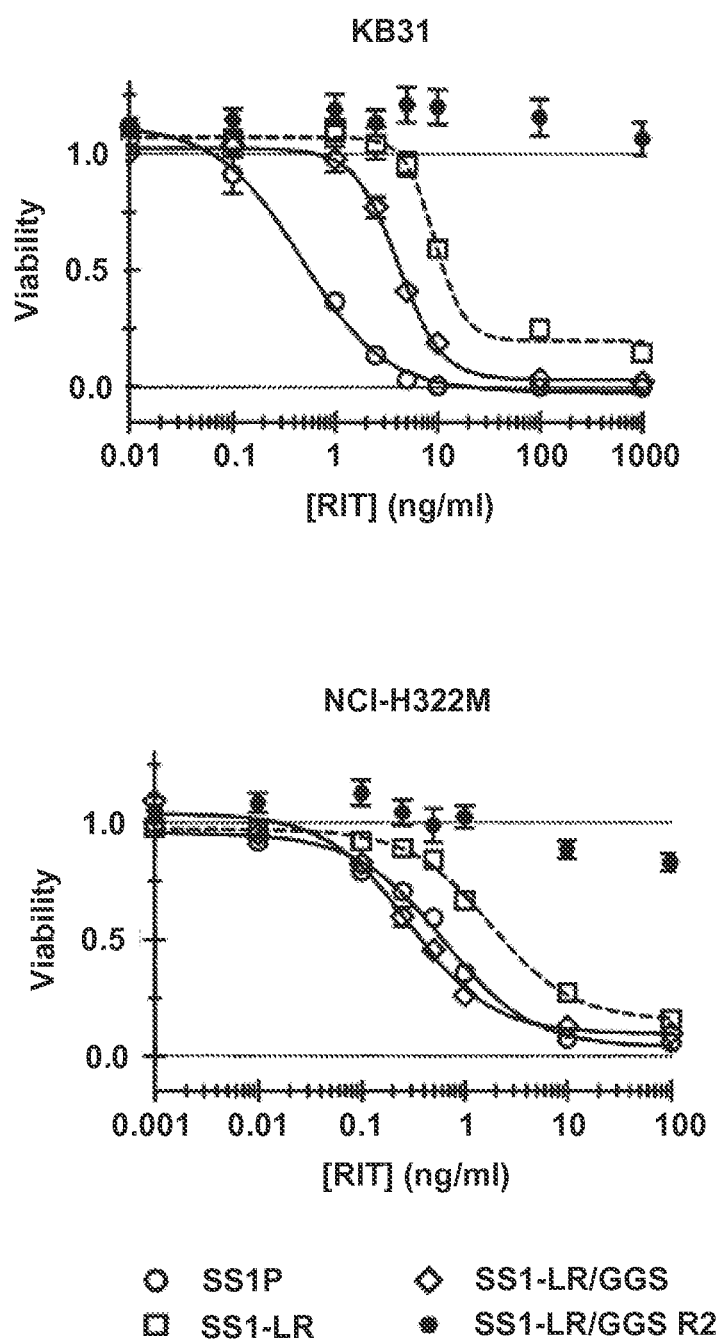
FIG. 5. Addition of a flexible linker enhances cytotoxicity of SS1-LR. Cell lines (A)KB31 and (8) NCI-H322M were incubated with increasing concentrations of SS1P (open circles, solid line), SS1-LR (open squares, dashed line), SS1-LR/GGS (open diamonds, solid line), or SS1-LR/GGS R279G (filled hexagons, no line). After 3 days cell viability was evaluated with acolorimetric WST-8 assay, and normalized between untreated and cyclohexamide-treated controls. The mean values and standard errors from six replicates are plotted.

The present invention provides less toxic and less immunogenic variant of anti-mesothelin RITs based upon the PE-based anti-mesothelin RIT SS1P. Our initial evaluation of SS1-LR, generated on the basis of previous work with the PE-based anti-CD22 RIT HA22-LR (Weldon et al., Blood 113(6):3792-3800(2009)), showed highly variable activity in a selection of mesothelin-expressing cell lines in vitro. In a mouse A431/K5 xenograft tumor assay, SS1-LR (SEQ ID NOS:6 and 7) was less active than SS1P, but SS1-LR could be administered at much higher doses to achieve significant tumor regression. While exploring reasons for its highly variable activity relative to SS1P, we studied the internalization and processing of SS1-LR and found that the proportion of furin-cleaved SS1-LR was much lower than that of SS1P. This suggested that decreased furin cleavage could be limiting the activity of SS1-LR, and we designed and produced several mutants to test this hypothesis. The addition of a short Gly-Gly-Ser linker after the furin cleavage site enhanced the activity of SS1-LR on cell lines, but surprisingly the enhanced cytotoxicity did not correspond to enhanced furin cleavage. The instant invention relates to this surprising discovery of the importance of a short, flexible linker to the cytotoxicity of an anti-mesothelin RIT construct independent of any effect on cleavage of PE by furin. In further work, 8 point mutations that have been shown to reduce the immunogenicity of PE into SS1-LR/GGS were incorporated and then tested the molecule on primary malignant cells from patients with mesothelioma. The final molecule, SS1-LR/GGS/8M (SEQ ID NOS:6 and 8) demonstrated cytotoxicity similar to SS1P. In addition, the RITs according to the invention can provide a markedly reduced non-specific toxicity (e.g., capillary leak syndrome) in mammals.

About a 20-fold difference in anti-tumor effect between SS1-LR and SS1P was observed using an in vivo A4311K5 xenograft tumor mouse model. This difference cannot entirely be attributed to cytotoxicity, since the in vitro cytotoxicity data indicate a 4-fold decrease in cytotoxicity on A431/K5 cells. Instead, the remainder of this difference is likely due to the pharmacokinetic properties of SS1-LR in mice. We have shown previously that HA22-LR has a nearly 2-fold shorter serum half-life in mice than HA22 (7.8 versus 14.6 minutes, respectively), and postulated that the difference was due to increased renal filtration of the smaller LR molecule (Weldon J E, Blood., 113(16):3792-800 (2009)). By examining the area under the decay curve, this difference in half-life suggests about a 4-fold difference in available protein over the course of an hour. Thus, the difference in activity in vivo can be attributed to both decreased cytotoxicity and a shorter half-life.

Although SS1-LR demonstrated lower anti-tumor activity than SS1P in vivo, its nonspecific toxicity was also greatly reduced in the mice. We took advantage of this property to dramatically increase the dose of SS1-LR over SS1P (50-fold) in the xenograft tumor assay, leading to a greatly enhanced anti-tumor effect. Previous experiments have variously shown that the single-dose intravenous LD50 of SS1P is 1.0 mg/kg in Balb/C mice (Filpula D et al., Bioconjug Chem., 18(3):773-84 (2007)) and 0.75 mg/kg in NIH Swiss mice (Onda M et al., Cancer Res., 61(13):5070-7 (2001)). Using a QODx3 dosing schedule similar to the clinical schedule, mice have tolerated a maximum dose of 0.3 mg/kg SS1P (unpublished observations). SS1-LR, however, was administered QODx3 in the A431/K5 xenograft anti-tumor experiment at a dose of 15 mg/kg without ill effect. Previously, a single intravenous dose of HA22-LR at 20 mg/kg showed no toxicity to mice (Weldon J E, Blood., 113(16): 3792-800 (2009)), and we have given single doses of HA22•LR as high as 45 mg/kg to mice without causing death (unpublished observations). Although no LR molecule has been tested clinically, this effect suggests that the LR variant RITs may have decreased toxicity in human patients, which could prevent dose-limiting toxicities and allow higher doses to be administered.

Although SS1-LR was effective in vitro and in vivo, we were concerned by the generally decreased activity relative to SS1P. One possible explanation for this disparity is a difference in the intracellular intoxication pathway. The LR variant of PE38 contains extensive deletions in domain II and Ib of PE, and these deletions might have negatively affected the ability of PE to traffic to the cytosol. Interestingly, our initial experiments to detect full-length and processed PE in lysates of cells treated with SS1P and SS1-LR showed a dramatic difference in the amount of furin-processed RIT. A large fraction of the total RIT in SS1P-treated cells was processed, but only a small fraction of the total RIT in SS1-LR-treated cells. This result suggested that poor furin cleavage might be limiting the activity of SS1-LR, and we set out to improve this step of the PE intoxication pathway.

Our efforts to enhance the cytotoxicity of SS1-LR by increasing the accessibility of the furin cleavage site produced a more active RIT, but we could not demonstrate enhanced furin cleavage. The addition of a short Gly-Gly-Ser linker (SS1-LR/GGS, FIG. 1B), a longer linker (SS1-LR/GGSx2, FIG. 1B), or a repeat of the furin site flanked by short Gly-Gly-Ser linkers (SS1-LR/2xFurin, FIG. 1B) all granted a modest cytotoxicity increase. None of these molecules, however, enhanced the proportion of furin-cleaved SS1-LR in treated A431/K5 cells or increased the rate of furin cleavage in vitro. We concluded that the addition of a linker must enhance cytotoxicity through another mechanism, perhaps related to the intracellular trafficking of the molecule in the tested cells.

These experiments also demonstrated the absolute necessity of furin cleavage for retaining the cytotoxicity of SS1P. A point mutation in SS1-LR/GGS that changed an arginine essential for cleavage to glycine (SS1-LR/GGS R279G, FIG. 1B) produced a protein that was not cleaved by furin. This RIT showed no activity on both NCI-H322M and KB31 cells. The necessity of furin cleavage in the PE intoxication pathway has recently been questioned (Morlon-Guyot J et al., *Infect Immun.*, 77(7):3090-9 (2009)), but much evidence exists that furin performs an important role during intoxication (Ornatowski W et al., *J Clin Invest.*, 117(11):3489-97 (2007); Shiryaev S A et al., *J Biol. Chem.*, 282(29):20847-53 (2007); Sarac M S et al., *Infect Immun.*, 70(12):7136-9 (2002); Chiron M F, Fryling C M, and FitzGerald D, *J Biol. Chem.*, 272(50):31707-11 (1997); Gu M et al., *Infect Immun.*, 64(2):524-7 (1996); Inocencio N M, Moehring J M, and Moehring T J, *J Biol. Chem.*, 269(50):31831-5 (1994); Moehring J M et al., *J Biol. Chem.*, 268(4):2590-4 (1993)). In the case presented here, PE intoxication fails without containing a site suitable for furin processing. Research is ongoing to explore the relationship between furin cleavage and cytotoxicity.

A separate line of research in our laboratory has recently produced a variant of HA22, HA22-LR-8M, which has extremely low immunogenicity due to the elimination of B cell epitopes (Onda M et al., Submitted for publication to *PNAS.*). HA22-LR-8M contains the same deletions as the LR variant of PE, but also incorporates eight point mutations in domain" of PE. These mutations were placed into SS1P to generate SS1-LR/GGS/8M. The only differences between HA22-LR-8M and SS1-LR/GGS/8M are the antibody Fv and the GGS linker after the furin cleavage site. Since the vast bulk of the immune response to RITs is directed at PE, SS1-LR/GGS/8M should exhibit similarly reduced immunogenicity.

The cytotoxicity of SS1-LR/GGS/8M was compared to SS1P on primary malignant cells from patients with mesothelioma, and the results showed that SS1-LR/GGS/8M had cytotoxicity comparable to or better than SS1P. In addition to good activity, SS1-LR/GGS/8M has potential advantages over SS1P that include decreased nonspecific toxicity and low immunogenicity. The experiments described here suggest that SS1-LR/GGS/8M would be an excellent candidate for the clinic due to its low immunogenicity, low nonspecific toxicity, and good cytotoxicity.

Definitions

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

Native *Pseudomonas* exotoxin A ("PE") is an extremely active monomeric protein (molecular weight 66 kD), secreted by *Pseudomonas aeruginosa*, which inhibits protein synthesis in eukaryotic cells. The native PE sequence is set forth in SEQ ID NO:1 of U.S. Pat. No. 5,602,095, incorporated herein by reference. The method of action is inactivation of elongation factor 2 (EF-2) by ADP-ribosylation. The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The original structure of PE classifies domain III as residues 405-613, not 400-613. Allured V S, Collier R J, Carroll S F & McKay D B, *Proc Natl Acad Sci USA* 83, 1320-1324 (1986). The function of domain Ib (amino acids 365-399) remains undefined, although a large part of it, amino acids 365-380, can be deleted without loss of cytotoxicity. See Siegall, et al., J Biol Chem 264:14256-61 (1989). Numerous such modifications are known in the art and include, but are not limited to, elimination of domain Ia, various amino acid deletions in domains Ib, II and III, single amino acid substitutions and the addition of one or more sequences at the carboxyl terminus such as KDEL (SEQ ID NO:16) and REDL (SEQ ID NO:26). See Siegall, et al., *J. Biol. Chem.* 264:14256-14261 (1989). The immunotoxins of the present invention are capable of translocation and EF-2 ribosylation in a targeted cell.

Mutations of PE are described herein by reference to the amino acid residue present at a particular position of the 613-amino acid sequence of native PE (SEQ ID NO:1), followed by the amino acid with which that residue has been replaced in the particular mutation under discussion. Thus, for example, the term "R490A" indicates that the "R" (arginine, in standard single letter code) at position 490 of the referenced molecule is replaced by an "A" (alanine, in standard single letter code), while "K590Q" indicates that the lysine normally present at position 590 has been replaced with a glutamine. The standard single letter code for common amino acids is set forth below.

The term "PE functional domain III" or "functional PE Domain III" refers to residues 395-613 of native PE (the native sequence is SEQ ID NO:1). Although the structural boundaries of domain III have been set at residues 405-613, functional analyses have shown that domain III requires a segment of domain Ib to retain ADP-ribosylation activity (Hwang, J. et al., *Cell,* 48:129-136 (1987); Siegall, C. B. et al., *J Biol Chem,* 264:14256-14261 (1989)). The PE functional domain III is thus defined by residues 395-613 of PE (Kihara, A. and Pastan, I., *Bioconjug Chem,* 5:532-538 (1994)). Herein, the functional PE Domain III sequence includes the optional modifications to reduce antigenicity and optional alternative endoplasmic reticulum retention sequences.

The terminal residues of PE Domain III, REDLK (SEQ ID NO:15) can be varied in ways that would increase the cytotoxicity of the resulting RITs according to this invention. For example, immunotoxins made with mutated PEs ending in the sequences KDEL (SEQ ID NO:16), REEL (SEQ ID NO:27) or RDEL (SEQ ID NO:28) can be much more cytotoxic to target cells than immunotoxins made with PE38 bearing the native terminal sequence. See, Kreitman and Pastan, *Biochem J*, 307(Pt 1):29-37 (1995). Repeats of these sequences can also be used in the present RITs. See, e.g., U.S. Pat. Nos. 5,854,044; 5,821,238; and 5,602,095 and International Publication WO 99/51643. While PEs terminating in KDEL (SEQ ID NO:16) are useful for in vitro purposes, they may have more non-specific toxicity in animals and are less preferred for in vivo use.

The term "mesothelin" refers to a protein and fragments thereof present on the surface of some human cells and bound by, for example, the K1 antibody. Nucleic acid and amino acid sequences of mesothelin are set forth in, for example, PCT published application WO 97/25,068 and U.S. Pat. Nos. 6,083,502 and 6,153,430. See also, Chang, K. & Pastan, I., *Int. J. Cancer* 57:90 (1994); Chang, K. & Pastan, I., *Proc. Nat'l Acad. Sci. USA* 93:136 (1996); Brinkmann U., et al., *Int. J. Cancer* 71:638 (1997); Chowdhury, P. S., et al., *Mol. Immunol.* 34:9 (1997), and U.S. Pat. No. 6,809,184. Mesothelin is expressed as a precursor protein of approximately 69 kDa, that then is processed to release a 30 kDa protein, while leaving attached to the cell surface the 40 kDa glycosylphosphatidylinositol linked cell surface glycoprotein described in the Background. The 40 kDa glycoprotein is the one referred to by the term "mesothelin" herein. The nucleic acid and amino acid sequences of mesothelin have been recorded from several species, e.g., human (NM_005823.4→NP_005814.2; and NM_013404.3→NP_037536.2), mouse (NM_018857.1→NP_061345.1), rat (NM_031658.1→NP_113846.1), bovine (NM_001100374.1→NP_001093844).

For convenience of reference, as used herein, the term "antibody" includes whole (sometimes referred to herein as "intact") antibodies, antibody fragments that retain antigen recognition and binding capability, whether produced by the modification of whole antibodies or synthesized de novo using recombinant DNA methodologies, monoclonal antibodies, polyclonal antibodies, and antibody mimics, unless otherwise required by context. The antibody may be an IgM, IgG (e.g. IgG$_1$, IgG$_2$, IgG$_3$ or IgG$_4$), IgD, IgA or IgE.

Sequences of the constant regions of the IgG subclasses have been well known in the art for years (e.g., Honjo et al., *Cell*, 18:559-68 (1979); Tucker et al., *Science*, 206:1303-6 (1979); Yamawaki et al., *Nature* 283:786-9 (1980); Ellison et al., *Nucl Acids Res* 10:4071-9 (1982); Ellison et al., *DNA* 1:11-8 (1981); Ellison and Hood, *Proc Natl Acad Sci USA* 79:1984-8 (1982)). Since the CDRs of the variable regions determine antibody specificity, CDRs or Fvs of antibodies against a target cell surface antigen can be grafted or engineered into an antibody of choice to confer specificity for the target cell surface antigen upon that antibody. For example, CDRs of an antibody against a target cell surface antigen can be grafted onto a human antibody framework of known three dimensional structure (see, e.g., WO98/45322; WO 87/02671; U.S. Pat. Nos. 5,859,205; 5,585,089; and 4,816,567; EP Patent Application 0173494; Jones, et al. *Nature* 321:522 (1986); Verhoeyen, et al., *Science* 239:1534 (1988), Riechmann, et al. *Nature* 332:323 (1988); and Winter & Milstein, Nature 349:293 (1991)) to form an antibody that will raise little or no immunogenic response when administered to a human. Alternatively, the constant regions of the antibodies can be engineered by replacing residues found in non-human animals, such as mice, with residues typically found in humans. Antibodies engineered in this way are referred to as "humanized antibodies" and are preferred, since they have a lower risk of inducing side effects and can remain in the circulation longer. Methods of humanizing antibodies are known in the art and are set forth in, for example, U.S. Pat. Nos. 6,180,377; 6,407,213; 5,693,762; 5,585,089; and 5,530,101.

The term "antibody fragments" means molecules that comprise a portion of an intact antibody, generally the antigen binding or variable region of the intact antibody. Examples of antibody fragments include Fab, Fab', F(ab')$_2$, and Fv fragments; single domain antibodies (see, e.g., Wesolowski, *Med Microbiol Immunol.* (2009) 198(3):157-74; Saerens, et al., *Curr Opin Pharmacol.* (2008) 8(5):600-8; Harmsen and de Haard, *Appl Microbiol Biotechnol.* (2007) 77(1):13-22); helix-stabilized antibodies (see, e.g., Arndt et al., *J Mol Biol* 312:221-228 (2001); diabodies (see below); single-chain antibody molecules ("scFvs," see, e.g., U.S. Pat. No. 5,888,773); disulfide stabilized antibodies ("dsFvs", see, e.g., U.S. Pat. No. 5,747,654 and 6,558,672), and domain antibodies ("dAbs," see, e.g., Holt et al., Trends Biotech 21(11):484-490 (2003), Ghahroudi et al., *FEBS Lett.* 414:521-526 (1997), Lauwereys et al., *EMBO J.* 17:3512-3520 (1998), Reiter et al., *J. Mol. Biol.* 290:685-698 (1999), Davies and Riechmann, Biotechnology, 13:475-479 (2001)).

The term "diabodies" refers to small antibody fragments with two antigen-binding sites, which fragments comprise a variable heavy domain ("V$_H$" or "VH") connected to a variable light domain ("V$_L$" or "VL") in the same polypeptide chain (V$_H$-V$_L$). By using a linker that is too short to allow pairing between the two domains on the same chain, the domains are forced to pair with the complementary domains of another chain and create two antigen-binding sites. Diabodies and their production are described more fully in, for example, EP 404,097; WO 93/11161; and Hollinger et al., *Proc. Natl. Acad. Sci. USA*, 90: 6444-6448 (1993).

The term "parental antibody" means any antibody of interest which is to be mutated or varied to obtain antibodies or fragments thereof which bind to the same epitope as the parental antibody, but with higher affinity.

A "targeting moiety" is the portion of an immunoconjugate intended to target the immunoconjugate to a cell of interest. Typically, the targeting moiety is an antibody, or a fragment of an antibody that retains antigen recognition capability, such as a scFv, a dsFv, an Fab, or an F(ab')$_2$.

A "toxic moiety" is the portion of a immunotoxin which renders the immunotoxin cytotoxic to cells of interest. With regard to the immunotoxins which are the subject of the present invention, the toxic moiety is a *Pseudomonas* exotoxin A which has been modified/mutated to reduce its non-specific cytotoxicity, as described in some detail below.

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs". The extent of the framework region and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "VH" refer to the variable region of an immunoglobulin heavy chain, including an Fv, scFv, dsFv or Fab. References to "$V_L$" or a "VL" refer to the variable region of an immunoglobulin light chain, including of an Fv, scFv, dsFv or Fab The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond.

The phrase "disulfide stabilized Fv" or "dsFv" refer to the variable region of an immunoglobulin in which there is a disulfide bond between the light chain and the heavy chain. In the context of this invention, the cysteines which form the disulfide bond are within the framework regions of the antibody chains and serve to stabilize the conformation of the antibody. Typically, the antibody is engineered to introduce cysteines in the framework region at positions where the substitution will not interfere with antigen binding.

The term "linker peptide" includes reference to a peptide within an antibody binding fragment (e.g., Fv fragment) which serves to indirectly bond the variable domain of the heavy chain to the variable domain of the light chain.

The term "hotspot" means a portion of a nucleotide sequence of a CDR or of a framework region of a variable domain which is a site of particularly high natural variation. Although CDRs are themselves considered to be regions of hypervariability, it has been learned that mutations are not evenly distributed throughout the CDRs. Particular sites, or hotspots, have been identified as these locations which undergo concentrated mutations. The hotspots are characterized by a number of structural features and sequences. These "hotspot motifs" can be used to identify hotspots. Two consensus sequences motifs which are especially well characterized are the tetranucleotide sequence RGYW and the serine sequence AGY, where R is A or G, Y is C or T, and W is A or T.

An antibody immunologically reactive with a particular antigen can be generated by recombinant methods such as selection of libraries of recombinant antibodies in phage or similar vectors, see, e.g., Huse, et al., *Science* 246:1275-1281 (1989); Ward, et al., *Nature* 341:544-546 (1989); and Vaughan, et al., *Nature Biotech.* 14:309-314 (1996), or by immunizing an animal with the antigen or with DNA encoding the antigen.

The term "effector moiety" means the portion of an immunoconjugate intended to have an effect on a cell targeted by the targeting moiety or to identify the presence of the immunoconjugate. In the context of the present invention, the effector moiety is a modified or mutated *Pseudomonas* exotoxin A.

The term "immunoconjugate" includes reference to a covalent linkage of an effector molecule to an antibody.

The terms "effective amount" or "amount effective to" or "therapeutically effective amount" includes reference to a dosage of a therapeutic agent sufficient to produce a desired result, such as inhibiting cell protein synthesis by at least 50%, or killing the cell.

In the context of the present invention, the toxin is a mutated *Pseudomonas* exotoxin A.

The term "contacting" includes reference to placement in direct physical association.

An "expression plasmid" comprises a nucleotide sequence encoding a molecule or interest, which is operably linked to a promoter.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table A:

TABLE A

Amino Acid Nomenclature

| Name | 3-letter | 1-letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table B each contain amino acids that are conservative substitutions for one another:

TABLE B

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, *Proteins: Structures and Molecular Properties*, W.H. Freeman and Company, New York (2nd Ed., 1992).

The terms "conjugating," "joining," "bonding" or "linking" refer to making two polypeptides into one contiguous polypeptide molecule. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, under expressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolumn* (*Proc. Nat'l Acad. Sci. USA* 82:2306-2309 (1985), or the ciliate *Macronucleus*, may be used when the nucleic acid is expressed in using the translational machinery of these organisms.

The phrase "fusing in frame" or refers to joining two or more nucleic acid sequences which encode polypeptides so that the joined nucleic acid sequence translates into a single chain protein ("fusion protein") which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, more preferably 65%, even more preferably 70%, still more preferably 75%, even more preferably 80%, and most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of a comparison peptide or coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (http://www.ncbi.nlm.nih.gov/). This algorithm involves first identifying high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that are invasive and/or able to undergo metastasis, i.e., a cancerous cell.

As used herein, "mammalian cells" includes reference to cells derived from mammals including humans, rats, mice, guinea pigs, chimpanzees, or macaques. The cells may be cultured in vivo or in vitro.

The term "selectively reactive" refers, with respect to an antigen, the preferential association of an antibody, in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive antibodies bind antigen, they may do so with low affinity. On the other hand, specific binding results in a much stronger association between the antibody and cells bearing the antigen than between the bound antibody and cells lacking the antigen. Specific binding typically results in greater than 5-fold, more preferably greater than 10-fold and most preferably greater than 100-fold increase in amount of bound antibody (per unit time) to a cell or tissue bearing the target antigen as compared to a cell or tissue lacking the target antigen. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. Preferably, the immunologically reactive conditions employed in the methods of the present invention are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The terms "patient," "subject," "individual" interchangeably refer to a mammal, for example, a human or a non-human primate, a domesticated mammal (e.g., a canine or feline), an agricultural mammal (e.g., a bovine, porcine, ovine, equine), a laboratory mammal (a mouse, rat, hamster, rabbit).

The term "co-administer" refers to the simultaneous presence of two active agents in the blood of an individual. Active agents that are co-administered can be concurrently or sequentially delivered.

As used herein, the terms "treating" and "treatment" refer to delaying the onset of, retarding or reversing the progress of, or alleviating or preventing either the disease or condition to which the term applies, or one or more symptoms of such disease or condition.

The terms "inhibiting," "reducing," "decreasing" with respect to tumor or cancer growth or progression refers to inhibiting the growth, spread, metastasis of a tumor or cancer in a subject by a measurable amount using any method known in the art. The growth, progression or spread of a tumor or cancer is inhibited, reduced or decreased if the tumor burden is at least about 10%, 20%, 30%, 50%, 80%, or 100% reduced in comparison to the tumor burden prior to the co-administration of a PE of the present invention, e.g., as part of a chimeric molecule. In some embodiments, the growth, progression or spread of a tumor or cancer is inhibited, reduced or decreased by at least about 1-fold, 2-fold, 3-fold, 4-fold, or more in comparison to the tumor burden prior to administration of the PE.

Components of the Recombinant Immunotoxins

A. Furin Cleavage Sites (FCS)

The furin cleavage site can be any polypeptide site cleavable by furin. As reported by Duckert et al., Protein Engineering, Design & Selection 17(1):107-112 (2004) (hereafter, "Duckert et al." and which is incorporated herein by reference in its entirety and particularly with regard to the furin cleavable sequences and motifs it discloses), furin is an enzyme in a "family of evolutionarily conserved dibasic- and monobasic-specific $CA2^+$-dependent serine proteases called substilisin/kexin-like proprotein convertases." Id., at p. 107. Furin, also known as "paired basic amino acid cleaving enzyme" or "PACE", is one of seven mammalian members of the family and is involved in processing several endogenous human proteins. See generally, e.g., Thomas G, *Nat Rev Mol Cell Biol*, (10):753-66 (2002). It is a membrane-associated protein found mainly in the trans-Golgi network. The sequence of human furin has been known since the early 1990s. See, e.g., Hatsuzawa, K. et al., *J Biol. Chem.*, 267:16094-16099 (1992); Molloy, S. et al., *J. Biol. Chem.*, 267:16396-16402 (1992).

The minimal cleavage site typically is, in the single letter code for amino acid residues, R-X-X-R (SEQ ID NO: 74), with cleavage occurring after the second "R". Duckert et al. summarizes the information available on the sequences of 38 proteins reported in the literature to have furin cleavage sites, including mammalian proteins, proteins of pathogenic bacteria, and viral proteins. It reports that 31, or 81%, of the cleavage motifs reviewed had the R-X-[R/K]-R consensus sequence, of which 11, or 29%, had R-X-R-R, and 20, or 52%, were R-X-K-R. Three of the cleavage motifs contained only the minimal cleavage sequence. Duckert et al. further aligned the motifs and identified the residues found at each position in each furin both for the cleavage motif itself and in the surrounding residues. FIG. 1A of Duckert et al. shows by relative size the residues most commonly found at each position. By convention, the residues surrounding the furin cleavage site are numbered from the scissile bond (which is typically indicated by the symbol "↓"). Counting toward the N terminus, the substrate residues are designated P1, P2, and so on, while counting towards the C-terminus, the residues are designated P1', P2', and so on. See, e.g., Rockwell, N. C., and J. W. Thorner, *Trends Biochem. Sci.*, 29:80-87 (2004); Thomas G., *Nat. Rev. Mol. Cell Biol.*, 3:753-766 (2002). Thus, following the convention, the following sequence can be used to align and number the residues of the minimal cleavage sequence and the surrounding residues:

P6-P5-P4-P3-P2-P1-P1'-P2'-P3'-P4'-P5', in which the minimal furin cleavage sequence is numbered as P4-P1. Duckert et al.'s alignment of 38 sequences cleaved by furin identifies the variations permitted depending on the residues present at various positions. For example, if the residue at P4 is not an R, that can be compensated for by having arginine or lysine residues at P2 and P6. Id., at p. 109.

In native PE, furin cleavage occurs between arginine 279 and glycine 280 in an arginine-rich loop located in domain II of the toxin. The native furin cleavage sequence in domain II of PE is set forth below (with numbers indicating the positions of the residues in the 613-amino acid native PE sequence), and aligned to show its numbering under the convention noted above:

274-  R  H  R  Q  P  R  G  W  E  Q  L  -284 (SEQ ID NO: 17)

P6-P5-P4-P3-P2-P1-P1'-P2'-P3'-P4'-P5'

In studies underlying the present invention, substitutions were made at positions P3 and P2 to form the following sequence, with the substitutions underlined:

274-  R  H  R  <u>S</u>  <u>K</u>  R  G  W  E  Q  L  -284 (SEQ ID NO: 29).

This sequence has showed a cleavage rate faster than that of the native sequence, and when used in an exemplar immunotoxin resulted in cytotoxicity to target cells approximately the same as that of the native sequence.

Based on this and our previous studies, the furin cleavage sequence used to attach the targeting molecule to PE domain III can be the minimal furin cleavage sequence, R-X-X—R, or any of the other furin cleavage sequences known in the art or permitted by FIG. 1A of Duckert et al., with the proviso that, if there is a residue present at the position identified as P2', it should be tryptophan or, if not tryptophan, should not be valine or alanine. For example, in some embodiments, the sequence can be RKKR (SEQ ID NO:30), RRRR (SEQ ID NO:31), RKAR (SEQ ID NO:32), SRVARS (SEQ ID NO:33), TSSRKRRFW (SEQ ID NO:34), or ASRRKARSW (SEQ ID NO:35).

As noted in Duckert et al., a less favorable residue than R (primarily valine) can be used position P4 if compensated for by arginine or lysine residues at positions P2 and P6, so that at least two of the three residues at P2, P4 and P6 are basic. Thus, in some embodiments, the furin cleavable sequence is RRVKKRFW (SEQ ID NO:36), RNVVRRDW (SEQ ID NO:37), or TRAVRRRSW (SEQ ID NO:38). The residue at position P1 can be the arginine present in the native sequence, or lysine. Thus, a lysine can be substituted for the arginine at position P1 in, for example, any the sequences set forth above.

In some embodiments, the sequence of the furin cleavable sequence follows the sequence of the furin cleavage sequence of PE: R-H-R-Q-P-R-G-W-E-Q-L (SEQ ID NO: 17) or a truncated version of the native sequence, so long as it contains the minimal furin cleavage sequence and is cleavable by furin. Thus, in some embodiments, the furin cleavable sequence can be R-Q-P-R (SEQ ID NO:39), R-H-R-Q-P-R-G-W (SEQ ID NO:40), R-H-R-Q-P-R-G-W-E (SEQ ID NO:41), H-R-Q-P-R-G-W-E-Q (SEQ ID NO:42), or R-Q-P-R-G-W-E (SEQ ID NO:43). In some embodiments, the sequence is R-H-R-S-K-R-G-W-E-Q-L (SEQ ID NO:29) or a truncated version of this sequence, so long as it contains the minimal furin cleavage sequence and is cleavable by furin. Thus, in some embodiments, the furin cleavable sequence can be R-S-K-R (SEQ ID NO:44), R-H-R-S-K-R-G-W (SEQ ID NO:45), H-R-S-K-R-G-W-E (SEQ ID NO:46), R-S-K-R-G-W-E-Q-L (SEQ ID NO:47), H-R-S-K-R-G-W-E-Q-L (SEQ ID NO:48), or R-H-R-S-K-R (SEQ ID NO:49). Any particular furin cleavable sequence can be readily tested by making it into an immunotoxin with the antibody used in SS1-LR and testing the resulting immunotoxin in vitro on a mesothelin+ cell line.

Whether or not any particular sequence is cleavable by furin can be determined by methods known in the art. For example, whether or not a sequence is cleavable by furin can be tested by incubating the sequence with furin in furin buffer (0.2 M NaOAc (pH 5.5), 5 mM $CaCl_2$) at a 1:10 enzyme:substrate molar ratio at 25° C. for 16 hours. These conditions have previously been established as optimal for furin cleavage of PE. Preferably, the furin used is human furin. Recombinant truncated human furin is commercially available, for example, from New England Biolabs (Beverly, Mass.). See also, Bravo et al., *J Biol Chem*, 269(14):25830-25837 (1994). Suitable FCS are also taught in PCT Patent Publication No. WO 2009/032954, published 12 Mar. 2009) and which is incorporated by reference here particularly with respect to the furin cleavage sequences disclosed therein.

B. Functional Domain III

Structurally, domain Ib is understood to comprise residues 365-399. As discussed further herein, while the structural boundary of domain III of PE is considered to start at residue 405, functional analyses have shown that domain III requires a segment of structural domain Ib to retain ADP-ribosylating activity. Accordingly, the functional domain III is defined as residues 395-613 of PE, and it is thus preferred that the toxins of the invention comprise residues 395-613 of PE, with certain permitted variations described further below. Deletion of residues 365-394 other than those in the furin cleavage sequence, is desirable, as the deletions eliminate any immunogenic epitopes present in these portions of the PE molecule. In the PEs of the invention, a furin cleavage sequence, or truncated or modified variants thereof) is attached at its carboxyl end to domain III, having interposed between the two a flexible linker of from 3 to 8 amino acids independently selected from glycine and serine.

In preferred embodiments, the functional domain of the PE molecules are modified to have a substitution of alanine, glycine, serine or glutamine in place of the amino acid residues normally present at positions D406 and Q592 within Domain III. Substitutions at positions D406 and Q592 can be combined with substitutions of alanine, glycine, serine or glutamine at positions R432, R467, R490, R513, E548 and K590 within Domain III. In some embodiments, in addition, at least one amino acid residue corresponding to an amino acid residue at a position selected from D403, R412, R427, E431, R458, D461, R505, E522, R538, R551, R576 and L597 is substituted with an alanine, glycine, serine or glutamine. The substitutions to the residues at positions substitutions within Domain III amino acid residue positions D406, R432, R467, R490, R513, E548, K590 and Q592 of Domain III In some embodiments, the PE functional domain III is substantially identical to or identical to the amino acid sequence of the PE functional domain of SS1-LR/GGS/8M. In some embodiments, the PE functional Domain III is substantially identical to or is identical to the amino acid sequence of the PE functional domain of SS1-LR/GGS/8X.

It is understood that the sequence of native PE and the variants discussed above can have conservative substitutions and retain cytotoxic capability and, desirably, reduced antigenicity compared to the native sequence of PE. In preferred embodiments, modified variants of PE or cytotoxic fragments thereof have at least 80% sequence similarity, preferably at least 85% sequence similarity, more preferably at least 90% sequence similarity, and most preferably at least 95% sequence similarity at the amino acid level, with the PE functional domain III of interest, that of SS1-LR/GGS/8M or SS1-LR/GGS/8M. PCT Publication No. WO/2011/032022 published on Mar. 17, 20011 and corresponding to PCT/US2010/048504 filed on Sep. 10, 2010, discloses suitable mutations which reduce the antigenicity of the functional domain II of PE. This published application is incorporated by reference in its entirety with respect to the mutations and substitutions and molecules disclosed therein which provide for the reduced immunogenicity of a functional Domain III.

The term "conservatively modified variants" applies to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

Assaying for Cytotoxicity or Antigenicity of PE

*Pseudomonas* exotoxins employed in the invention can be assayed for the desired level of cytotoxicity by assays well known to those of skill in the art. Thus, cytotoxic fragments of PE and conservatively modified variants of such fragments can be readily assayed for cytotoxicity. A large number of candidate PE molecules can be assayed simultaneously for cytotoxicity by methods well known in the art. For example, subgroups of the candidate molecules can be assayed for cytotoxicity. Positively reacting subgroups of the candidate molecules can be continually subdivided and reassayed until the desired cytotoxic fragment(s) is identified. Such methods allow rapid screening of large numbers of cytotoxic fragments or conservative variants of PE. Antigenicity can be assayed any method known in the art, including the assays taught in WO 2007/016150.

C. Anti-Mesothelin Antibodies

The targeting component of the chimeric molecule specifically binds the cell surface marker mesothelin. Cell surface antigens that are targets for chimeric molecules are well known in the art, and summarized, e.g., in Mufson, *Front Biosci* (2006) 11:337-43; Frankel, *Clin Cancer Res*

(2000) 6:326-334 and Kreitman, *AAPS Journal* (2006) 8(3): E532-E551. Exemplary cancers whose growth, spread and/or progression can be reduced or inhibited by targeting mesothelin include ovarian cancer, mesothelioma, non-small cell lung cancer, lung adenocarcinoma, fallopian tube cancer, head and neck cancer, cervical cancer and pancreatic cancer. In another preferred embodiment, the targeting moiety is an antibody fragment, preferably an antibody fragment specifically binding to a surface marker on a cell. A preferred antibody fragment is a single chain Fv. Herein the construction and characterization of cytotoxin-based immunotoxins wherein the cytotoxin is fused to a scFv are described. Other preferred antibody fragments to which a toxin or cytotoxic fragment can be fused include Fab, Fab', F(ab')2, Fv fragment, a helix-stabilized antibody, a diabody, a disulfide stabilized antibody, and a single domain antibody (e.g., a camelid antibody). Antibodies against mesothelin include SS1, SSP1, HN1, HN2, MN, K1 and variants thereof. MORAb-009 (a humanized version of SS1) is a particularly suitable antibody.

SS1P has been shown to specifically kill mesothelin expressing cell lines and to cause regressions of mesothelin expressing tumors in mice (Hassan, R. et al., *Clin Cancer Res* 8:3520-6 (2002); Onda, M. et al., *Cancer Res* 61:5070-7 (2001)). Based on these studies and appropriate safety data, 2 phase I trials with SS1P are being conducted at the National Cancer Institute in patients with mesothelin expressing cancers (Chowdhury, P. S. et al., *Proc Natl Acad Sci USA* 95:669-74 (1998); Hassan, R. et al., *Proc Am Soc Clin Oncol* 21:29a (2002) each incorporated herein by reference with respect to the SS1P subject matter disclosed therein.). In addition, other therapies targeting mesothelin are in preclinical development (Thomas, A. M. et al., *J Exp Med* 200:297-306 (2004)). HN1 and HN2 are human anti-mesothelin antibodies, described, e.g., in Feng, et al., *Mol Cancer Ther* (2009) 8(5):1113-8. SS1P immunotoxins where cleavage clusters for lysosomal proteases have been removed. These variants are described, e.g., in Weldon, et al., *Blood*, (2009) 113(16):3792-800 and in WO 2009/032954, which are incorporated herein in their entirety with respect to the antibodies, FCS, and functional domains III disclosed therein.

RITs of the invention include, but are not limited to, molecules in which there is a covalent linkage of a PE molecule to an antibody or other targeting agent. The fusion of a cytotoxin to an antibody or antibody fragment is typically to a C-terminus of the antibody or antibody fragment. Such fusion typically is accomplished employing recombinant DNA technologies. The choice of a particular targeting agent depends on the particular cell to be targeted. The antibodies that target the immunotoxin can be polyclonal, monoclonal, or recombinant antibodies, such as chimeras or variable region fragments. If the antibody is non-recombinant, the immunotoxin must be formed by chemical conjugation of the antibody to the toxic moiety. If the antibody is produced recombinantly, the antibody can be joined to the toxin through chemical bonding or through recombinant fusion. In recombinant fusion, cDNA encoding the antibody is inserted, in frame, into a plasmid that already contains cDNA which encodes the toxin. Of course, the reverse could be done as well; the toxin cDNA can be inserted into a plasmid carrying cDNA which encodes the antibody. Because of the potential large size of the immunotoxin, it is sometimes desired to join only a fragment of an antibody to the toxic moiety. Fab, Fab' and F(ab)$_2$ fragments can be made from polyclonal, monoclonal and chimeric antibodies and then joined to the toxin through chemical bonding. Alternatively, a cDNA can be produced in which the variable regions of an antibody are connected to essential framework regions. These smaller antibodies are then secreted as double chain Fv antibodies or, if the heavy and light chain regions are joined either directly or through a peptide linker, as single chain Fv antibodies (scFv). Particularly preferred mesothelin antibodies and fragments, where cleavage clusters for lysosomal proteases are removed, are disclosed in PCT patent publication no. WO/2000/073346, published on Jul. 12, 2000 which corresponds to PCT/US2009/014829, filed on May 26, 2000, assigned to the same assignee as the present invention, and which is incorporated by reference in its entirety particularly with respect to the antibody subject matter disclosed therein.

One method of creating a scFv is through phage display libraries made from splenic mRNA of mice immunized with an immunogen (Chowdhury, et al., *Mol. Immunol.* 34:9-20 (1997)). If a protein immunogen is naturally found in mammals but is recombinantly expressed in prokaryotes, however, the protein will not have the correct glycosylation pattern and may not have the correct conformation. Antibodies developed by the mouse in response to this immunogen may not recognize the protein in its native state. One solution to this problem is to immunize animals with the native protein made in mammalian cells, but purification from mammalian cells of sufficient amounts of some proteins, in particular cell surface proteins, may not be possible. Another solution, although not as common, is to immunize animals with cDNA which encodes the immunogen. The cDNA, under the control of an appropriate promoter, is introduced into the animal. After boosting injections and when the antibody titer reaches a maximum, the animals are sacrificed and the spleens removed to create the phage display library. By immunizing mice with plasmids containing DNA encoding mesothelin, we are able to elicit high titers of anti-mesothelin antibodies. Using splenic RNA and phage display technology, one can isolate a single-chain Fv ("scFv"), which we called SS scFv, that binds with high affinity to mesothelin.

The anti-mesothelin antibodies for use in the present invention can be linked to the FCS through the FCS amino terminus. Similarly, the FCS can be linked directly to the heavy, light, Fc (constant region) or framework regions of the antibody. Linkage can occur through the antibody's amino or carboxyl termini, or through an interior amino acid residue. The antibodies used in a multivalent immunoconjugate composition of the present invention can be directed to the same or different mesothelin epitopes.

In preferred embodiments of the present invention, the anti-mesothelin antibody is a recombinant antibody such as a scFv or a disulfide stabilized Fv antibody. Fv antibodies are typically about 25 kDa and contain a complete antigen-binding site with 3 CDRs per heavy and light chain. If the $V_H$ and the $V_L$ chain are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker.

In a particularly preferred embodiment, the antibody is a single chain Fv (scFv). The $V_H$ and the $V_L$ regions of a scFv antibody comprise a single chain which is folded to create an antigen binding site similar to that found in two chain antibodies. Once folded, noncovalent interactions stabilize the single chain antibody. In a more preferred embodiment, the scFv is recombinantly produced. One of skill will realize that conservative variants of the antibodies of the instant invention can be made. Such conservative variants employed in scFv fragments will retain critical amino acid residues necessary for correct folding and stabilizing between the $V_H$ and the $V_L$ regions. In some embodiments of the present invention, the scFv antibody is directly linked to the FCS through the light chain.

While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston, et al., *Proc. Nat'l Acad. Sci. USA* 8:5879 (1988); Bird, et al., *Science* 242:4236 (1988); Glockshuber, et al., *Biochemistry* 29:1362 (1990); U.S. Pat. Nos. 4,946,778, 5,132,405 and Stemmer, et al., *Biotechniques* 14:256-265 (1993), all incorporated herein by reference. Generally the peptide linker will have no specific biological activity other than to join the regions or to preserve some minimum distance or other spatial relationship between them. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Ser (SEQ ID NO:50), preferably 2, 3, 4, 5, or 6 such sequences. However, it is to be appreciated that some amino acid substitutions within the linker can be made. For example, a valine can be substituted for a glycine.

Preferably, the antibody or fragment thereof comprises a mutated antibody heavy chain variable region or light chain variable region, the polypeptide having at least 5 times higher binding affinity for an antigen than does a parental antibody, the polypeptide having a sequence that differs from the parental antibody by an amino acid substitution of at least one amino acid in a complementarity determining region (CDR), the amino acid encoded by a codon that comprises a nucleotide belonging to a hot spot motif selected from AGY or RGYW, wherein R is A or G, Y is C or T and W is A or T. The substitution can occur in the CDR3 of a light or heavy chain variable region. The substitution can occur in the CDR1 or CDR2 of a light or heavy chain variable region. In some embodiments, the anti-mesothelin antibody is an antibody material disclosed in U.S. Pat. No. 7,081,518 issued on Jul. 25, 2006 and which is incorporated by reference with respect to such antibodies, their nucleic acid equences, uses and methods of making.

The anti-mesothelin antibody can comprise a variable heavy ("$V_H$") chain and a variable light ("$V_L$") chain, which $V_H$ and $V_L$ chains each have a first, a second and a third complementarity-determining region ("CDR"), wherein the first CDR ("CDR1"), the second CDR ("CDR2"), and third CDR ("CDR3"), respectively, of said heavy chain have the amino acid residue sequence shown for CDR1 (GYTMN; SEQ ID NO:51), CDR2 (LITPYNGASSYNQKFRG; SEQ ID NO:52), and CDR3 (GGYDGRGFDY; SEQ ID NO:53), and wherein CDRs 1, 2 and 3 respectively, of said $V_L$ chain, have the amino acid residue sequence shown for CDR1 (SASSSVSYMH; SEQ ID NO:54), CDR2 (DTSKLAS; SEQ ID NO:55), and CDR3 (QQWSGYPLT; SEQ ID NO:56). In some embodiments, the CDR3 of the light chain is modified and has the sequence QQWSKHPLT (SEQ ID NO:57), QQWSGHPLT (SEQ ID NO:58), QQWSAHPLT (SEQ ID NO:59), QQWSQIPLT (SEQ ID NO:60), QQWGFNPLT (SEQ ID NO:61), QQWGTNPLT (SEQ ID NO:62), QQWGSHPLT (SEQ ID NO:63), QQWGDFPLT (SEQ ID NO:64), QQWGDHPLT (SEQ ID NO:65), QQWSAHPLT (SEQ ID NO:66), or QQWSGYPTT (SEQ ID NO:67). In some embodiments the $V_H$ is connected to $V_L$ by a linker peptide, GVGGSG$_4$SG$_4$S (SEQ ID NO:25). In some further embodiments, the anti-mesothelin antibody is a scFv, dsFv, a Fab, or a F(ab')$_2$. In still some further embodiments, the anti-mesothelin antibody to be used in the RIT comprises an amino acid substitution of at least one amino acid in a CDR selected from the group consisting of $V_L$ CDR1, $V_L$ CDR2, $V_H$ CDR1, and $V_H$ CDR2, said amino acid being encoded by a codon that comprises a nucleotide belonging to a hot spot motif selected from AGY or RGYW, where R is A or G, Y is C or T and W is A or T.

D. L1

The antibody is linked to the FCS by an additional linker which is preferably a bond or a polypeptide from 1 to 10 continuous amino acids in length. In some embodiments, this linker is from 1, 2, 3, 4, 5, 6, 7, 8, or 9 amino acids in length. In some preferred embodiments, the linker consists of glycine and serine residues. In some further embodiments, the linker is ASGG (SEQ ID NO:19) or ASGGSGGG (SEQ ID NO:68). In preferred embodiments, the linker forms a continuous polypeptide chain which directly joins a carboxyl terminus of the antibody to the N-terminus of the FCS.

E. The Flexible Linker

The flexible linker directly couples the FCS to the PE functional Domain III. The flexible linker is a continuous peptide of the formula (Xaa1)$_n$ where each Xaa1 is independently selected from glycine and serine and n is from 3 to 8. In preferred embodiments, n is 3. In a more preferred embodiment, the linker is GGS. In other embodiments, n is 4, 5, 6, or 7. In other embodiments, the flexible linker is GGGS (SEQ ID NO:50), GGGSG (SEQ ID NO:69), GGGGSG (SEQ ID NO:70) or GGSGGS (SEQ ID NO:18).

The flexible linker is fused in sequence to the C-terminus of the FCS and fused directly fused in sequence to the functional domain III of PE and, accordingly, forms one continuous peptide chain with the FCS and the functional domain III.

Production of Immunoconjugates i. Non-Recombinant Methods

In a non-recombinant embodiment of the invention, a targeting molecule, such as an antibody, is linked to a PE molecule of the present invention using any number of means known to those of skill in the art. Both covalent and noncovalent attachment means may be used with PE molecules of the present invention.

The procedure for attaching a PE molecule to an antibody or other targeting molecule ("TM") will vary according to the chemical structure of the TM. Polypeptides typically contain a variety of functional groups; e.g., carboxylic acid (COOH), free amine (—NH$_2$) or sulfhydryl (—SH) groups, which are available for reaction with a suitable functional group on an antibody, for example, to result in the binding of the PE molecule.

Alternatively, the antibody or other TM is derivatized to expose or to attach additional reactive functional groups. The derivatization may involve attachment of any of a number of linker molecules such as those available from Pierce Chemical Company, Rockford Ill.

A "linker", as used herein, is a molecule that is used to join the TM to the PE molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the PE molecule from the TM when the immunoconjugate has reached its target site. Therefore, in these circumstances, immunoconjugates will comprise linkages which are cleavable in the vicinity of the target site. Cleavage of the linker to release the PE molecule from the TM may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

ii. Recombinant Methods

The nucleic acid sequences of the present invention can be prepared by any suitable method including, for example, cloning of appropriate sequences or by direct chemical synthesis by methods such as the phosphotriester method of Narang, et al., *Meth. Enzymol.* 68:90-99 (1979); the phosphodiester method of Brown, et al., *Meth. Enzymol.* 68:109-151 (1979); the diethylphosphoramidite method of Beaucage, et al., *Tetra. Lett.* 22:1859-1862 (1981); the solid phase phosphoramidite triester method described by Beaucage & Caruthers, *Tetra. Letts.* 22(20):1859-1862 (1981), e.g., using an automated synthesizer as described in, for example, Needham-VanDevanter, et al. *Nucl. Acids Res.* 12:6159-6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook, et al., MOLECULAR CLONING: A LABORATORY MANUAL (2ND ED.), Vols. 1-3, Cold Spring Harbor Laboratory (1989)), Berger and Kimmel (eds.), GUIDE TO MOLECULAR CLONING TECHNIQUES, Academic Press, Inc., San Diego Calif. (1987)), or Ausubel, et al. (eds.), CURRENT PROTOCOLS IN MOLECULAR BIOLOGY, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Nucleic acids encoding native PE can also be modified to form the immunoconjugates of the present invention. Modification by site-directed mutagenesis is well known in the art. Nucleic acids encoding PE can be amplified by in vitro methods. Amplification methods include the polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In a preferred embodiment, immunoconjugates are prepared by inserting the cDNA which encodes an antibody or other TM of choice into a vector which comprises the cDNA encoding a desired PE of the invention. The insertion is made so that the targeting agent (for ease of discussion, the discussion herein will assume the targeting agent is an Fv, although other targeting agents could be substituted with equal effect) and the PE are read in frame, that is in one continuous polypeptide which contains a functional Fv region and a functional PE region. In a particularly preferred embodiment, cDNA encoding a PE of the invention is ligated to a scFv so that the toxin is located at the carboxyl terminus of the scFv. In other preferred embodiments, cDNA encoding a PE of the invention is ligated to a scFv so that the toxin is located at the amino terminus of the scFv.

Once the nucleic acids encoding a PE, antibody, or an immunoconjugate of the present invention are isolated and cloned, one may express the desired protein in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eucaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

One of skill would recognize that modifications can be made to a nucleic acid encoding a polypeptide of the present invention (i.e., PE or an immunoconjugate formed from a PE of the invention) without diminishing its biological activity.

Some modifications may be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly H is) to aid in purification steps.

In addition to recombinant methods, the immunoconjugates and PEs of the present invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3-284; Merrifield, et al. *J. Am. Chem. Soc.* 85:2149-2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N-dicycylohexylcarbodiimide) are known to those of skill.

iii. Purification

Once expressed, the recombinant immunoconjugates and PEs of the present invention can be purified according to standard procedures of the art, including ammonium sulfate precipitation, affinity columns, column chromatography, and the like (see, generally, R. Scopes, PROTEIN PURIFICATION, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies of this invention. See, Buchner, et al., *Anal. Biochem.* 205:263-270 (1992); Pluckthun, Biotechnology 9:545 (1991); Huse, et al., *Science* 246:1275 (1989) and Ward, et al., *Nature* 341:544 (1989), all incorporated by reference herein.

Often, functional heterologous proteins from *E. coli* or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena, et al., *Biochemistry* 9: 5015-5021 (1970), incorporated by reference herein, and especially as described by Buchner, et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione, and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

2. Pharmaceutical Compositions and Administration

In one aspect the present invention provides a pharmaceutical composition or a medicament comprising at least one chimeric protein of the present invention, preferably a targeted toxin, and optionally a pharmaceutically acceptable carrier. A pharmaceutical composition or medicament can be administered to a patient for the treatment of a condition, including, but not limited to, a malignant disease or cancer.

a. Formulation

Pharmaceutical compositions or medicaments for use in the present invention can be formulated by standard techniques using one or more physiologically acceptable carriers or excipients. Suitable pharmaceutical carriers are described herein and in *Remington: The Science and Practice of Pharmacy,* 21$^{st}$ Ed., University of the Sciences in Philadelphia, Lippencott Williams & Wilkins (2005). The chimeric proteins of the present invention can be formulated for administration by any suitable route, including via inhalation, topically, nasally, orally, parenterally, or rectally. Thus, the administration of the pharmaceutical composition may be made by intradermal, subdermal, intravenous, intramuscular, intranasal, inhalationally, intracerebral, intratracheal, intraarterial, intraperitoneal, intravesical, intrapleural, intracoronary, subcutaneously or intratumoral injection, with a syringe or other devices. Transdermal administration is also contemplated, as are inhalation or aerosol administration. Tablets and capsules can be administered orally, rectally or vaginally.

The compositions for administration will commonly comprise a solution of the chimeric protein, preferably a targeted toxin, dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

The targeted toxin compositions of this invention are suited for parenteral administration, including intravenous administration or administration into a body cavity.

The chimeric proteins, preferably targeted toxins, of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

Controlled release parenteral formulations of the targeted toxin compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, e.g., Kreuter J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp. 315-339 (1992), both of which are incorporated herein by reference.

Polymers can be used for ion-controlled release of targeted toxin compositions of the present invention. Various degradable and nondegradable polymeric matrices for use in controlled drug delivery are known in the art (Langer R., *Accounts Chem. Res.*, 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.*, 9:425-434 (1992); and Pec et al., *J. Parent. Sci. Tech.*, 44(2):58-65 (1990)). Alternatively, hydroxyapatite has been used as a microcarrier for controlled release of proteins (Ijntema et al., *Int. J. Pharm.*, 112:215-224 (1994)). In yet another aspect, liposomes are used for controlled release as well as drug targeting of the lipid-capsulated drug (Betageri et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Suitable formulations for transdermal application include an effective amount of a composition of the present invention with a carrier. Preferred carriers include absorbable pharmacologically acceptable solvents to assist passage through the skin of the host. For example, transdermal devices are in the form of a bandage comprising a backing member, a reservoir containing the composition optionally with carriers, optionally a rate controlling barrier to deliver the composition to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., a composition of the present invention, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active composition.

For administration by inhalation the chimeric protein, preferably an antibody and/or targeted toxin may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, 1,1,1,2-tetrafluorethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the chimeric protein, preferably an antibody and/or targeted toxin and a suitable powder base, for example, lactose or starch.

The compositions can also be formulated in rectal compositions, for example, suppositories or retention enemas, for example, containing conventional suppository bases, for example, cocoa butter or other glycerides.

Furthermore, the compositions can be formulated as a depot preparation. Such long-acting formulations can be administered by implantation (for example, subcutaneously or intramuscularly) or by intramuscular injection. Thus, for example, the composition can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

b. Dosage

In one embodiment of the present invention, a pharmaceutical composition or medicament is administered to a patient at a therapeutically effective dose to prevent, treat, or control a disease or malignant condition, such as cancer. The pharmaceutical composition or medicament is administered to a patient in an amount sufficient to elicit an effective therapeutic or diagnostic response in the patient. An effective therapeutic or diagnostic response is a response that at least partially arrests or slows the symptoms or complications of the disease or malignant condition. An amount adequate to accomplish this is defined as "therapeutically effective dose."

The dosage of chimeric proteins, preferably targeted toxins, or compositions administered is dependent on the species of warm-blooded animal (mammal), the body weight, age, individual condition, surface area of the area to be treated and on the form of administration. The size of the dose also will be determined by the existence, nature, and extent of any adverse effects that accompany the administration of a particular compound in a particular subject. A unit dosage for administration to a mammal of about 50 to 70 kg may contain between about 5 and 500 mg of the active ingredient. Typically, a dosage of the compound of the present invention, is a dosage that is sufficient to achieve the desired effect.

Optimal dosing schedules can be calculated from measurements of chimeric protein, preferably targeted toxin, accumulation in the body of a subject. In general, dosage is from 1 ng to 1,000 mg per kg of body weight and may be given once or more daily, weekly, monthly, or yearly. Persons of ordinary skill in the art can easily determine optimum dosages, dosing methodologies and repetition rates. One of skill in the art will be able to determine optimal dosing for administration of a chimeric protein, preferably a targeted toxin, to a human being following established protocols known in the art and the disclosure herein.

Optimum dosages, toxicity, and therapeutic efficacy of compositions may vary depending on the relative potency of individual compositions and can be determined by standard pharmaceutical procedures in cell cultures or experimental animals, for example, by determining the LD50 (the dose lethal to 50% of the population) and the ED50 (the dose therapeutically effective in 50% of the population). The dose ratio between toxic and therapeutic effects is the therapeutic index and can be expressed as the ratio, $LD_{50}/ED_{50}$. Compositions that exhibit large therapeutic indices are preferred. While compositions that exhibit toxic side effects can be used, care should be taken to design a delivery system that targets such compositions to the site of affected tissue to minimize potential damage to normal cells and, thereby, reduce side effects.

The data obtained from, for example, animal studies (e.g. rodents and monkeys) can be used to formulate a dosage range for use in humans. The dosage of compounds of the present invention lies preferably within a range of circulating concentrations that include the $ED_{50}$ with little or no toxicity. The dosage can vary within this range depending upon the dosage form employed and the route of administration. For any composition for use in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a chimeric protein, preferably a targeted toxin is from about 1 ng/kg to 100 mg/kg for a typical subject.

A typical targeted toxin composition of the present invention for intravenous administration would be about 0.1 to 10 mg per patient per day. Dosages from 0.1 up to about 100 mg per patient per day may be used. Actual methods for preparing administrable compositions will be known or apparent to those skilled in the art and are described in more detail in such publications as *Remington: The Science and Practice of Pharmacy*, $21^{st}$ Ed., University of the Sciences in Philadelphia, Lippencott Williams & Wilkins (2005).

Exemplary doses of the compositions described herein, include milligram or microgram amounts of the composition per kilogram of subject or sample weight (e.g., about 1 microgram per-kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a composition depend upon the potency of the composition with respect to the desired effect to be achieved. When one or more of these compositions is to be administered to a mammal, a physician, veterinarian, or researcher may, for example, prescribe a relatively low dose at first, subsequently increasing the dose until an appropriate response is obtained. In addition, it is understood that the specific dose level for any particular mammal subject will depend upon a variety of factors including the activity of the specific composition employed, the age, body weight, general health, gender, and diet of the subject, the time of administration, the route of administration, the rate of excretion, any drug combination, and the degree of expression or activity to be modulated.

In one embodiment of the present invention, a pharmaceutical composition or medicament comprising a chimeric protein, preferably a targeted toxin, of the present invention is administered, e.g., in a daily dose in the range from about 1 mg of compound per kg of subject weight (1 mg/kg) to about 1 g/kg. In another embodiment, the dose is a dose in the range of about 5 mg/kg to about 500 mg/kg. In yet another embodiment, the dose is about 10 mg/kg to about 250 mg/kg. In another embodiment, the dose is about 25 mg/kg to about 150 mg/kg. A preferred dose is about 10 mg/kg. The daily dose can be administered once per day or divided into subdoses and administered in multiple doses, e.g., twice, three times, or four times per day. However, as will be appreciated by a skilled artisan, compositions described herein may be administered in different amounts and at different times. The skilled artisan will also appreciate that certain factors may influence the dosage and timing required to effectively treat a subject, including but not limited to the severity of the disease or malignant condition, previous treatments, the general health and/or age of the subject, and other diseases present. Moreover, treatment of a subject with a therapeutically effective amount of a composition can include a single treatment or, preferably, can include a series of treatments.

Following successful treatment, it may be desirable to have the subject undergo maintenance therapy to prevent the recurrence of the disease or malignant condition treated.

c. Administration

The compositions of the present invention can be administered for therapeutic treatments. In therapeutic applications, compositions are administered to a patient suffering from a disease or malignant condition, such as cancer, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Determination of an effective amount is well within the capability of those skilled in the art, especially in light of the detailed disclosure provided herein. Generally, an efficacious or effective amount of an immunoconjugate is determined by first administering a low dose or small amount of the immunoconjugate, and then incrementally increasing the administered dose or dosages, adding a second or third medication as needed, until a desired effect of is observed in the treated subject with minimal or no toxic side effects.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

To achieve the desired therapeutic effect, compositions may be administered for multiple days at the therapeutically effective daily dose. Thus, therapeutically effective administration of compositions to treat a disease or malignant condition described herein in a subject may require periodic (e.g., daily) administration that continues for a period ranging from three days to two weeks or longer. Typically, compositions will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the compounds or compositions are not administered daily, so long as the administration is repeated frequently enough to maintain a therapeutically effective concentration of the composition in the subject. For example, one can administer a composition every other day, every third day, or, if higher dose ranges are employed and tolerated by the subject, once a week.

3. Methods of Inhibiting Tumor Growth

The compositions of the present invention find use in a variety of ways. For example, the PE molecules of the present invention, e.g., as part of a chimeric molecule, find use to (i) induce apoptosis in a cell bearing one or more surface markers (ii) inhibit unwanted growth, hyperproliferation or survival of a cell bearing one or more cell surface markers, (iii) treat a condition, such as a cancer, and (iv) provide therapy for a mammal having developed a disease caused by the presence of cells bearing one or more cell surface marker.

Any cell or tumor cell expressing mesothelin as a cell surface marker can be used to practice a method of the present invention. Methods of the present invention can be practiced in vitro or in vivo. When referring to a cell, it is understood that that this term also includes a population of cells, i.e., more than one cell.

Using Compositions for Inducing Apoptosis in a Cell Bearing One or More Cell Surface Markers Apoptosis plays a central role in both the development and homeostasis of multicellular organisms. "Apoptosis" refers to programmed cell death and is characterized by certain cellular characteristics, such as membrane blobbing, chromatin condensation and fragmentation, formation of apoptotic bodies and a [positive "TUNEL" (terminal deoxynucleotidyl transferase-mediated UTP nick end-labeling) staining pattern. A later step in apoptotic process is the degradation of the plasma membrane, rendering apoptotic cells leaky to various dyes (e.g., propidium iodide).

Apoptosis can be induced by multiple independent signaling pathways that converge upon a final effector mechanism consisting of multiple interactions between several death receptors and their ligands, which belong to the tumor necrosis factor (TNF) receptor/ligand superfamily. The best-characterized death receptors are CD95 ("Fas"), TNFR1 (p55), death receptor 3 (DR3 or Apo3/TRAMO), DR4 and DR5 (apo2-TRAIL-R2). The final effector mechanism of apoptosis is the activation of a series of proteinases designated as caspases. The activation of these caspases results in the cleavage of a series of vital cellular proteins and cell death.

The present invention provides methods for inducing apoptosis in a cell expressing mesothelin. In one aspect, the method for inducing apoptosis in a cell comprises the step of exposing or contacting the cell expressing mesothelin as a cell surface marker to a RIT of the present invention. Typically, the cells are exposed to or contacted with effective amounts of the immunoconjugate, wherein the contacting results in inducing apoptosis.

In another aspect of present invention, a method of inducing a tumor cell expressing mesothelin on its surface to undergo apoptosis is provided comprising the step of administering to a subject a RIT of the present invention.

Using Compositions for Inhibiting Growth, Hyperproliferation, or Survival of a Cell Bearing One or More Cell Surface Marker It is an object of the present invention to provide improved therapeutic strategies for treatment of cancers using the compositions of the invention. In one aspect of the present invention, a method for inhibiting at least one of unwanted growth, hyperproliferation, or survival of a cell is provided. This method comprises the step of contacting a cell expressing mesothelin as a surface marker with an effective amount of a PE of the present invention, e.g., as part of a chimeric molecule, as described herein, wherein the step of contacting results in the inhibition of at least one of unwanted growth, hyperproliferation, or survival of the cell. In one embodiment, this method comprises the step of determining whether the cell expresses one or more cell surface markers, for example, a cell surface receptor. Typically, the cells are exposed to or contacted with an effective amounts of the immunoconjugate, wherein the contacting results in the inhibition of at least one of unwanted growth, hyperproliferation, or survival of the cell.

Thus, in one aspect of the present invention methods of inhibiting growth of a population of cells bearing mesothelin are provided. In a preferred embodiment, this method comprises the steps of (a) contacting a population of cells with a chimeric protein according to the invention. Many tumors form metastasis. Thus, in another aspect of the present invention, the compositions of the present invention are used to prevent the formation of a metastasis. This method comprises the step of administering to a tumor cell a composition of the present invention wherein the administering results in the prevention of metastasis. In a preferred embodiment, the composition comprises a targeted toxin comprising an antibody against a cell surface antigen and a PE of the present invention. Typically, the cells are exposed to or contacted with effective amounts of the immunoconjugate, wherein the contacting results in the prevention of metastasis. Exemplary cancers whose growth, spread and/or progression can be inhibited include ovarian cancer, mesothelioma, non-small cell lung cancer, lung adenocarcinoma and pancreatic cancer.

Using Compositions for Treating Cancer

Methods of the present invention can be practiced in vitro and in vivo. Thus, in another aspect of the present invention, a method for treating a subject suffering from a cancerous condition is provided. This method comprises the step of administering to a subject having been diagnosed with a cancer a therapeutically effective amounts of the RIT of the invention, as described herein, wherein the cancerous condition is characterized by unwanted growth or proliferation of a cell expressing one or more cell surface marker, and wherein the step of administering results in the treatment of the subject. Typically, the cells are exposed to or contacted with effective amounts of the immunotoxin, wherein the contacting results in the treatment of the subject.

In one embodiment of the present invention, an immunotoxin comprising a PE of the present invention is used to treat a subject suffering from a cancer mediated by mesothelin-CA125 binding interaction. Exemplary cancers whose growth, spread and/or progression are at least partially mediated by CA125/mesothelin binding include ovarian cancer, mesothelioma, non-small cell lung cancer, lung adenocarcinoma and pancreatic cancer.

Methods for treating cancer may optionally comprise one or more of the following steps: obtaining a biological sample of tissue or fluid from an individual; screening the biological sample for the expression of mesothelin by contacting the biological sample with an antibody directed to the surface marker or screening the biological sample for expression of the surface marker polynucleotide by detecting a surface marker mRNA. This can be done using standard technologies known in the art, e.g., Western blotting, Northern blotting or PCR.

Using Compositions for Treating a Subject Having Developed a Disease Caused by the Presence of Cells Bearing One or More Cell Surface Markers Also provided is a method a method of providing therapy for a mammal having developed a disease caused by the presence or aberrant proliferation of cells preferentially bearing or overexpressing mesothelin. In a preferred embodiment, this method comprises the step of administering to said mammal a RIT of the invention. Typically, the cells are exposed to or contacted with effective amounts of the immunotoxin, wherein the contacting results in the treatment of the subject.

In another embodiment, this invention provides for eliminating target cells in vitro or ex vivo using the RITs of the present invention. For example, chimeric molecules comprising the RITs of the invention can be used to purge targeted cells from a population of cells in a culture. Thus, for example, cells cultured from a patient having a cancer expressing mesothelin can be purged of cancer cells by contacting the culture with chimeric molecules directed against mesothelin as described herein.

In some instances, the target cells may be contained within a biological sample. A "biological sample" as used herein is a sample of biological tissue or fluid that contains target cells and non-target cells. Such samples include, but are not limited to, tissue from biopsy, blood, and blood cells (e.g., white cells). A biological sample is typically obtained from a multicellular eukaryote, preferably a mammal such as rat, mouse, cow, dog, guinea pig, or rabbit, and more preferably a primate, such as a macaque, chimpanzee, or human. Most preferably, the sample is from a human.

Methods of Monitoring Response to Treatment with an RIT of the Invention

The invention provides methods of detecting inhibition of tumor growth in a patient suffering from or susceptible to a cancer that can be treated with a RIT of the invention. The methods are particularly useful for monitoring a course of treatment being administered to a patient using the RITs of the present invention, The methods can be used to monitor both therapeutic treatment on symptomatic patients and prophylactic treatment on asymptomatic patients.

The monitoring methods entail determining a baseline value of tumor burden in a patient before administering a dosage of the RITs of the present invention and comparing this with a value for the tumor burden after treatment, or with the tumor burden in a patient receiving no treatment.

A significant decrease (i.e., greater than the typical margin of experimental error in repeat measurements of the same sample, expressed as one standard deviation from the mean of such measurements) in value of the tumor burden signals a positive treatment outcome (i.e., that administration of the RITs of the present invention has blocked progression of tumor growth and/or metastasis).

In other methods, a control value (i.e., a mean and standard deviation) of tumor burden is determined for a control population or a normal population (e.g., burden=zero). Typically, the individuals in the control population have not received prior treatment. Measured values of the tumor burden in a patient after administering the RITs of the present invention are then compared with the control value. A significant decrease in tumor burden relative to the control value (e.g., greater than one standard deviation from the mean) signals a positive treatment outcome. A lack of significant decrease or an increase signals a negative treatment outcome.

In other methods, a control value of tumor burden (e.g., a mean and standard deviation) is determined from a control population of individuals who have undergone treatment receiving a regimen of RITs of the present invention, e.g., as part of a chimeric molecule, as described herein. Measured values of tumor burden in a patient are compared with the control value. If the measured level in a patient is not significantly different (e.g., more than one standard deviation) from the control value, treatment can be discontinued.

If the tumor burden level in a patient is significantly above the control value, continued administration of agent is warranted.

In other methods, a patient who is not presently receiving treatment but has undergone a previous course of treatment is monitored for tumor burden to determine whether a resumption of treatment is required. The measured value of tumor burden in the patient can be compared with a value of tumor burden previously achieved in the patient after a previous course of treatment. A significant increase in tumor burden relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a increase in tumor burden relative to the control level (i.e., more than a standard deviation) is an indicator that treatment should be resumed in a patient.

The tissue sample for analysis is typically blood, plasma, serum, mucous, tissue biopsy, tumor, ascites or cerebrospinal fluid from the patient. The sample can analyzed for indication of neoplasia. Neoplasia or tumor burden can be detected using any method known in the art, e.g., visual observation of a biopsy by a qualified pathologist, or other visualization techniques, e.g., radiography, ultrasound, magnetic resonance imaging (MRI).

Kits, Containers, Devices, and Systems

For use in diagnostic, research, and therapeutic applications described above, kits and systems are also provided by the invention. Kits of the present invention will comprise a RIT of the present invention, e.g., as part of a chimeric molecule. In addition, the kits and systems may include instructional materials containing directions (i.e., protocols) for the practice of the methods of this invention. The instructions may be present in the subject kits in a variety of forms, one or more of which may be present in the kit. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

A wide variety of kits, systems, and compositions can be prepared according to the present invention, depending upon the intended user of the kit and system and the particular needs of the user.

Kits with unit doses of the active composition, e.g. in oral, vaginal, rectal, transdermal, or injectable doses (e.g., for intramuscular, intravenous, or subcutaneous injection), are provided. In such kits, in addition to the containers containing the unit doses will be an informational package insert describing the use and attendant benefits of the composition in treating a disease or malignant condition. Suitable active compositions and unit doses are those described herein above.

Although the forgoing invention has been described in some detail by way of illustration and example for clarity and understanding, it will be readily apparent to one of ordinary skill in the art in light of the teachings of this invention that certain variations, changes, modifications and substitutions of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results. It is also to be understood that the terminology used herein is for the purpose of describing particular embodiments only, and is not intended to be limiting, since the scope of the present invention will be limited only by the appended claims.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature, including accession numbers to GenBank database sequences, referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications.

The invention is further illustrated by the following examples, which are only illustrative and are not intended to limit the definition and scope of the invention in any way.

EXAMPLES

The following examples are offered to illustrate, but not to limit the claimed invention.

Protein

SS1P(SS1 (dsFv)-PE38) and all mutants derived from SS1P were expressed in *Escherichia coli* BL21 (µDE3) from vectors for SS1 (VH)—PE and SS1 ($V_L$, and subsequently refolded and purified as described (Pastan I, Beers R, and Bera T K, *Methods Mol* 248:503-18 (2004)). Stocks of SS1P were prepared by Advanced BioScience Laboratories, Inc. (Kensington, Md.). All other RITs were prepared in the Laboratory of Molecular Biology, National Cancer Institute (Bethesda, Md.). Mutations in SS1P were generated using Quikchange site-directed mutagenesis (Stratagene, La Jolla, Calif.) with primers from Lofstrand Labs Limited (Gaithersburg, Md.).

Cell Lines

A variety of mesothelin-positive human-derived cell lines were used in this study. The L55 lung adenocarcinoma and M30 mesothelioma cell lines were provided by Dr. Steven Albelda, University of Pennsylvania (Philadelphia, Pa.). The HAY mesothelioma cell line was provided by the Stehlin Foundation for Cancer Research (Houston Tex.). The OVCAR-8 and A1847 ovarian cancer cell lines were provided by Dr. Hisataka Kobayashi and Dr. S. Aaronson, respectively, at the National Cancer Institute (Bethesda, Md.). The NCI-H322M lung adenocarcinoma cell line was obtained from Dr. Mitchell Ho at the National Cancer Institute (Bethesda, Md.). The KB31 cell line is a sub-clone of the human epidermal carcinoma KB cell line (Akiyama S et al., *Somat Cell Mol. Genet.*, 11(2):117-26 (1985)). The cell line A431/K5 is a derivative of the A431 epidermoid carcinoma cell line that is transfected with human mesothelin (Chowdhury P S et al., *Proc. Nat. Acad Set USA*, 95: 669-674 (1998)) and grown in Dulbecco's modified essential medium. (DMEM) supplemented with 10% FBS, 2 mM L-glutamine, 1 mM sodium pyruvate, 100 U penicillin, 100 µg streptomycin, and 750 µg/mL G-418 (geneticin). Unless otherwise specified, all cell lines were grown at 37° C. with 5% $CO_2$ in RPMI-1640 medium supplemented with 10% FBS, 2 mM L-glutamine, 1 mM sodium pyruvate, 100 U penicillin, and 100 µs streptomycin (Invitrogen Corporation, Carlsbad, Calif.).

Cytotoxicity Assays

Viability of cell lines treated with immunotoxins was measured using the Cell Counting Kit-8 WST-8 assay (Dojindo Molecular Technologies, Inc., Gaithersburg, Md.) essentially as described in the technical manual. Briefly, 5,000 to 10,000 cells/well were plated in 96-well plates, allowed to attach, and incubated with varying concentrations of RITs for 72 h at a final volume of 0.2 ml, after which 10 µl of the CCK-8 reagent was added to each well. Plates were incubated at 37° C. until the wells with the maximum absorbance at 450 nm reached values of about 1 OD. Values were normalized between the cyclohexamide (10 µg/ml) and buffer (0.2% human serum albumin in PBS) controls and fit to a standard 4-parameter sigmoidal equation with a variable slope using the GraphPad PRISM program to obtain the concentration of immunotoxin at which there was 50% cell death ($EC_{50}$).

Assay of viability of cells from patients with mesothelioma was assayed as described. Briefly, cells were obtained from the pleural fluid or ascites of patients with mesothelioma and seeded at a density of $5\times10^4$ cells/well in a 24-well plate with various concentrations of the RITs SS1P, SS1-LR, BL22 (anti-CD22/PE38) as a negative control, and HB21 (anti-transferrin receptor/PE38) as a positive control. Cells were incubated for 96 hours, fixed, and stained with crystal violet dye. The color intensity of each well was determined by a Versamax microplate reader (Molecular Devices, Inc., Sunnyvale, Calif.) at a wavelength of 595 nm. Each value was determined in triplicate. Statistical analysis of the resulting data by ANOVA was performed using the GraphPad Prism software (GraphPad Software, Inc., La Jolla, Calif.).

Mouse Xenograft Antitumor Assay

Twenty-four female nude mice were injected subcutaneously in the flank with A431/K5 cells on day 0 as described previously (Zhang Y, *Clin Cancer Res.*, 12(15):4695-701 (2006)). Tumor volume was measured regularly by caliper for the next 6 weeks. When the average tumor size reached ~100 $mm^3$, 5 days following implantation, mice were divided into four groups of six and injected QODX3 with 0.2-ml of 0.2% MSA in PBS (vehicle alone) or vehicle containing either SS1P (0.3 mg/kg) or SS1-LR (6.0 or 15 mg/kg). Mice were euthanized if their tumors exceeded 1000 $mm^3$ or at the end of the experiment. Animals were handled according to the National Institutes of Health guidelines approved by the Animal Care and Use Committee of the National Cancer Institute.

RIT Internalization Assay

A431/K5 cells ($10^6$/well) were plated in a 6-well plate (10 $cm^2$ cell) and left incubating overnight. The next day, the medium in each well was replaced with 1 ml of fresh medium containing 1 µg of the RIT to be evaluated. Cells were incubated at 37° C. for various time intervals, after which the well was briefly rinsed with 2 ml cold PBS, 1 ml cold stripping buffer (1 mg/ml BSA in 0.2 M glycine, pH 2.5), and again with 2 ml cold PBS. Cells were subsequently lysed with 200 µl RIPA buffer (150 mM NaCl, 1 mM EDTA, 1% NP-40, 0.5% Na deoxycholate, 0.1% SDS, 50 mM Tris-Cl, pH 8.0) containing a protease inhibitor cocktail (Sigma, St. Louis, Mo.). Samples were analyzed by non-reducing Tris-glycine SOS-PAGE Western blot using a rabbit anti-PE38 polyclonal antibody.

Variable Cytotoxicity of SS1-LR

Initial experiments with SS1-LR demonstrated that it had highly variable cytotoxicity relative to SS1P on a selection of mesothelin-expressing cell lines, ranging from greater than 4-fold more active to 20-fold less active. The general trend, however, was towards a less active molecule. SS1-LR was more than 20% less active relative to SS1P on 5 of the 8 cell lines tested, and only greater than 20% more active on a single cell line. This trend is remarkably different from the anti-CD22 version of the LR molecule, HA22-LR, which typically demonstrated similar or increased cytotoxicity on both cell lines and patient cells (Weldon J E, *Blood.*, 113(16):3792-800 (2009)). These observations indicate there is an intrinsic difference between the intoxication pathway of PE in epithelial cells expressing mesothelin and in B cells expressing CD22.

TABLE 1

Summary of SS1-LR Cytotoxicity

| Cell Line | $EC_{50}$ (ng/ml) | | Relative Activity |
|---|---|---|---|
| | SS1P | SS1-LR | |
| L55 | 5.32 | 4.66 | 1.14 |
| NCI-H322M | 0.63 | 1.80 | 0.35 |
| HAY | 4.79 | 1.05 | 4.56 |
| KB31 | 0.47 | 9.34 | 0.05 |
| M30 | 2.56 | 3.23 | 0.79 |
| A431/K5 | 0.17 | 0.72 | 0.24 |
| OVACR-8 | 1.40 | 4.13 | 0.34 |
| A1847 | 4.59 | 4.70 | 0.98 |

In Vitro SS1-LR Activity

The immunotoxin SS1P (FIG. 1A) consists of the disulfide-stabilized two-chain antimesothelin SS1 Fv joined to PE38 (Chowdhury P S et al., *Proc. Nat. Acad. Sci. USA*, 95: 669-674 (1998); Chowdhury P S and Pastan I., *Nat. Biotechnol.*, 17: 568-572 (1999); Reiter Y and Pastan I., *Clin. Cancer Res.*, 2: 245-252 (1996)). We introduced the LR mutation (Weldon J E, *Blood.*, 113(16):3792-800 (2009); PE Δ251-273 & Δ285-394) into SS1P to create the SS1-LR variant (FIG. 1B) and evaluated its activity in comparison to SS1P against several mesothelin-expressing cell lines in vitro. FIG. 2 shows representative cytotoxicity assays from eight different cell lines.

The lung cancer cell line L55 (A) showed similar sensitivity to both RITs. In contrast, the lung cancer line NCI-H322M (Pal L H et al., *Nat. Med.*, 2(3):350-3 (1996)) was approximately 3-fold less sensitive to SS1-LR than to SS1P. The mesothelioma cell line HAY (G) was greater than 4-fold more sensitive to SS1-LR than to SS1P, but the M30 mesothelioma line (D) was approximately 20% less sensitive to SS-1P-LR. The A431/K5 cell line (H), an epithelial line stably transfected with mesothelin (Chowdhury P S et al., *Proc. Nat. Acad. Sci. USA,* 95: 669-674 (1998); Chang K and Pastan I., *Proc. Natl. Acad. Sci. USA.,* 93, 136-140 (1996)), was about 4-fold less sensitive to SS1-LR compared to SS1P. In addition, the cervical cancer line KB31 (C) is susceptible to killing by SS1P, but its $EC_{50}$ is 20-fold less to SS1-LR. The sensitivities of the ovarian cancer cell lines A1847 (F) and OVCAR-8 (E) to SS1-LR were also evaluated. SS1-LR showed an $EC_{50}$ similar to SS1P on the A1847 line, but a 2-fold reduced $EC_{50}$ on the OVCAR-8 line. Table I summarizes this data and presents the relative $EC_{50}$ values comparing SS1P and SS1-LR. The activity of SS1-LR relative to SS1P varies widely among the different cell lines.

When analyzing the data, we noticed that SS1-LR failed to completely reduce the viability of many of cell lines we evaluated (NCI-H322M, KB31, M30, OVCAR-8, and A1847) to control levels, as defined by cells treated with 10 μg/ml cyclohexamide. This suggested that a sub-population of cells may be sensitive to SS1P, but resistant to SS1-LR. We evaluated this possibility by incubating OVCAR-8 and A 184 7 cells for 4 days with 10 ng/ml of SS1-LR and attempting to culture any surviving cells. No further cell growth was observed following RIT treatment. We conclude that, although complete metabolic inhibition was not obtained by our assay, there is not a sub-population of these cell lines that is resistant to SS1-LR.

In Vivo SS1-LR Activity

We next evaluated the efficacy of SS1-LR using a mouse xenograft tumor model. Of the cell lines we tested in vitro, only A431/K5 grew consistently in our xenograft model. Nude mice with A431/K5 xenograft tumors averaging –100 $mm^3$ were treated intravenously QODX3 (every other day for three doses) with SS1-LR at doses of 6.0 or 15 mg/kg. For comparison, additional groups were treated intravenously QODX3 with either buffer (0.2% HSA in PBS) or 0.3 mg/kg SS1P, the maximum tolerated dose of SS1P under this dosing schedule. Tumor size of each mouse was measured regularly for 22 days post implantation (FIG. 3).

The tumors of PBS-treated mice rapidly grew to an average size greater than 1000 $mm^3$ on day 14 post implantation. Mice treated on days 5, 7 and 9 with 0.3 mg/kg SS1P showed tumor regressions that brought the average tumor size to a minimum of about 53 $mm^3$ on day 12. By day 20 all of the tumors had resumed rapid growth. The 6.0 mg/kg dose of SS1-LR was slightly less potent than 0.3 mg/kg SS1P. Tumors in mice treated with 6.0 mg/kg of SS1-LR reached an average minimum size of 92 $mm^3$ on days 7 and 9, and all resumed rapid growth by day 18. The 15 mg/kg dose of SS1-LR demonstrated significantly better antitumor activity than 0.3 mg/kg SS1P. Tumors in mice treated with 15 mg/kg SS1-LR regressed to an average minimum size of 17 $mm^3$. At day 22, four out of the six tumors had resumed growth, one tumor was unchanged at 10 $mm^3$ since day 18, and one tumor was undetectable after day 15. Although, SS1-LR is approximately 20-fold less active than SS1P in this model, its low nonspecific toxicity allows us to treat mice with high doses and achieve a superior anti-tumor effect.

Processing of Internalized RITs

Differences in intracellular trafficking and processing between SS1P and SS1-LR might account for the variation in activity we observed between the two RITs. To test this hypothesis, we examined the internalization and processing of SS1P and SS1-LR in A431/K5 cells by Western blot (FIG. 4). A431/K5 cells were chosen because they express high levels of mesothelin (about 106 sites/cell) and internalize large quantities of RIT for visualization. We performed a non-reducing SOS-PAGE Western blot on whole cell lysates of A431/K5 cells treated with a continuous incubation of 1 μg/ml of either SS1P or SS1-LR for various time intervals. FIG. 4A shows a time course of SS1P treatment, while FIG. 4B shows a time course of SS1-LR treatment.

As expected, A431/K5 cells treated with either SS1P or SS1-LR have prominent bands at positions indicative of the full-length (62-kDa and 50-kDa, respectively) and reduced (51-kDa and 39-kDa, respectively) forms of the two RITs. Both RITs contain three disulfide bonds in the Fv region: one intrachain bond each in the VH and VL fragments, and one interchain bond between the $V_H$ and $V_L$ (FIG. 1). SS1P contains an additional disulfide bond in domain II between cysteine residues flanking the furin cleavage site ($Cys^{265}$ and $Cys^{287}$). The oxidation state of the additional disulfide bond in SS1P appears to change the migration of SS1P in SOS-PAGE, causing the observed doublet (FIG. 4A, Reduced). These bands collapse into a single band when treated with reducing agent (data not shown).

We also expected to observe bands corresponding to the C-terminal furin cleavage fragments of SS1P and SS1-LR (34-kDa and 24-kDa, respectively). Lysates from SS1P-treated cells show a prominent band near 34-kDa, indicative of the furin cleavage fragment. In contrast, lysates from SS1-LR-treated cells show only a weak band corresponding to 24-kDa. The intensity of each band was quantified with the ImageQuant, software (GE Healthcare). FIG. 4C shows the percent of total band intensity of the furin-cleaved fragment at each time point. Furin cleaved SS1P reaches a maximum of slightly more than 30% of the sum of the intensity of all bands, while SS1-LR reaches a maximum of 6% of the total intensity. There is a greater than 5-fold difference between the proportions of cleaved SS1P and cleaved SS1-LR at each time point, suggesting that SS1-LR may be processed by furin less efficiently than SS1P.

Flexible Linker Mutants

Since our data suggest that SS1-LR is processed by furin less efficiently than SS1P, we tried to enhance the activity of SS1-LR by increasing its furin cleavage efficiency. We designed several mutants to explore whether changes to the furin cleavage site could enhance the activity of SS1-LR by improving the efficiency of intracellular furin cleavage. Our strategy was to increase the flexibility of the furin cleavage site, and thus its accessibility to furin, by the addition of short unstructured Gly/Ser linkers. SS1-LR/GGS (FIG. 1B) includes a Gly-Gly-Ser linker on the C-terminal end of the 11-residue furin cleavage site, and has enhanced activity on both the NCIH322M and KB31 cell lines (FIG. 5). Increasing the length of the linker (SS1-LR/GGSx2; FIG. 1B) does not enhance the activity further (data not shown). Duplication of the furin cleavage site with additional linker regions (SS1-2xFurin; FIG. 1B) also fails to enhance the activity beyond that of SS1-LR/GGS (data not shown). Unlike SS1-LR, all of the extended linker mutants demonstrate complete metabolic inhibition equivalent to the cyclohexamide control. Additionally, to confirm the importance of furin cleavage we prepared the mutant SS1-LR/GGS R279G, which includes the R279G mutation that renders furin unable to cleave the site. This mutant was completely inactive against both NCI-H322M and KB31 cells (FIG. 5), demonstrating the necessity of furin cleavage for activity.

We then tested our hypothesis that the GGS linker enhanced the furin cleavage efficiency of SS1-LR. Western blot analysis of A431/K5 cells treated with SS1-LR/GGS, however, showed no improvement in the proportion of cleaved relative to total RIT (data not shown). In vitro furin cleavage of SS1-LR/GGS likewise showed no improvement in the furin cleavage rate (data not shown). These results indicate that the improved cytotoxicity of SS1-LR/GGS is not due to enhanced furin cleavage, but is instead the result of a different mechanism. Possible explanations include the enhanced translocation of the toxin during intracellular trafficking.

Activity on Patient Cells

Figure 6:
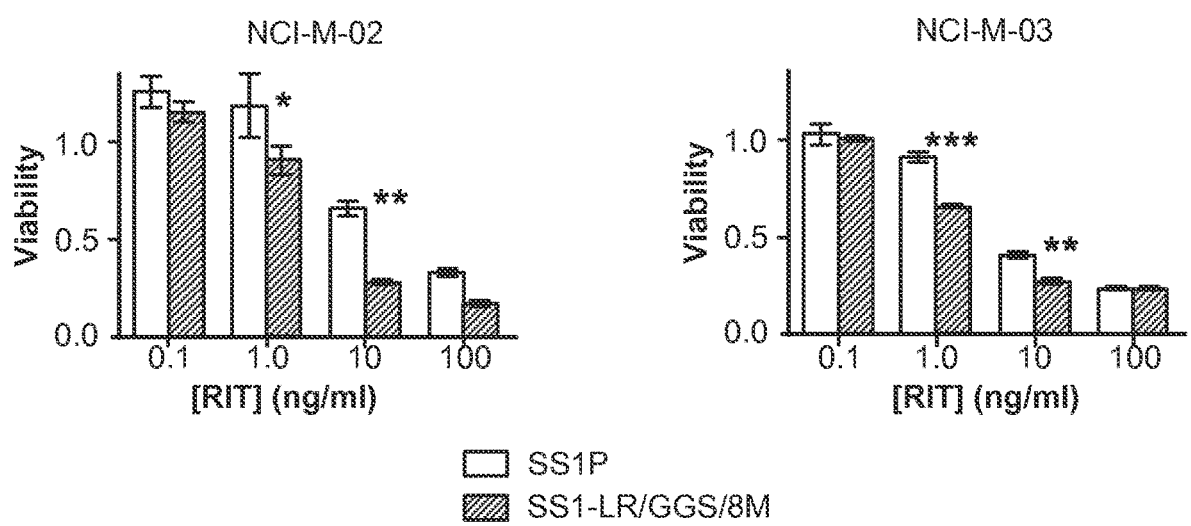
FIG. 6. Cytotoxicity of SS1-LR/GGS/8M on patient cells. Cells cultured from the pleural fluid or ascites of patients with mesothelioma were plated with increasing concentrations of RITs SS1P (white bar) or SS1-LR/GGS/8M (grey bar). After 4 days, cells were fixed and stained with crystal violet to detect intact cells. The resulting absorbance at 595 nm was normalized against an untreated control. The mean values and standard errors from three replicates are plotted. no asterisk=p>0.05; *=p<0.05; =p<0.01; *=p<0.001.

While this study was ongoing, a series of 8 point mutations in domain III was designed to reduce the immunogenicity of PE in patients treated with RITs by eliminating known B cell epitopes (Onda M et al., Submitted for publication to *PNAS.*). These mutations (D406A, R432G, R467A, R490A, R513A, E548S, Q592A, & K590S) do not influence the activity of RITs, but instead reduce the protein's immunogenicity. We incorporated these eight mutations into SS1-LR/GGS, making a new variant called SS1-LR/GGS/8M, and tested its cytotoxicity against primary cells taken from the pleural fluid or ascites of patients with mesothelioma. The fluid taken from patients contains a mixture of cells, not all of which are malignant, and they do not uniformly express mesothelin. Thus, the assay provides a good assessment of relative activity but is only a rough estimate of absolute cytotoxicity. Cells were treated at an early passage with various concentrations of SS1P or SS1-LR/GGS/8M and viability was assessed after four days by a crystal violet assay as described of several patient cells that were evaluated for response to SS1P, two (NCI-M-02 and NCI-M-03) showed a good response to treatment (>65% decrease in viability at the 100 ng/ml dose level). We assessed the activity of SS1P-LR/GGS/8M on these two populations and compared it to the activity of SS1P. The data are presented in FIG. 6 as fractional values of the untreated control value.

Both patient cells NCI-M-02 and NCI-M-03 were sensitive to treatment with either SS1P or SS1-LR/GGS/8M, showing a greater than 60% decrease in viability relative to the untreated control at doses of 100 ng/ml or lower. NCI-M-02 and NCI-M-03 were particularly sensitive to SS1-LR/GGS/8M at the 1.0 and 10 ng/ml dose levels, demonstrating significantly higher cytotoxicity when compared to SS1P at these concentrations (p<0.05). As controls, the patient cells were also treated with the RITs BL22 and HB21 (data not shown). BL22, which targets the B cell specific marker CD22, had no affect on the viability of either cell population at a dose of 100 ng/ml. HB21, which targets the ubiquitous transferrin receptor and is known to be extremely active on nearly all cells, reduced the viability of both cell lines by nearly 90% at a dose of 10 ng/ml. Overall, the data show that SS1-LR/GGS/8M had cytotoxicity similar to or better than SS1P on the two different patient cell populations. We conclude that the two anti-mesothelin immunotoxins, while not behaving identically, have comparable cytotoxic activity.

Example 2

Further, extended report on the construction, evaluation and contrast of SS1-LR/GGS/8M, a variant of SS1P with improved therapeutic properties. As discussed above, SS1-LR/GGS/8M incorporates mutations previously shown to improve RITs, as well as a new mutation that enhances its activity. SS1-LR is a truncated variant of SS1P that contains the catalytic fragment of PE joined to the SS1 Fv by the 11-residue PE furin cleavage site. The cytotoxicity of SS1-LR was evaluated on seven cell lines and found to be substantially lower than SS1P. Further analysis of SS1-LR in cultured cells indicated that it was poorly processed by furin during the intoxication pathway. To improve furin cleavage we introduced a 3-residue linker into SS1-LR, creating SS1-LR/GGS. SS1-LR/GGS was significantly more active on cell lines, but did not show enhanced furin cleavage. We introduced eight point mutations into the catalytic fragment of SS1-LR/GGS, which have been shown to decrease RIT immunogenicity by eliminating B cell epitopes. This new RIT, SS1-LR/GGS/8M, shows herein excellent anti-tumor activity, low nonspecific toxicity in rodents, and reduced reactivity with anti-SS1P human serum. Furthermore, primary cells from patients with mesothelioma shows enhanced responses to SS1-LR/GGS/8M relative to SS1P. SS1-LR/GGS/8M is a superior therapeutic candidate for clinical development due its low antigenicity, low nonspecific toxicity, and high activity.

Several mesothelin-positive human-derived cell lines were used in this study. These cells were generally sourced and grown as provided in Example 1.

Cytotoxicity Assays

Viability of cell lines treated with immunotoxins was measured using the Cell Counting Kit-8 WST-8 assay (Dojindo Molecular Technologies, Inc., Gaithersburg, Md.). Cells (2,000 cells/well) were plated in 96-well plates, left overnight to adhere, and incubated with varying concentrations of RITs for 72 hours at a final volume of 0.2 ml. At the end of the incubation period, 10 µl of the CCK-8 reagent was added to each well and the plates were incubated at 37° C. until the wells with the maximum absorbance at 450 nm reached values of ~1 OD. Values were normalized between controls of cyclohexamide (10 µg/ml) and buffer (Dulbecco's phosphate buffered saline without Ca and Mg (D-PBS; Quality Biological, Inc., Gaithersburg, Md.) containing 0.2% human serum albumin (HSA)), then fit to a sigmoidal equation with variable slopes for the plateau, baseline, and Hill slope using the GraphPad PRISM software (GraphPad Software, Inc., La Jolla, Calif.). The equation was subsequently used to interpolate the concentration of RIT which reduced cell viability to the 50% level ($EC_{50}$).

Cells from patients with mesothelioma were cultured and evaluated for their responses to SS1P and SS1-LR/GGS/8M essentially as described (Xiang X, et al., PLoS One 2011; 6:e14640.). D-PBS and 10 ng/ml HB21 (antitransferrin receptor/PE40) were used as negative and positive controls for cell death. Each condition was evaluated in triplicate. Statistical analysis of the resulting data by ANOVA was performed using the GraphPad Prism software.

Mouse Xenograft Antitumor Assay

Twenty-eight female nude mice were injected subcutaneously in the flank with $5 \times 10^6$ L55 cells in 0.2 ml RPMI with 4 mg/ml matrigel (BD Biosciences, San Jose, Calif.) on day 0. Tumor volume was measured regularly by caliper for the next 30 days. Seven days following implantation (~100 mm³ average tumor), mice were divided into four equal groups and intravenously injected on days 7, 9, and 12 with 0.2-ml of 0.2% HSA in D-PBS (vehicle) or vehicle containing either SS1P (0.4 mg/kg) or SS1-LR/GGS/8M (0.4 or 2.5 mg/kg). This experiment and all subsequent animal experiments were handled according to the National Institutes of Health guidelines approved by the Animal Care and Use Committee of the National Cancer Institute.

Mouse Serum Pharmacokinetics

Groups of nine female Balb/c mice were injected intravenously with 10 µg of SS1P or SS1-LR/GGS/8M in 0.2 ml D-PBS with 0.2% HSA. Groups of three mice were bled at time intervals of 2 and 20, 5 and 30, or 10 and 60 minutes. Sera were analyzed by enzyme-linked immunosorbent assay (ELISA) as previously described (Bang S, et al., *Clin Cancer Res* 2005; 11:1545-50.25)).

Rat Capillary Leak Assay

A previously described rat model of RIT-induced capillary leak syndrome (Siegall C B, et al., *Proc Natl Acad Sci USA* 1994; 91:9514-8.) was used to evaluate the nonspecific toxicity of SS1-LR/GGS/8M. Briefly, six- to eight-week-old female Wistar Furthand Rowett, nu/nu (athymic) rats (Harlan-Sprague-Dawley) were injected intravenously with D-PBS, SS1P (0.2 or 0.3 mg/kg), or SS1-LR/GGS/8M (6 or 12 mg/kg). After 24 hours, the rats were euthanized by exposure to $CO_2$. Hydrothorax fluid was collected from the euthanized animals by placing the carcass in dorsal recumbancy, removing the ventral chest wall, and aspirating fluid using a 3-ml syringe and 27.5-gauge needle. The lungs from several rats were removed, fixed for 3 days in 10% formalin, sectioned, and stained.

The RIT internalization assays were performed essentially as described above with samples being were analyzed by non-reducing western blot using a rabbit anti-PE38 polyclonal antibody.

Antigenicity Assay.

Binding of SS1P or SS1-LR/GGS/8M to antibodies in patient sera was analyzed essentially as described (Onda M, et al., *Proc Natl Acad Sci USA* 2011; 108:5742-7), except that CD22-rFc and HA22 were used for the detection of PE-specific antibodies by ELISA.

Results

In Vitro SS1-LR Activity.

The immunotoxin SS1P (FIG. 1) is the disulfide-stabilized two-chain anti-mesothelin SS1 Fv joined to PE38. We introduced the LR mutation ((Weldon J E, et al. *Blood* 2009; 113:3792-800); PE Δ251-273 & Δ285-394) into SS1P to create SS1-LR and evaluated its activity on seven mesothelinexpressing cell lines in vitro. Table 2 summarizes data from at least 3 separate cytotoxicity experiments as the average $EC_{50}$ values and standard error of the mean. Compared to SS1P, SS1-LR was more active on the HAY cell line, but less active on the remaining lines. The activity of SS1-LR varied widely among the different cell lines, but it was least active on the ovarian cancer lines.

304)) leads us to anticipate that SS1-LR will be less immunogenic than SS1P, the remaining elements of PE will nonetheless rapidly elicit neutralizing antibodies. To remove immunogenic B cell epitopes in PE, a series of eight point mutations in domain III has recently been designed (Onda M, et al., *Proc Natl Acad Sci USA* 2011; 108:5742-7.). These mutations (D406A, R432G, R467A, R490A, R513A, E548S, Q592A, & K590S) dramatically reduce the immunogenicity of HA22-LR in mice but do not greatly diminish its cytotoxicity. We incorporated the mutations into SS1-LR/GGS, making a new variant called SS1-LR/GGS/8M, and tested the RIT against seven mesothelin-expressing cell lines. The $EC_{50}$ values from these experiments are reported in Table 2. SS1-LR/GGS/8M is more active than SS1-LR and occasionally more active than SS1P(HAY, L55), but is less active than SS1-LR/GGS. The decrease in activity is especially apparent on the ovarian cancer lines.

Non-Specific Toxicity

In previous work with the anti-CD22 RIT HA22, we found that a single intravenous dose of 2 mg/kg HA22 was lethal to mice, while a dose of 20 mg/kg HA22-LR showed no toxicity (Weldon J E, et al., *Blood* 2009; 113:3792-800). We have since given single doses of HA22-LR as high as 45 mg/kg to mice without causing death (unpublished observations, data not shown), and we anticipated similar behavior from SS1-LR and its variants. Previous experiments placed the single-dose intravenous LD50 of SS1P at 1.0 mg/kg in Balb/C mice (Filpula D, et al., *Bioconjug Chem* 2007; 18:773-84) and 0.75 mg/kg in NIH Swiss mice (Onda M., et al., *Cancer Res* 2001; 61:5070-7). Using a QODx3 (administered three times every other day) dosing schedule similar to the clinical schedule, mice have tolerated a maximum dose of 0.4 mg/kg SS1P (unpublished observations, data not shown), but mice given SS1-LR have received doses up to 15 mg/kg QODx3 without toxicity (data not shown).

Although the decreased nonspecific toxicity of LR-based RITs in mice is intriguing, it may not be relevant to the major toxicities observed in clinical trials. RIT nonspecific toxicity in mice is the result of liver damage (Weldon J E, et al., *Blood* 2009; 113:3792-800; Onda M, et al., *J. Immunol.* 2000; 165:7150-6), which is not commonly observed in patients. A more relevant animal model of nonspecific

TABLE 2

| Cell Line | Cancer of Origin | $EC_{50}$ ± SEM (ng/ml) | | | | |
|---|---|---|---|---|---|---|
| | | SS1P | SS1-LR | SS1-LR/GGS | SS1-LR/GGS/8M | SS1-LR/GGS R279G |
| HAY | Mesothelioma | 2.24 ± 0.21 | 0.52 ± 0.07 | 0.10 ± 0.04 | 0.22 ± 0.02 | >1000 |
| M30 | Mesothelioma | 0.57 ± 0.07 | 3.70 ± 0.85 | 0.93 ± 0.18 | 1.46 ± 0.20 | >1000 |
| NCI-H322M | Lung adenocarcinoma | 0.30 ± 0.07 | 1.65 ± 0.23 | 0.18 ± 0.05 | 0.42 ± 0.09 | >1000 |
| L55 | Lung adenocarcinoma | 2.89 ± 0.43 | 6.67 ±1.27 | 1.08 ± 0.17 | 1.73 ± 0.31 | >1000 |
| OVCAR-8 | Ovarian carcinoma | 0.84 ± 0.21 | 49.1 ± 37.9 | 2.84 ± 1.43 | 14.4 ± 8.78 | >1000 |
| A1847 | Ovarian carcinoma | 1.01 ± 0.21 | 27.0 ± 8.70 | 2.73 ± 0.79 | 17.7 ± 7.13 | >1000 |
| A431/K5 | Epidermoid carcinoma | 0.044 ± 0.005 | 0.561 ± 0.198 | 0.199 ± 0.033 | 0.194 ± 0.038 | 15.12 ± 3.625 |

SS1-LR/GGS/8M

Figure 7:
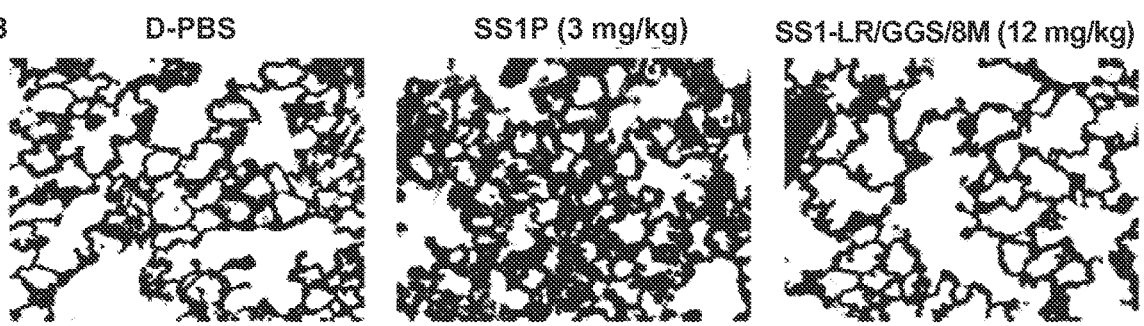
FIG. 7. In vivo behavior of SS1-LR/GGS/8M. A) Anti-tumor activity of SS1-LR/GGS/8M. Nude mice with L55 xenograft tumors were intravenously treated on days 7, 9, and 12 postimplantation with RIT buffer (0.2% HSA in D-PBS; crosses, solid line), 0.4 mg/kg SS1P (open circles, solid line), or SS1-LR/GGS/8M at doses of 0.4 (open squares, dashed line) or 2.5 (filled squares, dashed line) mg/kg. Arrows indicate days when treatment was administered. Tumor size was measured over the course of 30 days. Points represent the mean tumor size of all mice in the treatment group (n=7). Error bars indicate the standard error of each mean value. B) Rat model of capillary leak syndrome. Rats were treated intravenously with PBS, SS1P, or SS1-LR/GGS/8M, observed after 24 hours, and subsequently sacrificed. Thoracic fluid from the euthanized animals was collected and measured. The lungs of several rats were fixed, sectioned, and stained with hematoxylin and eosin. C) Representative pictures at 200× magnification are shown. D) Pharmacokinetics of SS1-LR/GGS/8M. BalbC mice were injected intravenously with 10 μg of either SS1P or SS1-LR/GGS/8M and bled at several intervals between 2 and 60 minutes from the time of injection. The concentration of immunotoxin in the serum at the various intervals was determined by ELISA and fit to a single exponential decay function. The corresponding half-life ($t_{1/2}$) is indicated. Each point is the concentration of immunotoxin in the serum of one mouse, and the concentration at each time interval was determined from at least two different mice.
Figure 7:
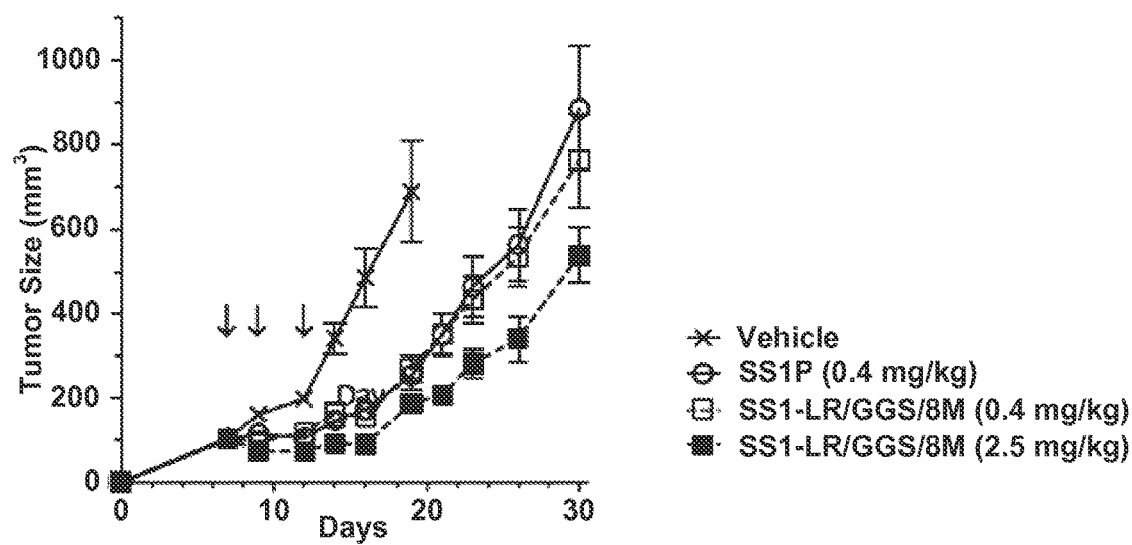
Figure 7:
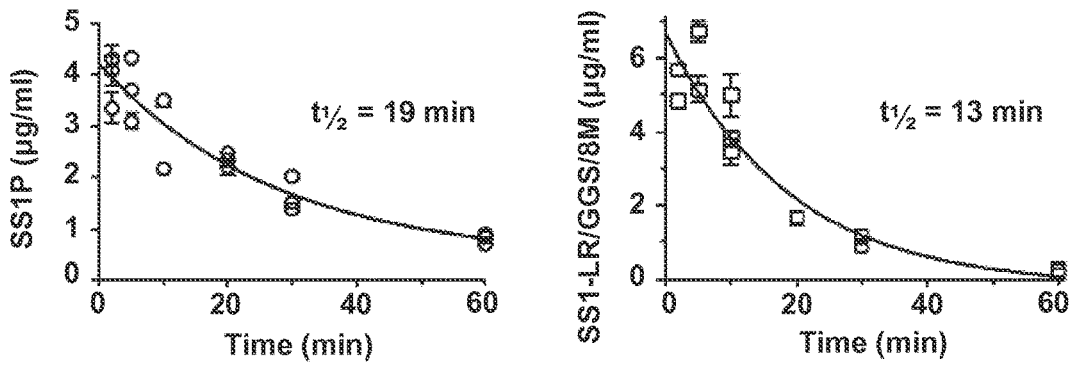

Immunogenicity remains a significant problem for PE-based RITs (Weldon J E, et al., *FEBS J.* 2011 December; 278(23):4683-700). Although work comparing HA22-LR with HA22 (Hansen J K, et al., *J Immunother* 2010; 33:297- toxicity is a RIT-induced capillary leak syndrome in rats (Siegall C B, et al., *Proc Natl Acad Sci USA* 1994; 91:9514-8., Siegall C B, et al., *Clin Cancer Res* 1997; 3:339-45). Capillary leak syndrome, in which fluid leaks from blood vessels into the interstitial space, is a common toxicity observed in clinical trials of PE-based RITs. Using this model, we observed that rats intravenously treated with 2 mg/kg SS1P appeared sick after 24 hours; they have labored breathing and fluid accumulation in their thoracic cavity (FIG. 7A). Increasing the dose of SS1P to 3 mg/kg increased the volume of thoracic fluid. In contrast, rats treated with either D-PBS or SS1-LR/GGS/8M showed no signs of illness and retained no fluid. Doses of 6 mg/kg and 12 mg/kg SS1-LR/GGS/8M were administered without observable effect. When the lungs of rats treated with D-PBS, SS1P, and SS1-LR/GGS/8M were fixed and stained, those treated with D-PBS or SS1-LR/GGS/8M appeared normal, while those from rats treated with SS1P showed signs of severe damage (FIG. 7B). Although no LR-based molecule has been tested clinically, this observation strengthens the proposition that the LR-based RITs may have decreased toxicity in patients.

In Vivo SS1-LR/GGS/8M Activity

We next evaluated the efficacy of SS1-LR/GGS/8M in vivo with a mouse xenograft tumor model using the L55 lung cancer cell line. Groups of seven nude mice with tumors averaging ~100 mm$^3$ were treated intravenously on days 7, 9, and 12 with SS1-LR/GGS/8M at doses of 0.4 and 2.5 mg/kg. For comparison, additional groups were treated intravenously on the same schedule with vehicle (0.2% HSA in D-PBS) or 0.4 mg/kg SS1P, the maximum tolerated dose of SS1P under this dosing schedule. The tumor size of each mouse was measured regularly for 30 days post-implantation (FIG. 7C).

The tumors of vehicle-treated mice grew to an average size of approximately 500 mm$^3$ on day 16 post-implantation. Mice treated with 0.4 mg/kg SS1P showed a brief delay in tumor growth that required until day 23 post-implantation for the tumors to reach approximately 500 mm$^3$ in size. We observed a nearly identical response in mice treated with 0.4 mg/kg SS1-LR/GGS/8M, suggesting parity between SS1P and SS1-LR/GGS/8M in this model. Although SS1P cannot be administered to mice on this schedule at doses higher than 0.4 mg/kg due to its nonspecific toxicity, SS1-LR/GGS/8M can be given to mice at much higher doses without ill effect. A ~6-fold higher dose of SS1-LR/GGS/8M (2.5 mg/kg) was tested in this tumor model. We observed significant (p<0.01 using a paired, two-tailed t test) tumor regression in this group of mice, whose tumors reached a minimum size of ~73 mm$^3$ on day 9. This group of mice also experienced enhanced tumor growth inhibition, reaching approximately 500 mm$^3$ in size on day 30 post-implantation.

Although SS1-LR/GGS/8M had activity equivalent to SS1P in the mouse L55 xenograft tumor model, it demonstrated enhanced activity relative to SS1P on L55 cells in vitro. This discrepancy in activity can be explained by a difference in mouse serum half-life between the two molecules. Previous work comparing the half-life of HA22-LR (~51 kDa) to HA22 (~63 kDa) in mice (Weldon J E, et al., Blood 2009; 113:3792-800.) showed that HA22-LR had an almost 2-fold shorter half-life than HA22 (7.8 and 14.6 minutes, respectively). We postulated that this difference was due to increased renal filtration of the smaller molecule, and we anticipated a similar result when comparing SS1-LR/GGS/8M (~50 kDa) to SS1P (~63 kDa). An analysis of serum samples taken from mice injected with SS1-LR/GGS/8M showed a half-life of 13 minutes compared to a half-life of 19 minutes for SS1P (FIG. 7D). We conclude that the difference in the half-life between SS1-LR/GGS/8M and SS1P accounts for the discrepancy in relative activity between the two molecules in vitro and in vivo.

Antigenicity of SS1-LR/GGS/8M

Figure 8:
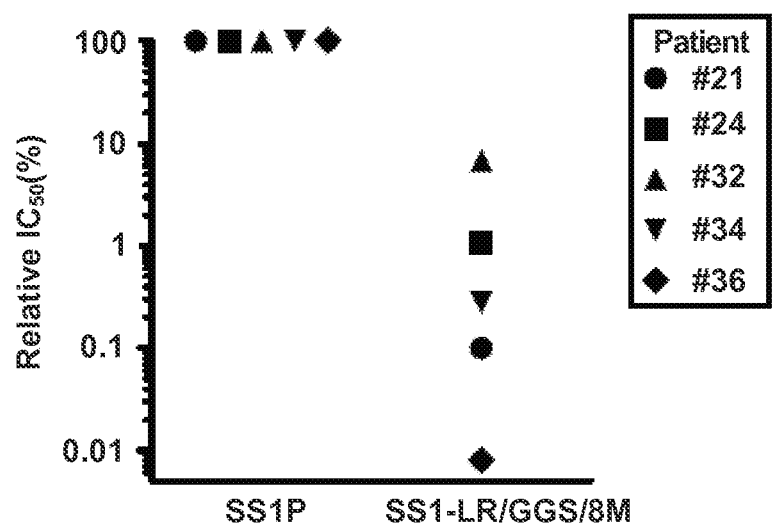
FIG. 8. Human antigenicity of SS1-LR/GGS/8M. The reactivity of SS and SS1-LR/GGS/8M with preexisting antibodies in human sera was compared using a displacement assay to determine the concentration at which the two RITs reduced the signal of an ELISA to detect serum antibodies by 50% (IC50). The relative $IC_{50}$ values of SS1P to SS1-LR/GGS/8M are plotted here. The antigenicity of SS1-LR/GGS/8M is dramatically reduced relative to SS1P for all sera.

Based on previous studies with the RIT HA22 (Onda M, et al., Proc Natl Acad Sci USA 2011; 108:5742-7), we anticipated that the mutations in SS1-LR/GGS/8M would remove B cell epitopes from SS1P. In order to evaluate this proposition, we compared the reactivity of SS1P and SS1-LR/GGS/8M with serum from five patients who had developed neutralizing antibodies in response to treatment with SS1P. Patient serum was initially mixed with either SS1P or SS1-LR/GGS/8M. Subsequently, unbound PE38-specific antibodies in the serum were detected using an ICC-ELISA (Onda M, et al., Proc Natl Acad Sci USA 2011; 108:5742-7). From these data, the concentrations of SS1P and SS1-LR/GGS/8M at which the ELISA signal was reduced by 50% ($IC_{50}$) were determined. As previously reported (Onda M, et al., J Immunol 2006; 177:8822-34), the $IC_{50}$ values correlate with the affinity of the antibody-antigen interaction. The $IC_{50}$ values of SS1P relative to SS1-LR/GGS/8M are plotted as percentages in FIG. 8. For all patient sera, the ratios of SS1P to SS1-LR/GGS/8M $IC_{50}$ values were substantially below 10%, indicating that the major fraction of SS1P-reactive antibodies in the sera were unreactive with SS1-LR/GGS/8M.

Activity on Patient Cells

To complement our assessment of SS1-LR/GGS/8M on cells lines in vitro and in vivo, we further tested its activity against primary cells obtained from the pleural fluid or ascites of patients with mesothelioma and maintained in culture for several passages. Since the fluid taken from patients contains a mixture of cells, the assay provides a good assessment of relative activity but is only a rough estimate of absolute cytotoxicity. Cells from two additional patients were treated with various concentrations of SS1P, and their viability was assessed after four days using a crystal violet assay. The early passage mesothelioma patient cells NCI-M-16, and NCI-M-19 showed clear responses to treatment with SS1P (>75% decrease in viability at the 100 ng/ml dose level). We evaluated the activity of SS1P-LR/GGS/8M on these two additional patient derived cell populations. The data are presented in FIG. 9 as fractional values normalized between control treatments of D-PBS (100% viable) and 10 ng/ml of the anti-transferrin receptor/PE40 RIT HB21 (0% viable). All patient cell populations were extremely sensitive to treatment with SS1P-LR/GGS/8M, demonstrating significantly enhanced cytotoxicity over SS1P.

SS1P is an anti-mesothelin recombinant immunotoxin based on Pseudomonas exotoxin A that is currently in clinical development for the treatment of mesothelioma, but with the potential to treat a variety of solid tumors that express mesothelin. In clinical trials, SS1P has achieved modest yet encouraging outcomes. Its efficacy, however, has been restricted by dose-limiting toxicities and the rapid generation of neutralizing antibodies in patients. Here we report that SS1-LR/GGS/8M, a variant of SS1P with low antigenicity, has excellent activity, and markedly reduced nonspecific toxicity in rodents.

SS1-LR/GGS/8M is as a highly active, less toxic, and less antigenic variant of the PE-based anti-mesothelin RIT SS1P. Our initial evaluation of SS1-LR showed highly variable, but generally low activity on a selection of mesothelin-expressing cell lines in vitro (Tables 1 & 2). While exploring reasons for its low activity relative to SS1P, we studied the internalization and processing of SS1-LR and found that the proportion of furin cleaved SS1-LR was much lower than that of SS1P in cells treated with the two RITs. This suggested that decreased furin cleavage could be limiting the activity of SS1-LR, and we designed and produced several mutants to test this hypothesis. The addition of a short Gly-Gly-Ser linker after the furin cleavage site did not enhance furin cleavage, but did enhance the activity of SS1-LR on cell lines. By combining SS1-LR with the GGS linker and an additional eight point mutations that have been shown to reduce the immunogenicity of PE, we generated our final molecule, SS1-LR/GGS/8M. Compared to SS1P, SS1-LR/GGS/8M demonstrated greatly reduced nonspecific toxicity in a rat capillary leak model, enhanced cytotoxicity against patient cells, and reduced reactivity with antibodies in patient sera. Initial experiments with SS1-LR demonstrated variable cytotoxicity relative to SS1P on cell lines. The primary tendency, however, was toward a less active molecule. SS1-LR was more active on the HAY line, and less active on the other six lines. This trend is remarkably different from the anti-CD22 version of the LR molecule, HA22-LR, which demonstrated similar or enhanced cytotoxicity on most cell lines and patient cells (Weldon J E, et al., *Blood* 2009; 113:3792-800). This discrepancy suggest that there is an intrinsic difference between the intoxication pathway of PE targeted to mesothelin on epithelial cells and PE targeted to CD22 on B cells.

Regarding the generally decreased activity of SS1-LR relative to SS1P, one possible explanation for this disparity is a difference in the intracellular intoxication pathway. The LR variant of PE38 contains extensive deletions in domain II and Ib of PE, and these deletions might have negatively affected the ability of PE to traffic to the cytosol. Our experiments to detect full-length and processed PE in lysates of A431/K5 cells treated with SS1P and SS1-LR showed a dramatic difference in the amount of furin-processed RIT. A large fraction of the total RIT in SS1P-treated cells was processed, but only a small fraction of the total RIT was cleaved in SS1-LR-treated cells. This result suggested that poor furin cleavage might be limiting the activity of SS1-LR, and we set out to improve this step of the PE intoxication pathway.

By appending a flexible linker to the SS1-LR furin site, we produced a more active RIT, but we could not demonstrate enhanced furin cleavage. The addition of a short Gly-Gly-Ser linker (SS1-LR/GGS, FIG. 1), a longer linker (SS1-LR/GGSx2, FIG. 1), or a repeat of the furin site flanked by short Gly-Gly-Ser linkers (SS1-LR/2xFurin, FIG. 1) all granted a modest cytotoxicity increase. None of these molecules, however, enhanced the proportion of furin cleaved SS1-LR in treated A431/K5 cells or increased the rate of furin cleavage in vitro (data not shown). We concluded that the addition of a linker must enhance cytotoxicity through another mechanism, perhaps related to intracellular trafficking or enhanced toxin stability, and we are continuing to explore these possibilities. Our experiments also demonstrated the necessity of furin cleavage in the cytotoxicity of SS1P. A point mutation in SS1-LR/GGS that changed an arginine essential for cleavage to glycine (SS1-LR/GGS R279G, FIG. 1) produced a protein that was not cleaved by furin. This RIT showed extremely poor activity on all cells, with negligible activity at concentrations of 120 µg/ml on six of the seven cell lines tested. The uncleavable mutant shows an EC50 below 1 µg/ml only on A431/K5 cells (Table 2), but its activity was severely impaired nonetheless. In addition, the artificially high expression of mesothelin in this cell line may not be representative of those lines that naturally express mesothelin. The necessity of furin cleavage in the PE intoxication pathway has recently been questioned (Morlon-Guyot J, et al., *Infect Immun* 2009; 77:3090-9), but much evidence exists that furin performs an important role during intoxication (Ornatowski W, et al.; *J Clin Invest* 2007; 117:3489-97; Shiryaev S A, et al., *J Biol Chem* 2007; 282:20847-53; Sarac M S, et al., *Infect Immun* 2002; 70:7136-9; Chiron M F, et al., *J Biol Chem* 1997; 272:31707-11; Gu M, et al., *Infect Immun* 1996; 64:524-7; Inocencio N M, et al., *J Biol Chem* 1994; 269:31831-5; and Moehring J M, et al., *J Biol Chem* 1993; 18:2590-4). In the case presented here, PE intoxication generally fails without a site suitable for furin processing.

Our laboratory has recently produced a RIT, HA22-LR-8M, which has extremely low immunogenicity due to the elimination of B cell epitopes (Onda M, et al., *Proc Natl Acad Sci USA* 2011; 108:5742-7). HA22-LR-8M contains the LR variant deletions of PE and an additional eight point mutations in domain III. These mutations were placed into SS1P, generating SS1-LR/GGS/8M. Since the bulk of the immune response to RITs is directed at PE, we expect SS1-LR/GGS/8M to exhibit similarly reduced immunogenicity. To confirm that SS1-LR/GGS/8M indeed removes human B cell epitopes from SS1P, we examined the reactivity of SS1-LR/GGS/8M with sera from patients who developed neutralizing antibodies while undergoing treatment with SS1P. In the five cases we tested, SS1-LR/GGS/8M showed dramatically reduced antigenicity compared to SS1P. This result is consistent with observations of HA22 and HA22-LR/8M (Onda M, et al., *Proc Natl Acad Sci USA* 2011; 108:5742-7), and indicates that we have identified and removed many of the immunogenic epitopes in PE-based RITs.

The cytotoxicity of SS1-LR/GGS/8M was evaluated in several cell lines, a mouse tumor model, and primary cells from patients with mesothelioma. SS1-LR/GGS/8M demonstrated excellent cytotoxicity relative to SS1P in the lung cancer and mesothelioma cell lines, but was poorly active on the ovarian cancer lines. This result is unexpected, since the ovarian lines were sensitive to SS1-LR/GGS, and indicates that the eight point mutations in the catalytic domain of PE may be interfering with the activity of SS1-LR/GGS/8M. In the mouse tumor model, L55 xenograft tumors responded similarly to SS1-LR/GGS/8M and SS1P, although higher doses of SS1-LR/GGS/8M could be administered to enhance the anti-tumor effect. Finally, when tested against primary malignant cells from patients with mesothelioma, SS1-LR/GGS/8M exhibited remarkably enhanced cytotoxicity over SS1P. Overall, our evaluation of SS1-LR/GGS/8M showed excellent cytotoxic activity.

In addition to high activity and low antigenicity, SS1-LR/GGS/8M showed decreased nonspecific toxicity relative to SS1P. The rat model for RIT-induced capillary leak syndrome effectively demonstrates this difference. There were no significant differences between rats treated with PBS and those treated with SS1-LR/GGS/8M, while rats treated with SS1P developed debilitating fluid accumulation in the lungs. Capillary leak syndrome (also called vascular leak syndrome) occurs when fluid leaks from capillaries, leading to a fall in serum albumin, fluid retention, edema, and weight gain. This toxicity has been frequently observed in patients treated with a variety of immunotoxins, including those based on PE, and presumably results from off-target endothelial cell damage. Limiting the untargeted toxicity of RITs can potentially enhance their efficacy by allowing higher doses to be administered safely. This experiment, along with the others described here, suggests that SS1-LR/GGS/8M would be an excellent candidate for the clinic. The low antigenicity, low nonspecific toxicity, and high cytotoxicity of SS1-LR/GGS/8M are highly promising for the future development of antimesothelin RITs.

It is understood that the examples and embodiments described herein are for illustrative purposes only and that various modifications or changes in light thereof will be suggested to persons skilled in the art and are to be included within the spirit and purview of this application and scope of the appended claims. All accession numbers, publications, patents, and patent applications cited herein are hereby incorporated by reference in their entirety for all purposes.

What is claimed is:

1. A chimeric molecule comprising a fusion polypeptide having the formula M-L1-FCS-FL-functional PE domain III, wherein
M is an antibody which specifically binds to mesothelin, or a fragment thereof that specifically binds mesothelin;
L1 consists of from 1 to 10 continuous amino acid residues selected independently from glycine and serine;
FCS is a furin cleavage site consisting of the amino acid sequence of (a) SEQ ID NO: 17, (b) SEQ ID NO: 29, (c) a truncated version of (a) capable of being cleaved by furin and comprising the amino acid sequence of RQPR (SEQ ID NO: 39), (d) a truncated version of (b) capable of being cleaved by furin and comprising the amino acid sequence of RSKR (SEQ ID NO: 44), or any one of SEQ ID NOs: 30-38 and 74;

FL consists of from 3 to 8 continuous amino acid residues selected independently from glycine and serine;

Functional PE domain III consists of continuous amino acid residues identical in sequence to SEQ ID NO:1 from position 395 to 613, optionally comprising (i) substitutions in one or more residues corresponding to 609-613 of SEQ ID NO:1, (ii) a substitution of glycine, alanine, valine, leucine, or isoleucine for arginine at a position corresponding to position 490 of SEQ ID NO:1, (iii) a substitution of, independently, alanine, glycine, serine or glutamine in place of one or more residues corresponding to residues D403, D406, R412, R427, E431, R432, R458, D461, R467, R490, R505, R513, E522, R538, E548, R551, R576, K590, Q592, and L597 of SEQ ID NO:1, or (iv) a combination of any of (i)-(iii), wherein the chimeric molecule provides an increased cytotoxicity for cells expressing mesothelin as compared to the chimeric molecule with cysteine residues flanking the FCS.

2. The molecule of claim 1, wherein the antibody or antibody fragment is a minibody, a diabody, a triabody, an Fab' fragment, an $F(ab)'_2$ fragment, a single chain Fv protein ("scFv"), or a disulfide stabilized Fv protein ("dsFv") fragment.

3. The molecule of claim 1, wherein the antibody or antibody fragment comprises disulfide stabilized light and heavy chain immunoglobulin variable regions fused to the remainder of the molecule through linkage of the heavy chain to L1.

4. The molecule of claim 1, wherein the antibody or antibody fragment comprises:

a $V_H$ chain comprising a CDR1 amino acid sequence of GYTMN (SEQ ID NO:51), a CDR2 amino acid sequence of LITPYNGASSYNQKFRG (SEQ ID NO:52), and a CDR3 amino acid sequence of GGYDGRGFDY (SEQ ID NO:53), and a $V_L$ chain comprising a CDR1 amino acid sequence of SASSSVSYMH (SEQ ID NO:54), a CDR2 amino acid sequence of DTSKLAS (SEQ ID NO:55), and a CDR3 amino acid sequence selected from the group consisting of QQWSGYPLT (SEQ ID NO:56), QQWSKHPLT (SEQ ID NO:57), QQWSGHPLT (SEQ ID NO:58), QQWSAHPLT (SEQ ID NO:59), QQWSQIPLT (SEQ ID NO:60), QQWGFNPLT (SEQ ID NO:61), QQWGTNPLT (SEQ ID NO:62), QQWGSHPLT (SEQ ID NO:63), QQWGDFPLT (SEQ ID NO:64), QQWGDHPLT (SEQ ID NO:65), QQWSAHPLT (SEQ ID NO:66), and QQWSGYPTT (SEQ ID NO:67).

5. The molecule of claim 4, wherein the $V_L$ CDR3 amino acid sequence is QQWSKHPLT (SEQ ID NO:57).

6. The molecule of claim 1, wherein L1 is 3 to 5 amino acids in length.

7. The molecule of claim 1, wherein the PE domain III has a substitution of alanine, glycine or serine in place of at least one amino acid residue corresponding to an amino acid residue of SEQ ID NO:1 selected from the group consisting of D403, R412, R427, E431, R458, D461, R505, E522, R538, R551, R576 and L597.

8. The molecule of claim 1, wherein the PE domain III has a substitution of alanine, glycine or serine in place of at least one amino acid residue corresponding to an amino acid residue of SEQ ID NO:1 selected from the group consisting of D406, R432, R467, R490, R513, E548, K590 and Q592.

9. The molecule of claim 1, wherein the FL is GGS, $(GGS)_2$ (SEQ ID NO:18), GSGG (SEQ ID NO:71), GGSGG (SEQ ID NO:72), GGSG (SEQ ID NO:73), GSG, or GGG.

10. The molecule of claim 1, wherein FL is GGS.

11. The molecule of claim 1, wherein the furin cleavage sequence is RHRQPRGWEQL (SEQ ID NO:17).

12. The molecule of claim 1, wherein the PE functional Domain III is the amino acid sequence of SEQ ID NO:4 from position 20 to 237 or of SEQ ID NO:5 from position 20 to 237.

13. The molecule of claim 1, wherein the molecule comprises a disulfide stabilized SS1 variable light chain of SEQ ID NO: 6 and SS1 variable heavy chain sequence of SEQ ID NO:7.

14. The molecule of claim 1, wherein the molecule comprises the SS1 variable light chain of SEQ ID NO: 6 and the SS1 variable heavy chain-PE fusion polypeptide of SEQ ID NO:8 wherein the variable light and heavy chains form a disulfide stabilized antibody.

15. The molecule of claim 1, wherein the FCS is identical in sequence to SEQ ID NO:1 from position 274 to 284 or of the amino acid sequence RHRSKRGWEQL (SEQ ID NO:29).

16. A pharmaceutical composition comprising the molecule of claim 1 and a pharmaceutically acceptable excipient.

17. A nucleic acid encoding the molecule of claim 1.

18. A vector comprising the nucleic acid of claim 17.

19. A host cell comprising the nucleic acid of claim 17.

20. A method of treating a cancer which overexpresses mesothelin in a subject in need thereof, comprising administering the chimeric molecule of claim 1 to the subject.

21. The method of claim 20, wherein the cancer is a lung adenocarcinoma, an ovarian carcinoma, mesothelioma and/or epidermoid carcinoma.

22. The molecule of claim 1, wherein FL consists of 3 continuous amino acid residues selected independently from glycine and serine.

23. The molecule of claim 1, wherein FL consists of 4 continuous amino acid residues selected independently from glycine and serine.

24. The molecule of claim 1, wherein FL consists of 5 continuous amino acid residues selected independently from glycine and serine.

25. The molecule of claim 1, wherein FL consists of 6 continuous amino acid residues selected independently from glycine and serine.

26. The molecule of claim 1, wherein FL consists of 7 continuous amino acid residues selected independently from glycine and serine.

27. The molecule of claim 1, wherein L1 consists of 3 amino acid residues.

* * * * *

SEQUENCE LISTING

```
<160> NUMBER OF SEQ ID NOS: 73

<210> SEQ ID NO 1
<211> LENGTH: 613
<212> TYPE: PRT
<213> ORGANISM: Pseudomonas aeruginosa

<400> SEQUENCE: 1

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
                20                  25                  30

Ala Ile Ala Asp Thr Asn Gly Gln Gly Val Leu His Tyr Ser Met Val
            35                  40                  45

Leu Glu Gly Gly Asn Asp Ala Leu Lys Leu Ala Ile Asp Asn Ala Leu
        50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
                100                 105                 110

Ile Lys Val Phe Ile His Glu Leu Asn Ala Gly Asn Gln Leu Ser His
            115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
                180                 185                 190

Gly Lys Val Leu Cys Leu Leu Asp Pro Leu Asp Gly Val Tyr Asn Tyr
            195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
                260                 265                 270

Thr Arg His Arg Gln Pro Arg Gly Trp Glu Gln Leu Glu Gln Cys Gly
            275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335
```

-continued

```
Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610

<210> SEQ ID NO 2
<211> LENGTH: 230
<212> TYPE: PRT
<213> ORGANISM: Artificial Sequence
<220> FEATURE:
<223> OTHER INFORMATION: synthetic Pseudomonas exotoxin A with reduced
      immunogenicity
<220> FEATURE:
<221> NAME/KEY: VARIANT
<222> LOCATION: (1)..(230)
<223> OTHER INFORMATION: Xaa = Gly, Ala or Ser

<400> SEQUENCE: 2

Arg His Arg Gln Pro Arg Gly Trp Glu Gln Leu Pro Thr Gly Ala Glu
1               5                   10                  15

Phe Leu Gly Asp Gly Gly Xaa Val Ser Phe Ser Thr Arg Gly Thr Gln
            20                  25                  30

Asn Trp Thr Val Glu Arg Leu Leu Gln Ala His Arg Gln Leu Glu Glu
        35                  40                  45

Xaa Gly Tyr Val Phe Val Gly Tyr His Gly Thr Phe Leu Glu Ala Ala

-continued

```
            50                  55                  60
Gln Ser Ile Val Phe Gly Gly Val Arg Ala Arg Ser Gln Asp Leu Asp
 65                  70                  75                  80

Ala Ile Trp Xaa Gly Phe Tyr Ile Ala Gly Asp Pro Ala Leu Ala Tyr
                 85                  90                  95

Gly Tyr Ala Gln Asp Gln Glu Pro Asp Ala Xaa Gly Arg Ile Arg Asn
            100                 105                 110

Gly Ala Leu Leu Arg Val Tyr Val Pro Arg Ser Ser Leu Pro Gly Phe
        115                 120                 125

Tyr Xaa Thr Ser Leu Thr Leu Ala Ala Pro Glu Ala Ala Gly Glu Val
    130                 135                 140

Glu Arg Leu Ile Gly His Pro Leu Pro Leu Arg Leu Asp Ala Ile Thr
145                 150                 155                 160

Gly Pro Glu Glu Xaa Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
            180                 185                 190

Arg Asn Val Gly Gly Asp Leu Asp Pro Ser Ser Ile Pro Asp Xaa Glu
        195                 200                 205

Xaa Ala Ile Ser Ala Leu Pro Asp Tyr Ala Ser Gln Pro Gly Lys Pro
    210                 215                 220

Pro Arg Glu Asp Leu Lys
225                 230

<210> SEQ ID NO 3
<211> LENGTH: 233
<212> TYPE: PRT
<213> ORGANISM: Artificial Sequence
<220> FEATURE:
<223> OTHER INFORMATION: synthetic modified Pseudomonas exotoxin A
      PE-LR/GGS/8M

<400> SEQUENCE: 3

Arg His Arg Gln Pro Arg Gly Trp Glu Gln Leu Gly Gly Ser Pro Thr
 1               5                  10                  15

Gly Ala Glu Phe Leu Gly Asp Gly Gly Ala Val Ser Phe Ser Thr Arg
                20                  25                  30

Gly Thr Gln Asn Trp Thr Val Glu Arg Leu Leu Gln Ala His Arg Gln
            35                  40                  45

Leu Glu Glu Gly Gly Tyr Val Phe Val Gly Tyr His Gly Thr Phe Leu
        50                  55                  60

Glu Ala Ala Gln Ser Ile Val Phe Gly Gly Val Arg Ala Arg Ser Gln
 65                  70                  75                  80

Asp Leu Asp Ala Ile Trp Ala Gly Phe Tyr Ile Ala Gly Asp Pro Ala
                 85                  90                  95

Leu Ala Tyr Gly Tyr Ala Gln Asp Gln Glu Pro Asp Ala Ala Gly Arg
            100                 105                 110

Ile Arg Asn Gly Ala Leu Leu Arg Val Tyr Val Pro Arg Ser Ser Leu
        115                 120                 125

Pro Gly Phe Tyr Ala Thr Ser Leu Thr Leu Ala Ala Pro Glu Ala Ala
    130                 135                 140

Gly Glu Val Glu Arg Leu Ile Gly His Pro Leu Pro Leu Arg Leu Asp
145                 150                 155                 160

Ala Ile Thr Gly Pro Glu Glu Ser Gly Gly Arg Leu Glu Thr Ile Leu
                165                 170                 175
```

```
Gly Trp Pro Leu Ala Glu Arg Thr Val Val Ile Pro Ser Ala Ile Pro
            180                 185                 190

Thr Asp Pro Arg Asn Val Gly Gly Asp Leu Asp Pro Ser Ser Ile Pro
        195                 200                 205

Asp Ser Glu Ala Ala Ile Ser Ala Leu Pro Tyr Ala Ser Gln Pro
    210                 215                 220

Gly Lys Pro Pro Arg Glu Asp Leu Lys
225                 230
```

<210> SEQ ID NO 4
<211> LENGTH: 238
<212> TYPE: PRT
<213> ORGANISM: Artificial Sequence
<220> FEATURE:
<223> OTHER INFORMATION: synthetic modified Pseudomonas exotoxin A
      PE-LR/FL/8X
<220> FEATURE:
<221> NAME/KEY: VARIANT
<222> LOCATION: (12)..(14)
<223> OTHER INFORMATION: Xaa = Gly or Ser
<220> FEATURE:
<221> NAME/KEY: VARIANT
<222> LOCATION: (15)..(19)
<223> OTHER INFORMATION: Xaa = Gly or Ser, may be present or absent
<220> FEATURE:
<221> NAME/KEY: VARIANT
<222> LOCATION: (20)..(230)
<223> OTHER INFORMATION: Xaa = Gly, Ala or Ser

<400> SEQUENCE: 4

```
Arg His Arg Gln Pro Arg Gly Trp Glu Gln Leu Xaa Xaa Xaa Xaa Xaa
1               5                   10                  15

Xaa Xaa Xaa Pro Thr Gly Ala Glu Phe Leu Gly Asp Gly Gly Xaa Val
            20                  25                  30

Ser Phe Ser Thr Arg Gly Thr Gln Asn Trp Thr Val Glu Arg Leu Leu
            35                  40                  45

Gln Ala His Arg Gln Leu Glu Glu Xaa Gly Tyr Val Phe Val Gly Tyr
50                  55                  60

His Gly Thr Phe Leu Glu Ala Ala Gln Ser Ile Val Phe Gly Gly Val
65                  70                  75                  80

Arg Ala Arg Ser Gln Asp Leu Asp Ala Ile Trp Xaa Gly Phe Tyr Ile
                85                  90                  95

Ala Gly Asp Pro Ala Leu Ala Tyr Gly Tyr Ala Gln Asp Gln Glu Pro
            100                 105                 110

Asp Ala Xaa Gly Arg Ile Arg Asn Gly Ala Leu Leu Arg Val Tyr Val
        115                 120                 125

Pro Arg Ser Ser Leu Pro Gly Phe Tyr Xaa Thr Ser Leu Thr Leu Ala
    130                 135                 140

Ala Pro Glu Ala Ala Gly Glu Val Glu Arg Leu Ile Gly His Pro Leu
145                 150                 155                 160

Pro Leu Arg Leu Asp Ala Ile Thr Gly Pro Glu Glu Xaa Gly Gly Arg
                165                 170                 175

Leu Glu Thr Ile Leu Gly Trp Pro Leu Ala Glu Arg Thr Val Val Ile
            180                 185                 190

Pro Ser Ala Ile Pro Thr Asp Pro Arg Asn Val Gly Gly Asp Leu Asp
        195                 200                 205

Pro Ser Ser Ile Pro Asp Xaa Glu Xaa Ala Ile Ser Ala Leu Pro Asp
    210                 215                 220

Tyr Ala Ser Gln Pro Gly Lys Pro Pro Arg Glu Asp Leu Lys
225                 230                 235
```

<210> SEQ ID NO 5
<211> LENGTH: 238
<212> TYPE: PRT
<213> ORGANISM: Artificial Sequence
<220> FEATURE:
<223> OTHER INFORMATION: synthetic modified Pseudomonas exotoxin A
      PE-LR/FL/8M
<220> FEATURE:
<221> NAME/KEY: VARIANT
<222>

```
Gly Glu Lys Val Thr Met Thr Cys Ser Ala Ser Ser Ser Val Ser Tyr
            20                  25                  30

Met His Trp Tyr Gln Gln Lys Ser Gly Thr Ser Pro Lys Arg Trp Ile
        35                  40                  45

Tyr Asp Thr Ser Lys Leu Ala Ser Gly Val Pro Gly Arg Phe Ser Gly
    50                  55                  60

Ser Gly Ser Gly Asn Ser Tyr Ser Leu Thr Ile Ser Ser Val Glu Ala
65                  70                  75                  80

Glu Asp Asp Ala Thr Tyr Tyr Cys Gln Gln Trp Ser Lys His Pro Leu
                85                  90                  95

Thr Phe Gly Cys Gly Thr Lys Leu Glu Ile Lys
            100                 105
```

<210> SEQ ID NO 7
<211> LENGTH: 355
<212> TYPE: PRT
<213> ORGANISM: Artificial Sequence
<220> FEATURE:
<223> OTHER INFORMATION: synthetic anti-mesothelin monoclonal antibody
      recombinant immunotoxin SS1-LR variable heavy chain (VH-PE)

<400> SEQUENCE: 7

```
Met Gln Val Gln Leu Gln Gln Ser Gly Pro Glu Leu Glu Lys Pro Gly
1               5                   10                  15

Ala Ser Val Lys Ile Ser Cys Lys Ala Ser Gly Tyr Ser Phe Thr Gly
            20                  25                  30

Tyr Thr Met Asn Trp Val Lys Gln Ser His Gly Lys Cys Leu Glu Trp
        35                  40                  45

Ile Gly Leu Ile Thr Pro Tyr Asn Gly Ala Ser Ser Tyr Asn Gln Lys
    50                  55                  60

Phe Arg Gly Lys Ala Thr Leu Thr Val Asp Lys Ser Ser Ser Thr Ala
65                  70                  75                  80

Tyr Met Asp Leu Leu Ser Leu Thr Ser Glu Asp Ser Ala Val Tyr Phe
                85                  90                  95

Cys Ala Arg Gly Gly Tyr Asp Gly Arg Gly Phe Asp Tyr Trp Gly Gln
            100                 105                 110

Gly Thr Thr Val Thr Val Ser Ser Lys Ala Ser Gly Gly Arg His Arg
        115                 120                 125

Gln Pro Arg Gly Trp Glu Gln Leu Pro Thr Gly Ala Glu Phe Leu Gly
    130                 135                 140

Asp Gly Gly Asp Val Ser Phe Ser Thr Arg Gly Thr Gln Asn Trp Thr
145                 150                 155                 160

Val Glu Arg Leu Leu Gln Ala His Arg Gln Leu Glu Glu Arg Gly Tyr
                165                 170                 175

Val Phe Val Gly Tyr His Gly Thr Phe Leu Glu Ala Ala Gln Ser Ile
            180                 185                 190

Val Phe Gly Gly Val Arg Ala Arg Ser Gln Asp Leu Asp Ala Ile Trp
        195                 200                 205

Arg Gly Phe Tyr Ile Ala Gly Asp Pro Ala Leu Ala Tyr Gly Tyr Ala
    210                 215                 220

Gln Asp Gln Glu Pro Asp Ala Arg Gly Arg Ile Arg Asn Gly Ala Leu
225                 230                 235                 240

Leu Arg Val Tyr Val Pro Arg Ser Ser Leu Pro Gly Phe Tyr Arg Thr
                245                 250                 255

Ser Leu Thr Leu Ala Ala Pro Glu Ala Ala Gly Glu Val Glu Arg Leu
            260                 265                 270
```

Ile Gly His Pro Leu Pro Leu Arg Leu Asp Ala Ile Thr Gly Pro Glu
            275                 280                 285

Glu Glu Gly Gly Arg Leu Glu Thr Ile Leu Gly Trp Pro Leu Ala Glu
        290                 295                 300

Arg Thr Val Val Ile Pro Ser Ala Ile Pro Thr Asp Pro Arg Asn Val
305                 310                 315                 320

Gly Gly Asp Leu Asp Pro Ser Ser Ile Pro Asp Lys Glu Gln Ala Ile
                325                 330                 335

Ser Ala Leu Pro Asp Tyr Ala Ser Gln Pro Gly Lys Pro Pro Arg Glu
            340                 345                 350

Asp Leu Lys
        355

<210> SEQ ID NO 8
<211> LENGTH: 358
<212> TYPE: PRT
<213> ORGANISM: Artificial Sequence
<220> FEATURE:
<223> OTHER INFORMATION: synthetic anti-mesothelin monoclonal antibody
      recombinant immunotoxin SS1-LR/GGS/8M variable heavy chain (VH-PE)

<400> SEQUENCE: 8

Met Gln Val Gln Leu Gln Gln Ser Gly Pro Glu Leu Glu Lys Pro Gly
1               5                   10                  15

Ala Ser Val Lys Ile Ser Cys Lys Ala Ser Gly Tyr Ser Phe Thr Gly
            20                  25                  30

Tyr Thr Met Asn Trp Val Lys Gln Ser His Gly Lys Cys Leu Glu Trp
        35                  40                  45

Ile Gly Leu Ile Thr Pro Tyr Asn Gly Ala Ser Ser Tyr Asn Gln Lys
    50                  55                  60

Phe Arg Gly Lys Ala Thr Leu Thr Val Asp Lys Ser Ser Ser Thr Ala
65                  70                  75                  80

Tyr Met Asp Leu Leu Ser Leu Thr Ser Glu Asp Ser Ala Val Tyr Phe
                85                  90                  95

Cys Ala Arg Gly Gly Tyr Asp Gly Arg Gly Phe Asp Tyr Trp Gly Gln
            100                 105                 110

Gly Thr Thr Val Thr Val Ser Ser Lys Ala Ser Gly Gly Arg His Arg
        115                 120                 125

Gln Pro Arg Gly Trp Glu Gln Leu Gly Gly Ser Pro Thr Gly Ala Glu
    130                 135                 140

Phe Leu Gly Asp Gly Gly Ala Val Ser Phe Ser Thr Arg Gly Thr Gln
145                 150                 155                 160

Asn Trp Thr Val Glu Arg Leu Leu Gln Ala His Arg Gln Leu Glu Glu
                165                 170                 175

Gly Gly Tyr Val Phe Val Gly Tyr His Gly Thr Phe Leu Glu Ala Ala
            180                 185                 190

Gln Ser Ile Val Phe Gly Gly Val Arg Ala Arg Ser Gln Asp Leu Asp
        195                 200                 205

Ala Ile Trp Ala Gly Phe Tyr Ile Ala Gly Asp Pro Ala Leu Ala Tyr
    210                 215                 220

Gly Tyr Ala Gln Asp Gln Glu Pro Asp Ala Gly Arg Ile Arg Asn
225                 230                 235                 240

Gly Ala Leu Leu Arg Val Tyr Val Pro Arg Ser Ser Leu Pro Gly Phe
                245                 250                 255

Tyr Ala Thr Ser Leu Thr Leu Ala Ala Pro Glu Ala Ala Gly Glu Val

```
                260                 265                 270
Glu Arg Leu Ile Gly His Pro Leu Pro Leu Arg Leu Asp Ala Ile Thr
            275                 280                 285

```
Tyr Arg Thr Ser Leu Thr Leu Ala Ala Pro Glu Ala Ala Gly Glu Val
            260                 265                 270

Glu Arg Leu Ile Gly His Pro Leu Pro Leu Arg Leu Asp Ala Ile Thr
        275                 280                 285

Gly Pro Glu Glu Glu Gly Gly Arg Leu Glu Thr Ile Leu Gly Trp Pro
    290                 295                 300

Leu Ala Glu Arg Thr Val Val Ile Pro Ser Ala Ile Pro Thr Asp Pro
305                 310                 315                 320

Arg Asn Val Gly Gly Asp Leu Asp Pro Ser Ser Ile Pro Asp Lys Glu
                325                 330                 335

Gln Ala Ile Ser Ala Leu Pro Asp Tyr Ala Ser Gln Pro Gly Lys Pro
            340                 345                 350

Pro Arg Glu Asp Leu Lys
        355

<210> SEQ ID NO 10
<211> LENGTH: 324
<212> TYPE: DNA
<213> ORGANISM: Artificial Sequence
<220> FEATURE:
<223> OTHER INFORMATION: synthetic anti-mesothelin monoclonal antibody
      SS1 variable light chain (V-L)

<400> SEQUENCE: 10
atggacatcg agctcactca gtctccagca atcatgtctg catctccagg ggagaaggtc    60
accatgacct gcagtgccag ctcaagtgta agttacatgc actggtacca gcagaagtca   120
ggcacctccc ccaaaagatg gatttatgac acatccaaac tggcttctgg agtcccaggt   180
cgcttcagtg gcagtgggtc tggaaactct tactctctca caatcagcag cgtggaggct   240
gaagatgatg caacttatta ctgccagcag tggtccaagc accctctcac gttcggttgc   300
gggacaaagt tggaaataaa ataa                                          324

<210> SEQ ID NO 11
<211> LENGTH: 1068
<212> TYPE: DNA
<213> ORGANISM: Artificial Sequence
<220> FEATURE:
<223> OTHER INFORMATION: synthetic anti-mesothelin monoclonal antibody
      recombinant immunotoxin SS1-LR variable heavy chain (VH-PE)

<400> SEQUENCE: 11
atgcaggtac aactgcagca gtctgggcct gagctggaga agcctggcgc ttcagtgaag    60
atatcctgca aggcatctgg ttactcattc actggctaca ccatgaactg ggtgaagcag   120
agtcatggaa agtgccttga gtggattgga cttattactc cttacaatgg tgcttctagc   180
tacaaccaga agttcagggg caaggccaca ttaactgtag acaagtcatc cagcacagcc   240
tacatggacc tcctcagtct gacatctgaa gactctgcag tctatttctg tgcaaggggg   300
ggttacgacg ggagggggtt tgactactgg ggccaaggga ccacggtcac cgtctcctca   360
aaagcttccg gaggtcgtca ccgtcaacca cgcggttggg aacagctgcc aaccggtgcc   420
gagttcctgg cgacggtgg cgatgtgtcc tttagcaccc gtggtaccca gaactggacg   480
gtagagcgcc tgctgcaggc catcgtcag ctggaagagc gtggctatgt attcgttggc   540
taccacggca ctttctgga agcagctcag tccatcgtgt tggtggtgt ccgtgcccgt    600 tctcaagacc tggatgcgat tggcgtggt ttctacattg caggcgatcc agcgctggca   660
tacggttatg cgcaggacca ggaaccggat gctcgcggtc gcattcgtaa tggtgcgctg   720
```

```
ctgcgcgtat atgtgccgcg ttccagcctg ccgggcttct accgcactag cctgaccctg      780
gccgcgccgg aggcggcggg tgaagtggaa cgtctgattg gtcatcctct gcctctgcgc      840
ctggatgcca tcaccggccc agaggaggag ggcggtcgtc tggaaaccat tctgggctgg      900
ccgctggctg aacgtacggt cgttattccg agcgcgattc ctaccgatcc tcgtaacgtt      960
ggcggcgatc tggacccatc ttctattcca gataaggagc aggcaatctc cgcgctgccg     1020
gattatgcaa gccaaccggg taaaccacct cgtgaagatc tgaaataa                  1068
```

<210> SEQ ID NO 12
<211> LENGTH: 1077
<212> TYPE: DNA
<213> ORGANISM: Artificial Sequence
<220> FEATURE:
<223> OTHER INFORMATION: synthetic anti-mesothelin monoclonal antibody
      recombinant immunotoxin SS1-LR/GGS/8M variable heavy chain (VH-PE)

<400> SEQUENCE: 12

```
atgcaggtac aactgcagca gtctgggcct gagctggaga agcctggcgc ttcagtgaag       60
atatcctgca aggcatctgg ttactcattc actggctaca ccatgaactg ggtgaagcag      120
agtcatggaa agtgccttga gtggattgga cttattactc cttacaatgg tgcttctagc      180
tacaaccaga gttcaggggg caaggccaca ttaactgtag acaagtcatc cagcacagcc      240
tacatggacc tcctcagtct gacatctgaa gactctgcag tctatttctg tgcaggggg       300 ggttacgacg ggagggggttt tgactactgg ggccaaggga ccacggtcac cgtctcctca      360
aaagcttccg gaggtcgtca tcgccagccg cgcggctggg aacaactggg tggaagtccc      420
actggcgcgg agttcctcgg cgacggcggc gcagtcagct tcagcacccg cggcacgcag      480
aactggacgg tggagcggct gctccaggcg caccgccaac tggaggaggg cggctatgtg      540
ttcgtcggct accacggcac cttcctcgaa gcggcgcaaa gcatcgtctt cggcggggtg      600
cgcgcgcgca gccaggacct cgacgcgatc tgggccggtt ctatatcgc cggcgatccg      660 gcgctggcct acggctacgc ccaggaccag gaacccgacg cagccggccg tatccgcaac      720
ggtgccctgc tgcgggtcta tgtgccgcgc tcgagcctgc cgggcttcta cgccaccagc      780
ctgaccctgg ccgcgccgga ggcggcgggc gaggtcgaac ggctgatcgg ccatcgctg      840 ccgctgcgcc tggacgccat caccggcccc gaggagtcag gcgggcgcct ggagaccatt      900
ctcggctggc cgctggccga cgcaccgtg gtgattccct cggcgatccc caccgacccg      960
cgcaacgtcg gcggcgacct cgacccgtcc agcatccccg acagcgaagc agcgatcagc     1020
gccctgccgg actacgccag ccagcccggc aaaccgccgc gcgaggacct gaagtaa       1077
```

<210> SEQ ID NO 13
<211> LENGTH: 1068
<212> TYPE: DNA
<213> ORGANISM: Artificial Sequence
<220> FEATURE:
<223> OTHER INFORMATION: synthetic anti-mesothelin monoclonal antibody
      recombinant immunotoxin SS1-LR/8M variable heavy chain (VH-PE)

<400> SEQUENCE: 13

```
atgcaggtac aactgcagca gtctgggcct gagctggaga agcctggcgc ttcagtgaag       60
atatcctgca aggcatctgg ttactcattc actggctaca ccatgaactg ggtgaagcag      120
agtcatggaa agtgccttga gtggattgga cttattactc cttacaatgg tgcttctagc      180
tacaaccaga gttcaggggg caaggccaca ttaactgtag acaagtcatc cagcacagcc      240
tacatggacc tcctcagtct gacatctgaa gactctgcag tctatttctg tgcaggggg       300
```

```
ggttacgacg ggagggsttt tgactactgg ggccaaggga ccacggtcac cgtctcctca    360
aaagcttccg gaggtcgtca tcgccagccg cgcggctggg aacaactgcc cactggcgcg    420
gagttcctcg cgacggcgg cgcagtcagc ttcagcaccc gcggcacgca gaactggacg    480
gtggagcggc tgctccaggc gcaccgccaa ctggaggagg cgggctatgt gttcgtcggc    540
taccacggca ccttcctcga agcggcgcaa agcatcgtct tcggcggggt gcgcgcgcgc    600
agccaggacc tcgacgcgat ctgggccggt ttctatatcg ccggcgatcc ggcgctggcc    660
tacggctacg cccaggacca ggaacccgac gcagccggcc gtatccgcaa cggtgccctg    720
ctgcgggtct atgtgccgcg ctcgagcctg ccgggcttct acgccaccag cctgaccctg    780
gccgcgccgg aggcggcggg cgaggtcgaa cggctgatcg ccatccgct gccgctgcgc    840 ctggacgcca tcaccggccc cgaggagtca ggcgggcgcc tggagaccat ctcggctgg    900 ccgctggccg agcgcaccgt ggtgattccc tcggcgatcc ccaccgaccc gcgcaacgtc    960
ggcggcgacc tcgacccgtc cagcatcccc gacagcgaag cagcgatcag cgccctgccg    1020
gactacgcca gccagcccgg caaaccgccg cgcgaggacc tgaagtaa              1068
```

<210> SEQ ID NO 14
<211> LENGTH: 241
<212> TYPE: PRT
<213> ORGANISM: Artificial Sequence
<220> FEATURE:
<223> OTHER INFORMATION: synthetic anti-mesothelin Fv antibody (SS scFv)

<400> SEQUENCE: 14

```
Met Gln Val Gln Leu Gln Gln Ser Gly Pro Glu Leu Glu Lys Pro Gly
1               5                   10                  15

Ala Ser Val Lys Leu Ser Cys Lys Ala Ser Gly Tyr Ser Phe Thr Gly
            20                  25                  30

Tyr Thr Met Asn Trp Val Lys Gln Ser His Gly Lys Ser Leu Glu Trp
        35                  40                  45

Ile Gly Leu Ile Thr Pro Tyr Asn Gly Ala Ser Ser Tyr Asn Gln Lys
    50                  55                  60

Phe Arg Gly Lys Ala Thr Leu Thr Val Asp Lys Ser Ser Ser Thr Ala
65                  70                  75                  80

Tyr Met Asp Leu Leu Ser Leu Thr Ser Glu Asp Ser Ala Val Tyr Phe
                85                  90                  95

Cys Ala Arg Gly Gly Tyr Asp Gly Arg Gly Phe Asp Tyr Trp Gly Gln
            100                 105                 110

Gly Thr Thr Val Thr Val Ser Ser Gly Val Gly Gly Ser Gly Gly Gly
        115                 120                 125

Gly Ser Gly Gly Gly Ser Asp Ile Glu Leu Thr Gln Ser Pro Ala
    130                 135                 140

Ile Met Ser Ala Ser Pro Gly Glu Lys Val Thr Met Thr Cys Ser Ala
145                 150                 155                 160

Ser Ser Ser Val Ser Tyr Met His Trp Tyr Gln Gln Lys Ser Gly Thr
                165                 170                 175

Ser Pro Lys Arg Trp Ile Tyr Asp Thr Ser Lys Leu Ala Ser Gly Val
            180                 185                 190

Pro Gly Arg Phe Ser Gly Ser Gly Ser Gly Asn Ser Tyr Ser Leu Thr
        195                 200                 205

Ile Ser Ser Val Glu Ala Glu Asp Asp Ala Thr Tyr Tyr Cys Gln Gln
    210                 215                 220
```

Trp Ser Gly Tyr Pro Leu Thr Phe Gly Ala Gly Thr Lys Leu Glu Ile
225                 230                 235                 240
Lys

<210> SEQ ID NO 15
<211> LENGTH: 5
<212> TYPE: PRT
<213> ORGANISM: Artificial Sequence
<220> FEATURE:
<223> OTHER INFORMATION: synthetic C-terminal residues of native PE

<400> SEQUENCE: 15

Arg Glu Asp Leu Lys
1               5

<210> SEQ ID NO 16
<211> LENGTH: 4
<212> TYPE: PRT
<213> ORGANISM: Artificial Sequence
<220> FEATURE:
<223> OTHER INFORMATION: synthetic canonical endoplasmic reticulum
      retention signal

<400> SEQUENCE: 16

Lys Asp Glu Leu
1

<210> SEQ ID NO 17
<211> LENGTH: 11
<212> TYPE: PRT
<213> ORGANISM: Artificial Sequence
<220> FEATURE:
<223> OTHER INFORMATION: synthetic furin cleavage site (FCS)

<400> SEQUENCE: 17

Arg His Arg Gln Pro Arg Gly Trp Glu Gln Leu
1               5                   10

<210> SEQ ID NO 18
<211> LENGTH: 6
<212> TYPE: PRT
<213> ORGANISM: Artificial Sequence
<220> FEATURE:
<223> OTHER INFORMATION: synthetic flexible linker (FL)

<400> SEQUENCE: 18

Gly Gly Ser Gly Gly Ser
1               5

<210> SEQ ID NO 19
<211> LENGTH: 4
<212> TYPE: PRT
<213> ORGANISM: Artificial Sequence
<220> FEATURE:
<223> OTHER INFORMATION: synthetic short peptide linker

<400> SEQUENCE: 19

Ala Ser Gly Gly
1

<210> SEQ ID NO 20
<211> LENGTH: 15
<212> TYPE: PRT
<213> ORGANISM: Artificial Sequence
<220> FEATURE:
<223> OTHER INFORMATION: synthetic short peptide linker and furin
      cleavage site for SS1-LR

<400> SEQUENCE: 20

Ala Ser Gly Gly Arg His Arg Gln Pro Arg Gly Trp Glu Gln Leu
1               5                   10                  15

<210> SEQ ID NO 21
<211> LENGTH: 18
<212> TYPE: PRT
<213> ORGANISM: Artificial Sequence
<220> FEATURE:
<223> OTHER INFORMATION: synthetic short peptide linker and furin
      cleavage site for SS1-LR/GGS

<400> SEQUENCE: 21

Ala Ser Gly Gly Arg His Arg Gln Pro Arg Gly Trp Glu Gln Leu Gly
1               5                   10                  15

Gly Ser

<210> SEQ ID NO 22
<211> LENGTH: 26
<212> TYPE: PRT
<213> ORGANISM: Artificial Sequence
<220> FEATURE:
<223> OTHER INFORMATION: synthetic short peptide linker and furin
      cleavage site for SS1-LR/GGSx2

<400> SEQUENCE: 22

Ala Ser Gly Gly Ser Gly Gly Gly Arg His Arg Gln Pro Arg Gly Trp
1               5                   10                  15

Glu Gln Leu Gly Gly Ser Gly Gly Gly Ser
            20                  25

<210> SEQ ID NO 23
<211> LENGTH: 32
<212> TYPE: PRT
<213> ORGANISM: Artificial Sequence
<220> FEATURE:
<223> OTHER INFORMATION: synthetic short peptide linker and furin
      cleavage siste for SS1-LR/2xFurin

<400> SEQUENCE: 23

Ala Ser Gly Gly Arg His Arg Gln Pro Arg Gly Trp Glu Gln Leu Gly
1               5                   10                  15

Gly Ser Arg His Arg Gln Pro Arg Gly Trp Glu Gln Leu Gly Gly Ser
            20                  25                  30

<210> SEQ ID NO 24
<211> LENGTH: 18
<212> TYPE: PRT
<213> ORGANISM: Artificial Sequence
<220> FEATURE:
<223> OTHER INFORMATION: synthetic short peptide linker and furin
      cleavage site for SS1-LR/GGS R279G

<400> SEQUENCE: 24

Ala Ser Gly Gly Arg His Arg Gln Pro Gly Gly Trp Glu Gln Leu Gly
1               5                   10                  15

Gly Ser

<210> SEQ ID NO 25
<211> LENGTH: 14
<212> TYPE: PRT
<213> ORGANISM: Artificial Sequence
<220> FEATURE:
<223> OTHER INFORMATION: synthetic scFv linker peptide

```
<400> SEQUENCE: 25

Gly Val Gly Gly Ser Gly Gly Gly Ser Gly Gly Gly Gly
1               5                   10

<210> SEQ ID NO 26
<211> LENGTH: 4
<212> TYPE: PRT
<213> ORGANISM: Artificial Sequence
<220> FEATURE:
<223> OTHER INFORMATION: synthetic carboxyl terminus endoplasmic
      reticulum retention signal

<400> SEQUENCE: 26

Arg Glu Asp Leu
1

<210> SEQ ID NO 27
<211> LENGTH: 4
<212> TYPE: PRT
<213> ORGANISM: Artificial Sequence
<220> FEATURE:
<223> OTHER INFORMATION: synthetic mutated terminal residues of PE

<400> SEQUENCE: 27

Arg Glu Glu Leu
1

<210> SEQ ID NO 28
<211> LENGTH: 4
<212> TYPE: PRT
<213> ORGANISM: Artificial Sequence
<220> FEATURE:
<223> OTHER INFORMATION: synthetic mutated terminal residues of PE

<400> SEQUENCE: 28

Arg Asp Glu Leu
1

<210> SEQ ID NO 29
<211> LENGTH: 11
<212> TYPE: PRT
<213> ORGANISM: Artificial Sequence
<220> FEATURE:
<223> OTHER INFORMATION: synthetic substituted furin cleavage site

<400> SEQUENCE: 29

Arg His Arg Ser Lys Arg Gly Trp Glu Gln Leu
1               5                   10

<210> SEQ ID NO 30
<211> LENGTH: 4
<212> TYPE: PRT
<213> ORGANISM: Artificial Sequence
<220> FEATURE:
<223> OTHER INFORMATION: synthetic minimal furin cleavage site

<400> SEQUENCE: 30

Arg Lys Lys Arg
1

<210> SEQ ID NO 31
<211> LENGTH: 4
<212> TYPE: PRT
<213> ORGANISM: Artificial Sequence
<220> FEATURE:
<223> OTHER INFORMATION: synthetic minimal furin cleavage site
```

```
<400> SEQUENCE: 31

Arg Arg Arg Arg
1

<210> SEQ ID NO 32
<211> LENGTH: 4
<212> TYPE: PRT
<213> ORGANISM: Artificial Sequence
<220> FEATURE:
<223> OTHER INFORMATION: synthetic minimal furin cleavage site

<400> SEQUENCE: 32

Arg Lys Ala Arg
1

<210> SEQ ID NO 33
<211> LENGTH: 6
<212> TYPE: PRT
<213> ORGANISM: Artificial Sequence
<220> FEATURE:
<223> OTHER INFORMATION: synthetic furin cleavage site

<400> SEQUENCE: 33

Ser Arg Val Ala Arg Ser
1               5

<210> SEQ ID NO 34
<211> LENGTH: 9
<212> TYPE: PRT
<213> ORGANISM: Artificial Sequence
<220> FEATURE:
<223> OTHER INFORMATION: synthetic furin cleavage site

<400> SEQUENCE: 34

Thr Ser Ser Arg Lys Arg Arg Phe Trp
1               5

<210> SEQ ID NO 35
<211> LENGTH: 9
<212> TYPE: PRT
<213> ORGANISM: Artificial Sequence
<220> FEATURE:
<223> OTHER INFORMATION: synthetic furin cleavage site

<400> SEQUENCE: 35

Ala Ser Arg Arg Lys Ala Arg Ser Trp
1               5

<210> SEQ ID NO 36
<211> LENGTH: 8
<212> TYPE: PRT
<213> ORGANISM: Artificial Sequence
<220> FEATURE:
<223> OTHER INFORMATION: synthetic furin cleavage site

<400> SEQUENCE: 36

Arg Arg Val Lys Lys Arg Phe Trp
1               5

<210> SEQ ID NO 37
<211> LENGTH: 8
<212> TYPE: PRT
<213> ORGANISM: Artificial Sequence
<220> FEATURE:
<223> OTHER INFORMATION: synthetic furin cleavage site
```

```
<400> SEQUENCE: 37

Arg Asn Val Val Arg Arg Asp Trp
1               5

<210> SEQ ID NO 38
<211> LENGTH: 9
<212> TYPE: PRT
<213> ORGANISM: Artificial Sequence
<220> FEATURE:
<223> OTHER INFORMATION: synthetic furin cleavage site

<400> SEQUENCE: 38

Thr Arg Ala Val Arg Arg Arg Ser Trp
1               5

<210> SEQ ID NO 39
<211> LENGTH: 4
<212> TYPE: PRT
<213> ORGANISM: Artificial Sequence
<220> FEATURE:
<223> OTHER INFORMATION: synthetic furin cleavage site

<400> SEQUENCE: 39

Arg Gln Pro Arg
1

<210> SEQ ID NO 40
<211> LENGTH: 8
<212> TYPE: PRT
<213> ORGANISM: Artificial Sequence
<220> FEATURE:
<223> OTHER INFORMATION: synthetic furin cleavage site

<400> SEQUENCE: 40

Arg His Arg Gln Pro Arg Gly Trp
1               5

<210> SEQ ID NO 41
<211> LENGTH: 9
<212> TYPE: PRT
<213> ORGANISM: Artificial Sequence
<220> FEATURE:
<223> OTHER INFORMATION: synthetic furin cleavage site

<400> SEQUENCE: 41

Arg His Arg Gln Pro Arg Gly Trp Glu
1               5

<210> SEQ ID NO 42
<211> LENGTH: 9
<212> TYPE: PRT
<213> ORGANISM: Artificial Sequence
<220> FEATURE:
<223> OTHER INFORMATION: synthetic furin cleavage site

<400> SEQUENCE: 42

His Arg Gln Pro Arg Gly Trp Glu Gln
1               5

<210> SEQ ID NO 43
<211> LENGTH: 7
<212> TYPE: PRT
<213> ORGANISM: Artificial Sequence
<220> FEATURE:
<223> OTHER INFORMATION: synthetic furin cleavage site

<400> SEQUENCE: 43
```

Arg Gln Pro Arg Gly Trp Glu
1               5

<210> SEQ ID NO 44
<211> LENGTH: 4
<212> TYPE: PRT
<213> ORGANISM: Artificial Sequence
<220> FEATURE:
<223> OTHER INFORMATION: synthetic furin cleavage site

<400> SEQUENCE: 44

Arg Ser Lys Arg
1

<210> SEQ ID NO 45
<211> LENGTH: 8
<212> TYPE: PRT
<213> ORGANISM: Artificial Sequence
<220> FEATURE:
<223> OTHER INFORMATION: synthetic furin cleavage site

<400> SEQUENCE: 45

Arg His Arg Ser Lys Arg Gly Trp
1               5

<210> SEQ ID NO 46
<211> LENGTH: 8
<212> TYPE: PRT
<213> ORGANISM: Artificial Sequence
<220> FEATURE:
<223> OTHER INFORMATION: synthetic furin cleavage site

<400> SEQUENCE: 46

His Arg Ser Lys Arg Gly Trp Glu
1               5

<210> SEQ ID NO 47
<211> LENGTH: 9
<212> TYPE: PRT
<213> ORGANISM: Artificial Sequence
<220> FEATURE:
<223> OTHER INFORMATION: synthetic furin cleavage site

<400> SEQUENCE: 47

Arg Ser Lys Arg Gly Trp Glu Gln Leu
1               5

<210> SEQ ID NO 48
<211> LENGTH: 10
<212> TYPE: PRT
<213> ORGANISM: Artificial Sequence
<220> FEATURE:
<223> OTHER INFORMATION: synthetic furin cleavage site

<400> SEQUENCE: 48

His Arg Ser Lys Arg Gly Trp Glu Gln Leu
1               5                   10

<210> SEQ ID NO 49
<211> LENGTH: 6
<212> TYPE: PRT
<213> ORGANISM: Artificial Sequence
<220> FEATURE:
<223> OTHER INFORMATION: synthetic furin cleavage site

<400> SEQUENCE: 49

Arg His Arg Ser Lys Arg
1               5

<210> SEQ ID NO 50
<211> LENGTH: 4
<212> TYPE: PRT
<213> ORGANISM: Artificial Sequence
<220> FEATURE:
<223> OTHER INFORMATION: synthetic scFv peptide linker

<400> SEQUENCE: 50

Gly Gly Gly Ser
1

<210> SEQ ID NO 51
<211> LENGTH: 5
<212> TYPE: PRT
<213> ORGANISM: Artificial Sequence
<220> FEATURE:
<223> OTHER INFORMATION: synthetic anti-mesothelin monoclonal antibody
      variable heavy chain CDR1

<400> SEQUENCE: 51

Gly Tyr Thr Met Asn
1               5

<210> SEQ ID NO 52
<211> LENGTH: 17
<212> TYPE: PRT
<213> ORGANISM: Artificial Sequence
<220> FEATURE:
<223> OTHER INFORMATION: synthetic anti-mesothelin monoclonal
      antibody variable heavy chain CDR2

<400> SEQUENCE: 52

Leu Ile Thr Pro Tyr Asn Gly Ala Ser Ser Tyr Asn Gln Lys Phe Arg
1               5                   10                  15

Gly

<210> SEQ ID NO 53
<211> LENGTH: 10
<212> TYPE: PRT
<213> ORGANISM: Artificial Sequence
<220> FEATURE:
<223> OTHER INFORMATION: synthetic anti-mesothelin monoclonal
      antibody variable heavy chain CDR3

<400> SEQUENCE: 53

Gly Gly Tyr Asp Gly Arg Gly Phe Asp Tyr
1               5                   10

<210> SEQ ID NO 54
<211> LENGTH: 10
<212> TYPE: PRT
<213> ORGANISM: Artificial Sequence
<220> FEATURE:
<223> OTHER INFORMATION: synthetic anti-mesothelin monoclonal
      antibody variable light chain CDR1

<400> SEQUENCE: 54

Ser Ala Ser Ser Ser Val Ser Tyr Met His
1               5                   10

<210> SEQ ID NO 55
<211> LENGTH: 7
<212> TYPE: PRT
<213> ORGANISM: Artificial Sequence

```
<220> FEATURE:
<223> OTHER INFORMATION: synthetic anti-mesothelin monoclonal
      antibody variable light chain CDR2

<400> SEQUENCE: 55

Asp Thr Ser Lys Leu Ala Ser
1               5

<210> SEQ ID NO 56
<211> LENGTH: 9
<212> TYPE: PRT
<213> ORGANISM: Artificial Sequence
<220> FEATURE:
<223> OTHER INFORMATION: synthetic anti-mesothelin monoclonal
      antibody variable light chain CDR3

<400> SEQUENCE: 56

Gln Gln Trp Ser Gly Tyr Pro Leu Thr
1               5

<210> SEQ ID NO 57
<211> LENGTH: 9
<212> TYPE: PRT
<213> ORGANISM: Artificial Sequence
<220> FEATURE:
<223> OTHER INFORMATION: synthetic anti-mesothelin monoclonal
      antibody variable light chain CDR3

<400> SEQUENCE: 57

Gln Gln Trp Ser Lys His Pro Leu Thr
1               5

<210> SEQ ID NO 58
<211> LENGTH: 9
<212> TYPE: PRT
<213> ORGANISM: Artificial Sequence
<220> FEATURE:
<223> OTHER INFORMATION: synthetic anti-mesothelin monoclonal
      antibody variable light chain CDR3

<400> SEQUENCE: 58

Gln Gln Trp Ser Gly His Pro Leu Thr
1               5

<210> SEQ ID NO 59
<211> LENGTH: 9
<212> TYPE: PRT
<213> ORGANISM: Artificial Sequence
<220> FEATURE:
<223> OTHER INFORMATION: synthetic anti-mesothelin monoclonal
      antibody variable light chain CDR3

<400> SEQUENCE: 59

Gln Gln Trp Ser Ala His Pro Leu Thr
1               5

<210> SEQ ID NO 60
<211> LENGTH: 9
<212> TYPE: PRT
<213> ORGANISM: Artificial Sequence
<220> FEATURE:
<223> OTHER INFORMATION: synthetic anti-mesothelin monoclonal
      antibody variable light chain CDR3

<400> SEQUENCE: 60

Gln Gln Trp Ser Gln Ile Pro Leu Thr
1               5
```

<210> SEQ ID NO 61
<211> LENGTH: 9
<212> TYPE: PRT
<213> ORGANISM: Artificial Sequence
<220> FEATURE:
<223> OTHER INFORMATION: synthetic anti-mesothelin monoclonal
      antibody variable light chain CDR3

<400> SEQUENCE: 61

Gln Gln Trp Gly Phe Asn Pro Leu Thr
1               5

<210> SEQ ID NO 62
<211> LENGTH: 9
<212> TYPE: PRT
<213> ORGANISM: Artificial Sequence
<220> FEATURE:
<223> OTHER INFORMATION: synthetic anti-mesothelin monoclonal
      antibody variable light chain CDR3

<400> SEQUENCE: 62

Gln Gln Trp Gly Thr Asn Pro Leu Thr
1               5

<210> SEQ ID NO 63
<211> LENGTH: 9
<212> TYPE: PRT
<213> ORGANISM: Artificial Sequence
<220> FEATURE:
<223> OTHER INFORMATION: synthetic anti-mesothelin monoclonal
      antibody variable light chain CDR3

<400> SEQUENCE: 63

Gln Gln Trp Gly Ser His Pro Leu Thr
1               5

<210> SEQ ID NO 64
<211> LENGTH: 9
<212> TYPE: PRT
<213> ORGANISM: Artificial Sequence
<220> FEATURE:
<223> OTHER INFORMATION: synthetic anti-mesothelin monoclonal
      antibody variable light chain CDR3

<400> SEQUENCE: 64

Gln Gln Trp Gly Asp Phe Pro Leu Thr
1               5

<210> SEQ ID NO 65
<211> LENGTH: 9
<212> TYPE: PRT
<213> ORGANISM: Artificial Sequence
<220> FEATURE:
<223> OTHER INFORMATION: synthetic anti-mesothelin monoclonal
      antibody variable light chain CDR3

<400> SEQUENCE: 65

Gln Gln Trp Gly Asp His Pro Leu Thr
1               5

<210> SEQ ID NO 66
<211> LENGTH: 9
<212> TYPE: PRT
<213> ORGANISM: Artificial Sequence
<220> FEATURE:
<223> OTHER INFORMATION: synthetic anti-mesothelin monoclonal
      antibody variable light chain CDR3

```
<400> SEQUENCE: 66

Gln Gln Trp Ser Ala His Pro Leu Thr
1               5

<210> SEQ ID NO 67
<211> LENGTH: 9
<212> TYPE: PRT
<213> ORGANISM: Artificial Sequence
<220> FEATURE:
<223> OTHER INFORMATION: synthetic anti-mesothelin monoclonal
      antibody variable light chain CDR3

<400> SEQUENCE: 67

Gln Gln Trp Ser Gly Tyr Pro Thr Thr
1               5

<210> SEQ ID NO 68
<211> LENGTH: 8
<212> TYPE: PRT
<213> ORGANISM: Artificial Sequence
<220> FEATURE:
<223> OTHER INFORMATION: synthetic linker joining carboxyl terminus
      of antibody to N-terminus of the furin cleavage site

<400> SEQUENCE: 68

Ala Ser Gly Gly Ser Gly Gly Gly
1               5

<210> SEQ ID NO 69
<211> LENGTH: 5
<212> TYPE: PRT
<213> ORGANISM: Artificial Sequence
<220> FEATURE:
<223> OTHER INFORMATION: synthetic flexible linker

<400> SEQUENCE: 69

Gly Gly Gly Ser Gly
1               5

<210> SEQ ID NO 70
<211> LENGTH: 6
<212> TYPE: PRT
<213> ORGANISM: Artificial Sequence
<220> FEATURE:
<223> OTHER INFORMATION: synthetic flexible linker

<400> SEQUENCE: 70

Gly Gly Gly Gly Ser Gly
1               5

<210> SEQ ID NO 71
<211> LENGTH: 4
<212> TYPE: PRT
<213> ORGANISM: Artificial Sequence
<220> FEATURE:
<223> OTHER INFORMATION: synthetic flexible linker (FL)

<400> SEQUENCE: 71

Gly Ser Gly Gly
1

<210> SEQ ID NO 72
<211> LENGTH: 5
<212> TYPE: PRT
<213> ORGANISM: Artificial Sequence
<220> FEATURE:
<223> OTHER INFORMATION: synthetic flexible linker (FL)
```

```
<400> SEQUENCE: 72

Gly Gly Ser Gly Gly
1               5

<210> SEQ ID NO 73
<211> LENGTH: 4
<212> TYPE: PRT
<213> ORGANISM: Artificial Sequence
<220> FEATURE:
<223> OTHER INFORMATION: synthetic flexible linker (FL)

<400> SEQUENCE: 73

Gly Gly Ser Gly
1
```